(12) United States Patent
Sharon et al.

(10) Patent No.: US 9,199,250 B2
(45) Date of Patent: Dec. 1, 2015

(54) DISPOSABLE SEPARATOR/CONCENTRATOR DEVICE AND METHOD OF USE

(75) Inventors: Andre Sharon, Newton, MA (US); Alexis Sauer-Budge, Lincoln, MA (US); Aaron Size, Waltham, MA (US); Holger Wirz, Medford, MA (US)

(73) Assignees: Trustees of Boston University, Boston, MA (US); Fraunhofer USA, Inc., Plymouth, MI (US)

( * ) Notice: Subject to any disclaimer, the term of this patent is extended or adjusted under 35 U.S.C. 154(b) by 949 days.

(21) Appl. No.: 13/266,980

(22) PCT Filed: Apr. 30, 2010

(86) PCT No.: PCT/US2010/033216
§ 371 (c)(1),
(2), (4) Date: Nov. 29, 2011

(87) PCT Pub. No.: WO2010/127278
PCT Pub. Date: Nov. 4, 2010

(65) Prior Publication Data
US 2012/0115705 A1 May 10, 2012

Related U.S. Application Data

(60) Provisional application No. 61/174,664, filed on May 1, 2009, provisional application No. 61/174,698, filed on May 1, 2009.

(51) Int. Cl.
*B04B 5/04* (2006.01)
*G01N 1/28* (2006.01)
(Continued)

(52) U.S. Cl.
CPC .............. *B04B 5/0421* (2013.01); *B04B 5/0407* (2013.01); *B04B 11/04* (2013.01);
(Continued)

(58) Field of Classification Search
CPC .................. B01L 3/0265; B01L 3/502; B01L 2400/0622; B04B 5/0407; B04B 5/0421; B04B 11/04

USPC .............. 494/2–5, 10, 12, 20, 26, 56, 84, 85; 422/548, 559; 210/255, 512.3; 251/89–116, 129.11, 162, 163
See application file for complete search history.

(56) References Cited

U.S. PATENT DOCUMENTS 4,511,349 A 4/1985 Nielsen et al.
4,661,732 A 4/1987 Gehrt
(Continued)

FOREIGN PATENT DOCUMENTS

CN 101256192 A 9/2008
WO 93/22673 A1 11/1993
WO 96/06679 A1 3/1996

OTHER PUBLICATIONS

Brazhnikova, A. V., "Centrifuge for Difficult to Separate Slurries" Abstract of U.S. Pat. No. 3,494,452, 1968.
(Continued)

*Primary Examiner* — Timothy Cleveland
(74) *Attorney, Agent, or Firm* — Nixon Peabody LLP

(57) ABSTRACT

The present invention relates to methods, devices and systems for separation and concentration of particles from liquid and fluid samples. In some embodiments, the separation/concentration is achieved by sequential centrifugation steps. In particular, one aspect of the invention relates to a separation/concentration device which comprises at least a first chamber (101) and a second chamber (103) connected by a first valve (111), whereby operation of the first valve controls the material transfer from the first chamber to the second chamber. In some embodiments, valve operation can be manually, semi-manually or automatically. Other aspects of the invention relate to single- or multi-chambered separation/concentrator devices, and methods and systems for use. Other aspects of the invention relate to devices for operation of the valves, e.g., semi-manual actuation devices, and automatic inertial activation devices and mechanical actuation devices present in purpose-built centrifuges.

20 Claims, 45 Drawing Sheets

(51) Int. Cl.
    *G01N 15/04*       (2006.01)
    *G01N 15/05*       (2006.01)
    *B04B 11/04*       (2006.01)
    *B01L 3/00*        (2006.01)
    *G01N 35/00*       (2006.01)

(52) U.S. Cl.
    CPC ........... *G01N 1/2813* (2013.01); *G01N 15/042* (2013.01); *G01N 15/05* (2013.01); *B01L 3/502* (2013.01); *G01N 2035/00495* (2013.01)

(56) References Cited

U.S. PATENT DOCUMENTS

| | | |
|---|---|---|
| 4,812,294 A | 3/1989 | Combs |
| 5,039,401 A | 8/1991 | Columbus et al. |
| 5,171,533 A | 12/1992 | Fine |
| 5,520,424 A | 5/1996 | Hapke et al. |
| 5,603,845 A | 2/1997 | Holm |
| 5,618,409 A | 4/1997 | Kreill |
| 5,707,331 A | 1/1998 | Wells et al. |
| 5,770,069 A * | 6/1998 | Meryman ............ 494/21 |
| 5,866,071 A | 2/1999 | Leu |
| 5,868,928 A | 2/1999 | Bradley |
| 5,984,207 A | 11/1999 | Wang |
| 6,000,675 A | 12/1999 | Eggleston |
| 6,168,107 B1 | 1/2001 | Bishop et al. |
| 6,602,414 B2 | 8/2003 | Warner |
| 7,033,501 B1 | 4/2006 | Bhaskar et al. |
| 7,052,451 B2 | 5/2006 | Carr |
| 7,140,340 B2 | 11/2006 | Hashimoto |
| 7,520,402 B2 | 4/2009 | Ellsworth et al. |
| 2008/0063567 A1 | 3/2008 | Schacher et al. |

OTHER PUBLICATIONS

Flynn, J., et al., "Inline Skate Speed Limiter" Design Application.
Van Duijn, P., et al. "A new type of cytocentrifuge, the valve-centrifuge" PMID: 863750 [PubMed—indexed for Medline].

* cited by examiner

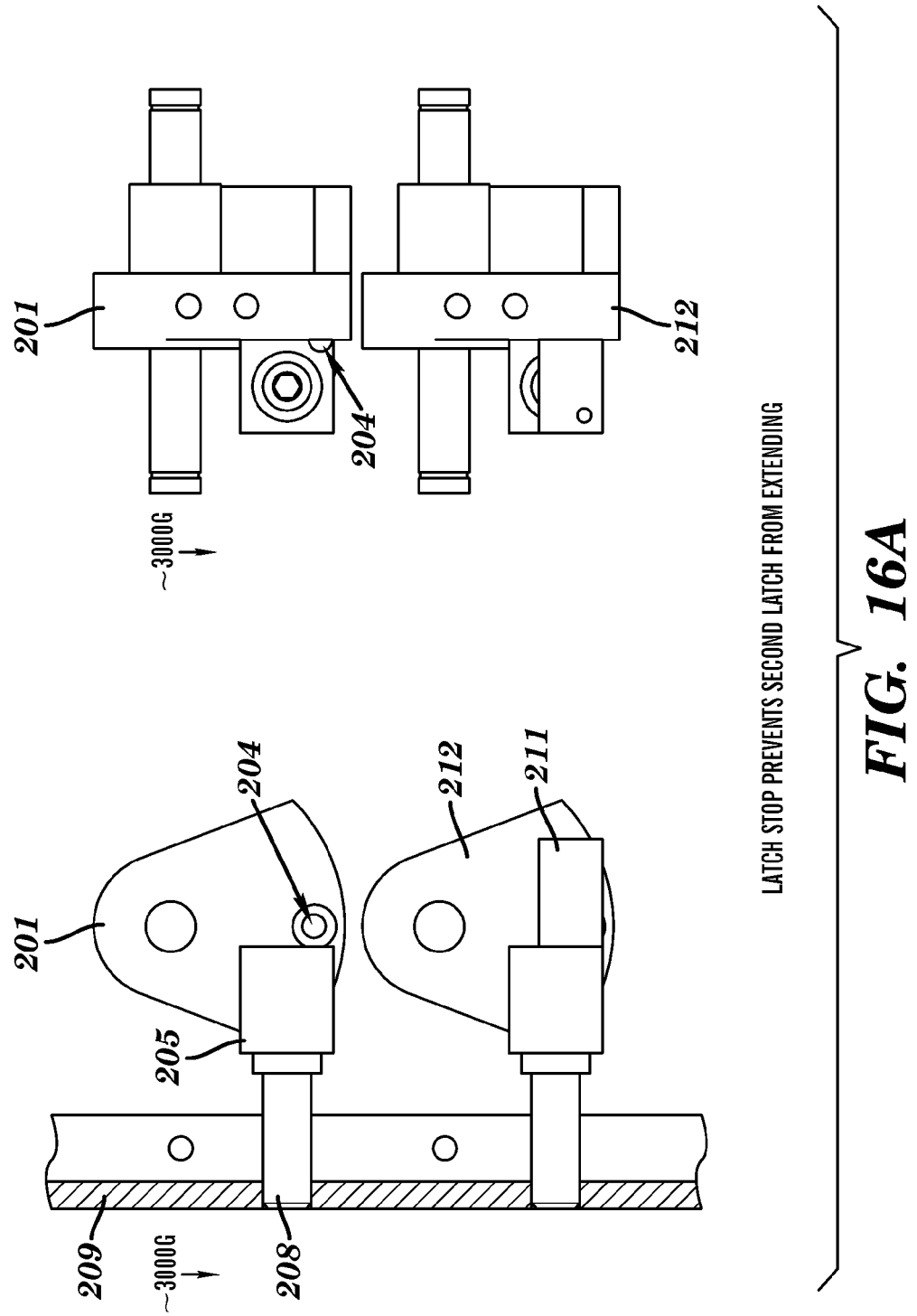
FIG. 16A — LATCH STOP PREVENTS SECOND LATCH FROM EXTENDING

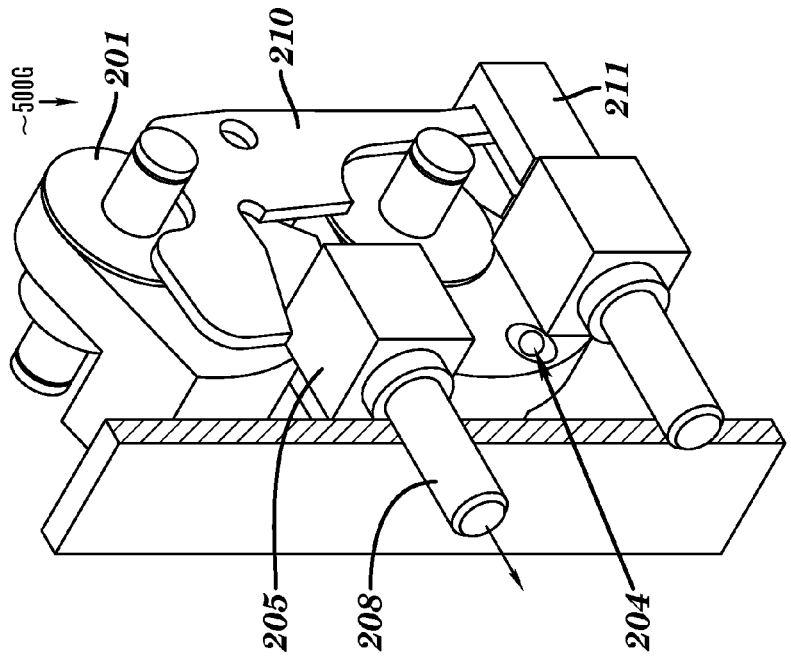
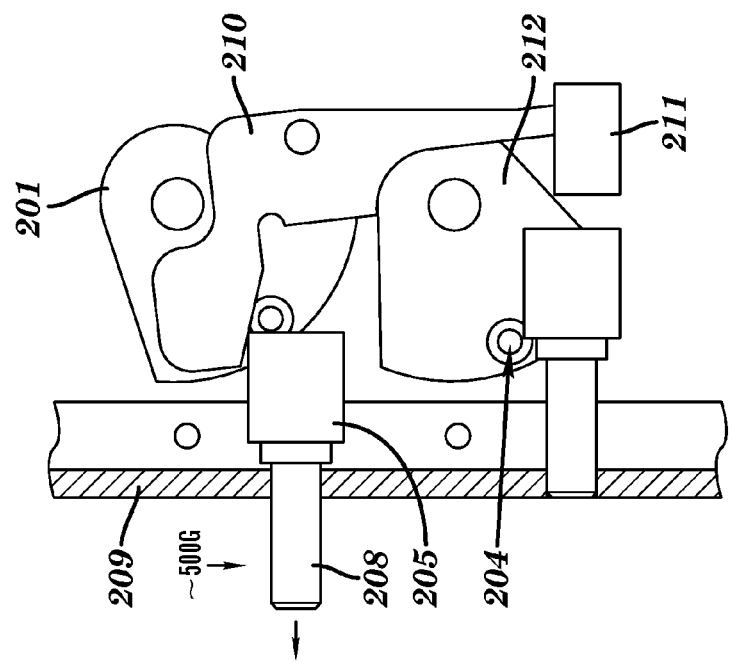
FIG. 16C
DURING FIRST CENTRIFUGE DECELERATION, LATCH STOP RELEASE SHIFTS THE LATCH STOP BACKWARDS.

DURING SECOND CENTRIFUGE DECELERATION

DURING SECOND CENTRIFUGE TOP SPEED

FIG. 31A

Accelerating G – Arm swinging down          (eq. 1)

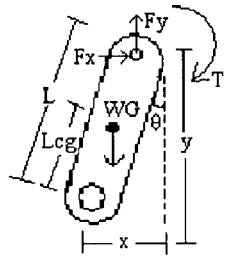

$\sum X : F_x = 0$ $\sum Y : F_y - WG = 0$ $\sum M : k_t \alpha - WGL \sin \theta = 0$

FIG. 31B

Decelerating G – Arm swinging up, actuating valve          (eq. 2)

$\sum X : F_x = 0$ $\sum Y : F_y - WG = 0$ $\sum M : k_t \alpha - WGL \sin \theta = 0$

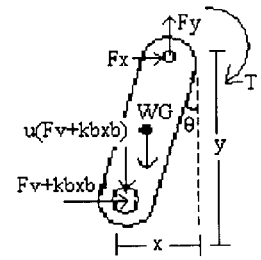

$$G = \frac{k_t \alpha - (Fv + k_b x_b)(L \cos \theta + \mu L \sin \theta)}{WL_{cg} \sin \theta} \qquad (eq.\ 3)$$

$$k_b = \frac{k_t \alpha - WGL_{cg} \sin \theta}{(L \cos \theta + \mu L \sin \theta)x_b} - \frac{Fv}{x_b} \qquad (eq.\ 4)$$

$$k_t = \frac{L(Fv + k_b x_b)(\cos \theta + \mu \sin \theta) + WGL_{cg} \sin \theta}{\alpha} \qquad (eq.\ 5)$$

*Variable definitions:*

$X_b$ = spring bolt displacement
= $L \sin \theta - L_{relaxed}$ where $L_{relaxed}$ = 0.0005 in
$k_t$ = torsion spring constant
$k_b$ = bolt spring constant
$Fv$ = valve force
$G$ = Gravitational force
$L_{cg}$ = length to the center of gravity of arm
$\mu$ = coefficient of friction
$\theta$ = angle from vertical axis to arm
$a = 220 - \theta$

US 9,199,250 B2

DISPOSABLE SEPARATOR/CONCENTRATOR DEVICE AND METHOD OF USE

CROSS REFERENCE TO RELATED APPLICATION

This application is a 35 U.S.C. §371 National Phase Entry Application of International Application No. PCT/US2010/033216 filed Apr. 30, 2010, which designates the U.S., and which claims benefit under 35 U.S.C. §119(e) of the U.S. provisional application No. 61/174,664 and U.S. provisional application No. 61/174,698, both filed on May 1, 2009, the contents of which are incorporated herein by reference in their entirety.

BACKGROUND OF INVENTION

The current standard for diagnosing a bacterial infection or bacterial contamination of water or food supply requires a relatively pure sample of bacteria culture. In order to obtain such a culture, the bacteria in the sample has to be grown in special media overnight in specialized, off-site laboratory. Biochemical tests are then used to identify the bacteria present in the culture. This procedure is labor-intensive and requires skilled laboratory technicians, and introduces the element of human error. Cell culturing is also inherently time-consuming and can require days or even weeks to culture slow-growing bacteria such as *Mycobacterium tuberculosis*.

Alternative methods and/or apparatus that speed up the above process and reduce labor involved have been developed.

SUMMARY OF THE INVENTION

The present invention relates to a particle or cell separation and concentration device that concentrates and separates particles, e.g., bacteria or contaminants, from a liquids or fluid samples. The separation/concentration is achieved by sequential centrifugation steps. Such a separator/concentrator device facilitates rapid extraction and concentration of bacteria or particles from a fluid sample, e.g., water, or a biological fluid samples, e.g., blood, and presents the concentrated sample which can be subsequently processed or analyzed. This separator/concentrator device as disclosed herein is also useful for producing a concentrated sample for analysis for downstream diagnostics assays, as the separator/concentrator device produces a concentrated sample, often resulting in purification and isolation of particulates from a sample, e.g. bacteria from fluid sample, e.g., blood or other biological fluids, e.g. for PCR, bioMEMS devices, etc.

In one embodiment, the invention is directed to a disposable device, herein referred to as a "separator/concentrator" device, where particle separation can occur in multiple centrifugation steps, and the sample can be passed from one chamber to another chamber in the disposable device during each centrifugation step. The flow of the sample from one chamber to another can be controlled by a valve located between each chamber, where the valve is operated by a variety of different mechanisms, for example, manually or automatically, as disclosed herein.

One aspect of the present invention relates to a device, e.g., a disposable device for separation and concentration of particulates from a fluid sample by centrifugation. In some embodiments, the device comprises: (a) at least a first chamber and at least a second chamber, wherein the first chamber has an inlet for a input of a fluid sample and an outlet at the bottom of the first chamber to output fluid to a valve; and where the second chamber has an inlet for receiving fluid from the valve and an output at the bottom of the chamber; (b) a first channel connecting the output of the first chamber and input of the second chamber; and (c) a first valve housed within the first channel, wherein the first valve comprises a collection reservoir and controls flow of material from the first chamber to the second chamber. In some embodiments, the valve is a metered valve comprising a collection reservoir. In an alternate embodiment, the device can include any number of additional chambers, e.g. a third or more chambers, where each chamber is vertically arranged and each chamber is connected to the adjacent chamber with a channel housing a valve. In some embodiments, the second chamber comprises an outlet to connect to a second channel comprising a second valve, which can connect to one or more additional chambers in a multi-chamber separator/concentrator device as disclosed herein.

In alternative embodiments, the second chamber functions as a collection chamber, and collects the concentrated sample (e.g., the second chamber can be a collection chamber for example, in a 2-chamber device). In such embodiments, the second chamber can be configured as any collection chamber, e.g. any tube, e.g., a 0.2 ml tube, or 0.5 ml tube, or 1.5 ml tube or 2.0 ml or any geometric configuration to collect a concentrated sample, e.g., a collection chamber can be a slide, e.g., microscope slide which comprises in indentation to collect the sample from the outlet of the first channel. In some embodiments, the second chamber, or the lowest chamber (e.g. third, fourth, fifth chamber etc.) which serves as a collection chamber can be removed from the separator/concentrator device after collection of the sample.

In some embodiments, a separator/concentrator device comprising a first and a second chamber, e.g. see FIG. 1A, has the following general mode of operation to transfer the material from the first chamber to the second chamber, requiring three valve operations and sequential centrifuge cycles (herein referred to a "3-valve operation method"):

Step 1: Performing a first valve operation to move the valve to position 3 where the valve is aligned whereby the collection reservoir of the valve is closed to the outlet of the first chamber to prevent the material flow from the first chamber to a second chamber.

Step 2: Adding a fluid sample to be separated into the inlet of the first chamber and performing a first centrifuge cycle. The valve in position 3 obstructs material flow from the outlet of the first chamber into the valve collection reservoir, resulting in material being collected at the bottom of the first chamber during the first centrifuge cycle.

Step 3: Performing a second valve operation to move the valve to position 1, where the collection reservoir in the valve is open and aligned with the outlet of first chamber and performing a second centrifuge cycle. The valve in position 1 results in material being collected in the collection reservoir of the valve during the second centrifuge cycle.

Step 4: Performing a third valve operation to move the valve to position 2, where the collection reservoir in the valve is open and aligned with the inlet of the second chamber and performing a third centrifuge cycle. The valve in position 2 results in the material being transferred from the collection reservoir in the valve to the second chamber during the third centrifuge cycle.

In embodiments comprising more than two chambers, e.g., three chambers, or more than three chambers, particulate material is transferred to each subsequent chamber by repeating the three valve operation and centrifuge cycles steps 1 to 4, with the exception of omitting the addition the fluid sample to the first chamber in step 2.

In an alternative embodiment, a more efficient mode of operation can be used to transfer the material from a first chamber to a second chamber using two valve operations and subsequent centrifuge cycles, e.g. comprising the following steps (herein referred to the "2-valve operation method):

Step 1: Performing a first valve operation to move the valve to position 1, where the collection reservoir in the valve is aligned with the outlet of first chamber.

Step 2: Adding a fluid sample to be separated into the inlet of the first chamber and performing a first centrifuge cycle. The valve in position 1 results in material being collected in the collection reservoir of the valve during the first centrifuge cycle.

Step 3: Performing a second valve operation to move the valve to position 2, where the collection reservoir in the valve is aligned with the inlet of the second chamber and performing a second centrifuge cycle. The valve in position 2 results in the material being transferred from the collection reservoir in the valve to the second chamber during the second centrifuge cycle.

In embodiments comprising more than two chambers, e.g., three chambers, or more than three chambers, particulate material is transferred to each subsequent chamber by repeating the valve operation and centrifuge cycles steps of 1 to 3 of the 2-valve operation method, (with the exception of omitting adding fluid sample to the first chamber), where the valve located between two chambers is operated from position 1 to position 2 after a spin and before a second spin to transfer the particulates from the upper chamber to the lower chamber.

In some embodiments, where a separator/concentrator device comprises multiple chambers, e.g., three, or four, or five or more, each with valves between the chambers, the flow of material from one chamber to the next chamber can be controlled using the same valve operation method, e.g., all valves can be operated using the 3-valve operation method, or all valves can be operated using the more efficient 2-valve operation method, or alternatively in some embodiments, some valves in the device are operated using the 3-valve operation method, and some valves in the same device are operated using the more efficient 2-valve operation method.

Another aspect of the present invention relates to a method for separating particles in a fluid sample, where the fluid sample needing separation is placed in the first (e.g. top) chamber and the separator/concentrator device is centrifuged. In some embodiments, where the valve is in position 1 during a centrifugation cycle, the particulate matter is pelleted/sedimented by the increased gravitational force and settles to the bottom of the first (e.g. top) chamber. In embodiments, where the valve is in position 2 during a centrifugation cycle, the particulate matter is deposited out of the collection reservoir in the valve by the increased gravitational force and enters the input of the second or otherwise downstream chamber. Chamber In some embodiments, the valve can be configured with a collection reservoir to regulate the volume of particles transferred from an upper chamber to a lower chamber. For example, in some embodiments when the valve is operated, e.g., manually or semi-manually, or automatically, such that collection reservoir is positioned to align with an outlet in the upper chamber (e.g. position 1) the valve collection reservoir collects a pre-determined or not predetermined particulate matter during a centrifugation cycle. When the valve is operated, e.g., manually or semi-manually, or automatically, so that the valve collection reservoir is positioned to align with the inlet of the second (or lower) chamber (e.g. position 2), the sedimented particles in the valve collection reservoir are deposited into the second chamber during the centrifuge cycle.

In some embodiments, a separator/concentrator device can comprise at least two chambers, or at least three chambers, and in embodiments where the separator/concentrator has three chambers, the particles can be transferred from the first to the second chamber, and from the second to the third chamber using any combination of the 2- or 3-valve operation methods as disclosed herein.

In the embodiments shown herein, each chamber can be configured to collect particulate matter, e.g. a pellet of material, e.g. the chamber can be configured in a funnel shape to serve to direct the sedimented particles to an outlet at the bottom of the top chamber that leads to the channel connecting to the chamber below.

In the embodiments, the first chamber is designed to hold the volume of the fluid needing separation, the volume can range from 10 nanoliters to 10 L. In some embodiments, a first chamber is designed to hold a volume of between 100 ml and 1 L, or any integer between about 100 ml and 1 L. In one embodiment, the volume can range from about at least 1 ml to about 10 ml, or about at least 10 ml to about 100 ml, or about 100 ml to about 500 ml, or about 500 ml to about 1 L, or about 10 nanoliters to 100 microliters. In other embodiments, the volume can range from 10 microliters to 20 milliliters or any integer between. In some embodiments, the volume can be about 10 ml, or about 100 ml. Any fluid with insoluble particles can be used, e.g. whole blood with blood cells or bacteria, pond/river water with microbes, and urine.

In the embodiments described herein, the first (e.g. top) chamber can be designed to include a wide opening (e.g. input) at the top for ease of fluid input and also comprises a funnel at the bottom of the chamber (see FIG. 7-8) which leads to an outlet connecting to the channel, where the channel is connected to the inlet of the subsequent lower (e.g. second or bottom) chamber.

The sizes and shapes of the chambers and channels can be adjusted accordingly to accommodate to the type of fluid needing separation, the type, volume, and size of particles to be collected, and the desired collection volume.

In one embodiment, the lowest (e.g. second, third or bottom) chamber is smaller than the first (e.g. top or otherwise higher) chambers. In one embodiment, the bottom chamber can contain a wash or suspension solution for collection of the pellet particle. In some embodiments, each chamber can be filled with a collection fluid sample, e.g. a second or third fluid sample, e.g. a buffer or water.

In some embodiments, the lowest (e.g., the second chamber in a 2-chamber device, or a third chamber in a 3-chamber device etc) can function as a collection chamber, and collects the concentrated sample. Such collection chambers typically have an input for receiving a sample but do not have an output for sample outflow. In some embodiments, a collection chamber can be configured as any collection chamber, e.g. any collection tube, e.g., a 0.2 ml tube, or 0.5 ml tube, or 1.5 ml tube or 2.0 ml tube or any geometric configuration of a collection chamber to collect a concentrated sample, e.g., a collection chamber can be a slide, e.g., microscope slide which comprises in indentation to collect the sample from the outlet of the first channel. In some embodiments, the second chamber, or the lowest chamber (e.g. third, fourth, fifth chamber etc. of a multi-chamber device) which is a collection chamber can be removed from the separator/concentrator device after collection of the sample. In some embodiments, a collection chamber is separate from the device, and can be attached to a separator/concentrator device. In some embodiments, e.g., where a device comprises a first chamber and a first valve only, the device can be configured to attach a collection chamber to the lower portion of a 1-chamber, 1-valve device, such that the collection chamber can receive sample from the output of the first chamber, and where fluid transfer into the collection chamber is controlled by the operation of the first valve.

Valve

In some embodiments, the valve is configured to comprise a collection reservoir. In some embodiments, when the valve is in position 1, the valve collection reservoir is in an open position to the inlet of the upper chamber and can receive the particulate material (e.g. pelleted material) from the fluid sample in upper chamber (see FIG. 1A). On valve operation to move the valve to position 2, the valve collection reservoir is in the open position to the inlet of the second (e.g. lower) chamber can deposit the particulate material into the lower chamber.

In some embodiments, valve operation to move the valve from position to position (e.g. from position 3 to position 1, and from position 1 to position 2) can be by sliding the valve, e.g. in a linear motion through the channel, for example, see FIG. 1A. In such embodiments, the valve can comprise a collection reservoir which is configured as a groove in the valve, e.g. as shown in FIGS. 1A and 5.

In alternative embodiments, valve operation to move the valve from position to position can be by a rotational mechanism, e.g. see FIG. 1B. In such embodiments, the valve can comprise a collection reservoir which is configured as a void (e.g. an indentation) in the valve, where the valve can be rotated within the channel to move the valve, e.g. from position 1 to position 2 (e.g. collection reservoir is moved by rotation from being aligned and open to the outlet of the upper chamber to being aligned and open with the inlet of the lower chamber). In such embodiments, where a valve collection reservoir is a void in the valve, e.g. an indentation, the valve is in position 2 also concurrently functions as a valve in position 3 (e.g. where a valve in position 3 is where the valve is closed to the outlet of the upper chamber). In embodiments where valve operation uses a rotational mechanism, the output of the upper chamber and the input of the lower chamber are typically arranged in the same vertical plane (see FIG. 1B).

In some embodiments, valve operation can be in a linear motion such as a pulling or a pushing motion. In other embodiments, valve operation can be in a rotary motion, such as by turning a knob. Valve operation can be by any manual, semi-manual or automatic actuator as disclosed herein.

In some embodiments, valve operation can be manually by or semi-manually, e.g. using a cam sleeve actuation device as disclosed herein. In alternative embodiments, the valve can be operated automatically e.g. using an inertial actuation device as disclosed herein, where the valve is actuated during centrifugation deceleration. In an alternative embodiment, the valve is actuated automatically using an external arm located in a specially adapted centrifuge where the valve is actuated after a complete stop of the centrifuge.

In one embodiment, the valves are moved manually by hand, without the aid of an actuation device, e.g. a semi-manual cam sleeve actuation device or an automatic operation device. In one embodiment, the valves are operated manually by hand with, or without the aid of a tool, e.g., a rod to access the valves in their respective channels. In such an embodiment, the valve is operated manually by hand after the stop of centrifugation.

In one embodiment, the valves are operated semi-manually e.g. using a cam sleeve device as disclosed herein. In alternative embodiments, the valve can be operated using a cam sleeve device which operatively attaches to the disposable separator/concentrator device to operate the valves using a manual rotating mechanism of the cam sleeve device. In one embodiment, valves can be operated by an operatively attached cam sleeve actuation device which is moved manually by hand after the stop of centrifugation.

In one embodiment, the valves can be operated automatically, for example by an operatively attached actuation device, e.g. an inertial actuation device as disclosed herein. In one embodiment, the actuation device uses a piston to operate the valve. In one embodiment, the valves are operated using an inertial actuation device during deceleration in a centrifuge. During deceleration, the inertial actuation device pushes a piston against the valve thereby operating the valve in the channel. Thus, in some embodiments, the valves are moved automatically, for example during centrifugation, for example, during the deceleration phase of the centrifuge cycle. For example, in a three-chambered device where there are two valves, the valves can be moved sequentially, the upper valve being operated during deceleration in a first centrifugation, and the lower valve being operated during deceleration in a second subsequent centrifugation. In some embodiments, the inertial actuation device can be fitted to rotors or buckets to be used in commercially available centrifuges, or in alternative embodiments, the inertial actuation device can be fitted into a purpose-built centrifuge.

In one embodiment, the valves are operated automatically by an actuation device that is part of a purpose-built centrifuge (see, for example FIG. 28). In some embodiments, an actuation device can be any mechanism for actuating the valves, for example, where the mechanism includes, but is not limited to, motors, solenoids, pumps, mechanical pumps, levers, air cylinder actuation devices as disclosed herein, which have an external arm which operates the valves in the disposable separator/concentrator device. In such an embodiment, at least one separator/concentrator device is placed in the rotor of a purpose-built centrifuge such that a centrifuge-attached actuation device, e.g. an external arm of the mechanical actuation device can engage the valve of the disposable separator/concentrator device during or after each centrifuge cycle. In such embodiments, the valve is operated automatically using the centrifuge-attached mechanism. In some embodiments, the valves are moved automatically, for example, where the separator/concentrator device has come to a stop after a centrifuge cycle and is positioned in a location in the centrifuge to be engaged by an external arm of the mechanical actuation device for operation of one or more of the valves. For example, in a three-chambered device where there are two valves, the valves can be operated sequentially, the upper valve can be operated after completion of the first centrifuge cycle, and the lower valve can be operated after a subsequent centrifuge cycle.

In one embodiment, the valve comprises a collection reservoir, which is operated to move within a channel connecting two chambers to allow a defined volume from the chamber above the valve to be transferred into the chamber below the valve. The volume which is transferred is determined by the volume of the valve collection reservoir, and can be any amount depending on the type, volume, quantity and size of particles to be collected, and the desired collection volume. For example, the volume of the valve collection reservoir, and thus the volume which is transferred between chambers can range from about at least 10 nanoliters to 10 milliliters. The volume transferred between chambers can be predetermined if a metered valve is used, e.g. a valve with a metered groove collection reservoir or a metered void collection reservoir, where the collection reservoir allows the transfer of at least 10 nl, or more, for example, about 5 µl, or about 10 µl or about 100 µl or about 1 ml, or about 2 ml, or between 2 ml and 10 ml, or any integer between 10 nl and 10 ml. In some embodiments, the volume amount is generally determined by the volume of the collection reservoir present in the valve, which receives collected sample from the upper chamber (e.g. when the valve is in position 1) and which subsequently dispenses the collected sample volume (in the collection reservoir) into the lower chamber (e.g., when the valve is in position 2).

The system according to the invention provides a system for separation and concentration of particulates from a fluid sample by centrifugation, comprising: (a) a first chamber and a second chamber, where the first chamber has an inlet opening for fluid sample application, and an outlet which connects the a channel, and the second chamber having an inlet connecting to a channel, (b) a valve in the channel connecting the chambers; and (b) a centrifuge. Another embodiment of a separation system comprises a separation/concentrator device described herein, a valve actuation device to operate the valves, e.g. a semi-manual actuator such as a cam sleeve actuation device, or an automatic actuator, e.g., an inertial actuator device. In some embodiments the system also comprises a centrifuge. In one embodiment, the valve operation device is an automatic valve operation device, e.g., an inertial actuator device.

Also embodied herein is a method of separation and concentration of particulates from a fluid sample by centrifugation comprising (a) inserting a fluid sample into a first chamber of a multi-chamber separating device; (b) centrifuging the fluid sample in the first chamber causing the particulates to separate from the fluid sample and accumulate in the first chamber; (c) operating a valve to allow at least a portion of the accumulated particulates in the first chamber to flow into a second chamber; and (d) centrifuging the accumulated particulates in the second chamber to cause the particulates to further separate from the fluid sample and accumulate in the second chamber.

In another embodiment, embodied herein is a method of separation and concentration of particulates from a fluid sample by centrifugation comprising; (a) providing a device having a first chamber connected to a second chamber by a channel, the channel including a valve that can prevent material from flowing between the first chamber and the second chamber; (b) introducing a fluid sample containing particulates into the first chamber (c) centrifuging the device for a predefined time, causing the particulates to separate from the fluid sample and accumulate near an outlet of the first chamber; (d) operating a valve to enable the movement of the separated particulates from the first chamber to the second chamber; (e) centrifuging the device for a predefined time, causing the particulates to further separate from the fluid sample and accumulate near an outlet of the second chamber.

Another method for separating particles with the separator/concentrator device as disclosed herein comprises (a) introducing a fluid sample containing particulates into a first chamber of a disposable separator/concentrator device, wherein the first chamber has an inlet for receiving a sample and wherein the first chamber connects to a second chamber via a channel, and wherein the channel comprises a valve; centrifuging the separation system in a centrifuge; wherein the valves can be operated, e.g. using manual operation, e.g., by hand, or using semi-manual operation, e.g., using a cam actuation sleeve device as disclosed herein, or by automatic operation, e.g., using an inertial actuation device during deceleration, or an external arm which engages the valves, where the external arms are part of a centrifuge attached mechanism of in a purpose-built centrifuge, thus allowing a pre-defined volume from the first chamber into the second chamber; (b) allowing the separation system to decelerate to a complete stop in the centrifuge; and (c) and collecting the particulates from the second chamber of the separation system.

Embodied herein are devices for valve operation, e.g. valve operating devices, e.g. a semi manual cam sleeve actuation device, or an automatic inertial actuation device which can be use with centrifugation.

Embodied herein is an automated actuation device, e.g. inertial actuation device that arms during centrifugal acceleration and actuates during centrifugal acceleration comprising a casing 209 housing a swing arm 201, a torsion spring 202, a non-movable shaft 203, a latch 204 on the swing arm 201, and a movable actuator 206 mounted on the casing 209, wherein the swing arm 201 rotationally attached to the torsion spring 202 and also rotationally attached to the non-movable shaft 203 mounted on the casing 209, wherein the swing arm swings pivotally from the shaft when experiencing variable centrifugal force during centrifugal acceleration and deceleration, wherein the swing arm 201 rotational pivot off the shaft 203 compresses the torsion spring 202 during centrifugal acceleration, wherein release of compressed energy from the torsion spring 202 during centrifugal deceleration rotates the swing arm 201, wherein the latch 204 is retractable, is retracted during centrifugal acceleration and becomes extended during and when top centrifugation speed is attained, wherein the movable actuator 206 is juxtapose to the swing arm 201 and makes contact with the latch 204 of the swing arm during deceleration, the latch 204 being in the extended state after top centrifugation speed and during deceleration, wherein the movable actuator 206 is moved by a recoil swing/rotation of the swing arm 201 through contact with the extended latch 204 during deceleration.

The movable actuator 206 present on the inertial actuator device can move the valve in a linear motion such as a pulling or a pushing motion. Alternatively, the movable actuator 206 on the inertial actuator device can be moved in a rotational motion. The movable actuator 106 can be a valve actuator, e.g. a piston valve actuator. The valve actuator comprises a compression spring or torsion spring.

One embodiment of the automated actuation device comprises a piston valve actuator comprising a head 205, a light compression spring 207 and a piston 208, wherein the head 205 is connect to the piston 208, wherein the light compression spring 207 encases a piston 208, wherein the head 205 juxtapose to the swing arm 201.

Another embodiment of the automated inertial actuator device is one comprising a top swing arm 201, a bottom swing arm 212, a top movable actuator 206 and a bottom movable actuator 213, wherein each swing arms has a retractable latch 204, wherein one swing arm and latch contacts to one movable actuator, wherein the swing arms and corresponding movable actuators are arranged vertically, one on top of another.

One embodiment of the automated inertial actuator device has two swing arms and two corresponding movable actuators comprises a movable latch stop 211, wherein the latch stop 211 is in contact with the bottom movable actuator 213.

One embodiment of the automated inertial actuator device has two swing arms and two corresponding movable actuators comprises a latch stop release 210, wherein the latch stop release 210 is in contact with the top movable actuator 206 at one end and in contact with the latch stop 211 at the other end, and wherein the actuation of the top movable actuator 206 disengages the latch stop 211 away from the bottom movable actuator 213.

BRIEF DESCRIPTION OF THE DRAWINGS

FIG. 1A shows an embodiment of valve operation from position 1, 2 and 3 using linear motion to transfer material using a valve comprising a groove collection reservoir from an upper chamber to the lower chamber. FIG. 1B shows an embodiment of valve operation from position 1, 2 and 3 using rotational mechanism to transfer material using a valve comprising a void collection reservoir in the valve from an upper chamber to the lower chamber. FIG. 1C shows an embodiment of valve operation from position 1, 2 and 3 using a combination of rotational valve and linear motion to transfer material using a valve comprising a rotatable groove collection reservoir from an upper chamber to the lower chamber. FIG. 1D is a perspective view of one embodiment of a separator/concentrator device comprising two chambers, a top chamber 101 and a bottom chamber 103 and one valve 111 within a channel 113 for the separation, concentration and collection of particulates from a fluid sample before centrifugation. FIG. 1E is a perspective view of the separator/concentrator device in FIG. 1D after centrifugation when the valve 111 has been moved within a channel 113 in the indicated direction during deceleration or after the centrifugation cycle.

FIG. 4A is another prototype picture of a separator/concentrator. FIG. 4A shows the separator/concentrator with a semi-manual valve actuator which is a cam sleeve actuator device 400 to operate the valves, also shown in FIG. 26. FIG. 4B shows the cross sectional view of FIG. 4A. FIG. 4C shows the first valve 111 and second valve 112 in position 1. FIG. 4D shows the first valve 111 in position 2 allowing fluid collected in the valve collection reservoir from the first chamber 101 to transfer to the second chamber 103. FIG. 4E shows the second valve 112 in position 2 allowing fluid collected in the valve collection reservoir from the second chamber 103 to transfer to the third chamber 105.

FIG. 6A shows the metered valve in its initial position to collect sample from the upper chamber during the first or second centrifuge cycle. FIG. 6B shows the metered valve in its final position during the subsequent or second centrifuge cycle allowing the sample to pass into the lower chamber. The embodied metered valve alone is shown in FIG. 5. In this embodiment, the distance between the chambers is 0.400 inch.

FIG. 7A shows a cut-away image of the separator/concentrator device. FIG. 7B shows a three-dimensional solid shell image of the separator/concentrator device. The design of this embodiment incorporates three successively smaller chambers and two valve systems.

FIG. 9A shows a front, transparent view of one embodiment of the separator/concentrator device. FIG. 9B shows a three dimensional transparent perspective view from a top angle of one embodiment of the separator/concentrator device. Note a perspective view and a prototype picture of the embodied separator/concentrator device are shown in FIG. 3.

FIG. 10A is a perspective view of an embodiment of an actuation device comprising a swing arm 201 attached to a torsion spring 202, a retractable latch 204 that is on the swing arm 201 that rotates around the axis of rotation 203. FIG. 10B is a perspective view of the actuation device of FIG. 10A where the latch 204 contacts and pushes a moveable actuator 206 when the arm recoils in the indicated direction. FIG. 10C is a perspective view of an embodiment of the actuation device of FIG. 10A comprising a moveable actuator for rotational motion. FIG. 10D is a perspective view of one embodiment of the actuation device of FIG. 10A comprising a moveable actuator for linear pulling motion. FIG. 10E is a perspective view of one embodiment of the actuation device of FIG. 10A comprising a moveable actuator for linear pushing motion.

FIG. 11A is a perspective view of FIG. 10E when the actuator device is at resting state before start of centrifugation. FIGS. 11B and 11C are perspective views of FIG. 10E during centrifuge acceleration when the latch 204 of the actuator device is retracted. FIG. 11D is a perspective view of FIG. 10E at centrifuge top speed where the latch 204 is extended. FIGS. 11E and 11F are perspective views of FIG. 10E during centrifuge deceleration when the latch 204 catches and extends (pushes) piston 208.

FIG. 12A shows the swing arm, a torsion spring (not shown) is attached to the arm and to the top fixed wall. FIG. 12A shows the position of the swing arm at during acceleration of the centrifuge cycle, where when the high gravitational force reaches a certain level, e.g. 3000 G, the swing arm swings away from the valve. FIG. 12B shows the position of the swing arm at during deceleration of the centrifuge cycle, where when the gravitational force reaches a certain lower gravitational force level, e.g. less than about 1500 G, the swing arm swings away towards the valve in the separator/concentrator device. In the embodiment shown in FIGS. 12 and 12B, the inertial actuator device is designed to actuate the valve with a piston. The piston of the actuator used to push the valve is shown in FIG. 12B.

FIG. 14A shows a three dimensional transparent prospective view the separator/concentrator device 319 configured such that the valves in the separator/concentrator device can be actuated by piston valve actuators 317 of an actuation device, e.g. an automatic inertial actuation device 317. The FIG. 14B shows the a two dimensional top view of the separator/concentrator device 319 of FIG. 14A, showing the separator/concentrator device 319 configured such that the valves in the separator/concentrator device can be actuated by piston valve actuators 317 of an actuation device, e.g. an automatic inertial actuation device 317. FIG. 14C shows a picture of one embodiment of the separator/concentrator device 319 configured such that the valves in the separator/concentrator device can be actuated by movable actuators 206 (not shown) of an automatic actuation device, e.g. an automatic inertial actuation device 317.

FIGS. 16A-E illustrate the use of the embodiment of FIG. 15. FIGS. 16A and 16B are perspective views of FIG. 15 shows the latch stop prevents the second latch from extending during the first centrifuge. FIG. 16C is a perspective view of FIG. 15 showing the latch stop release 210 shifts the latch stop 211 backwards during first centrifuge deceleration. FIG. 16D is a perspective view of FIG. 15 showing the second latch extension during second centrifuge top speed. FIG. 16E is a perspective view of FIG. 15 showing the second latch catches and extends second bottom piston during second centrifuge deceleration.

FIG. 17A is a perspective view of FIG. 13 showing actuation unit and separation unit during first centrifuge acceleration. FIG. 17B is a perspective view of FIG. 13 showing first valve actuating during first deceleration. FIG. 17C is a perspective view of FIG. 13 showing during second centrifuge acceleration. FIG. 17D is a perspective view of FIG. 13 showing second valve actuating during second deceleration and final valve positions.

FIG. 18A shows the torsion spring constant versus angle for acceleration, and FIG. 18B shows the torsion spring constant versus angle during deceleration.

FIG. 25 is a SERS spectrum obtained for the control E. coli sample (top trace) and SERS spectrum obtained from the output of the initial prototype (bottom trace) from a sample of water spiked with approximately 1E9 cfu/mL E. coli. The shapes of the two spectra are very similar.

FIG. 26 shows the cam sleeve actuator device for actuating two valves of a separator/concentrator device, where the cam sleeve actuator device 400 has an upper first cam 401 (cam 1) configured to operate a first valve in the separator/concentrator device, and a second cam 410 (cam 2) configured to operate a second valve in the separator/concentrator device. Also shown are stop tabs 402, 403, 405, in the same plane as the first cam 401 to control the operation of the valves and rotation of the cam sleeve about the channels.

FIG. 27A shows the location of a first and second valve 111 in a first and second channel of the separator/concentrator device, where the orientation of the cam sleeve actuator device during a first centrifugation allows the first valve and second valve to be in position 1. After a first centrifuge cycle, the cam sleeve actuator device 400 is rotated in an anti-clockwise orientation to so the first cam 401 moves the first valve 111 into position 2 as shown in FIG. 27B. FIG. 27B shows the first cam 401 has connected and actuated the first valve 111 to move it from position 1 to position 2, where the first cam has moved the valve along the axis of the first channel away from the first cam 401, and the lower valve has not been actuated (the lower valve remains in position 1). The cam sleeve actuator device can not be rotated in a clockwise direction as the valve 111 contacts the stop tab 405, and thus can only be rotated a counter-clockwise direction. Further, the cam sleeve actuator device can only be rotated a certain distance in an counter-clockwise direction before the first valve 111 contacts the stop tab 402 preventing further counter-clockwise rotation of the cam sleeve actuator. It is in this configuration the second centrifuge cycle occurs. After the second centrifuge cycle the cam sleeve actuator device 400 is rotated in a clockwise orientation to move the lower (e.g. second) valve from position 1 as shown in FIG. 27B to position 2 as shown in FIG. 27C.

FIG. 31A-31B are schematic diagrams of free body and force analysis diagrams of valve actuation for accelerating and decelerating motion. FIG. 31A shows the force analysis of accelerating motion, with the arm swinging down. FIG. 31B shows the force analysis for decelerating motion, with the arm swing up for actuating the valve.

DETAILED DESCRIPTION OF THE INVENTION

The invention embodied herein relates to a particle separation, in particular, a device for concentration and separation of particles, e.g., bacteria or contaminants, from a fluid sample. The separation/concentration of particles in a sample is achieved by sequential centrifugation steps using a separator/concentrator device, such as disposable separator/concentrator device.

In some embodiments, the separator/concentrator device is useful for the extraction and concentration of particles from a fluid sample, e.g., bacteria or particles from a biological sample, e.g., a blood or other biological sample, where the concentrated or separated particles can be used for subsequent analysis, e.g. downstream clinical diagnostics and detection, e.g. PCR, bioMEMS devices, etc.

In one embodiment, the invention is directed to a disposable particle concentration device, herein referred to a "separator/concentrator" device, where particle separation occurs in multiple centrifugation steps, where the sample is passed from one chamber to another chamber within a disposable device during sequential centrifugation steps. The chambers are connected via a channel comprising a valve, and the flow of the sample from one chamber to another is controlled by a valve located in the channel connecting each chamber. The valve can be operated by any a variety of different ways, for example, manually, semi-manually, semi-automatically or automatically, as disclosed herein.

In some embodiments, a separator/concentrator device, e.g., a disposable separator/concentrator device comprises: (a) at least a first chamber and at least a second chamber, wherein the first chamber has an upper inlet for a input of a fluid sample and an lower outlet at the bottom of the first chamber to output fluid to a valve; and where the second chamber has an upper inlet for receiving fluid from the valve and a lower output at the bottom of the chamber; (b) a first channel connecting the output of the first chamber and input of the second chamber; and (c) a first valve housed within the first channel, wherein the first valve comprises a collection reservoir and controls flow of material from the first chamber to the second chamber. In some embodiments, the valve is a metered valve comprising a collection reservoir. In an alternate embodiment, the device can include any number of additional chambers, e.g. a third or more chambers, where each chamber is vertically arranged and each chamber is connected to the adjacent chamber with a channel housing a valve.

Figure 1A:
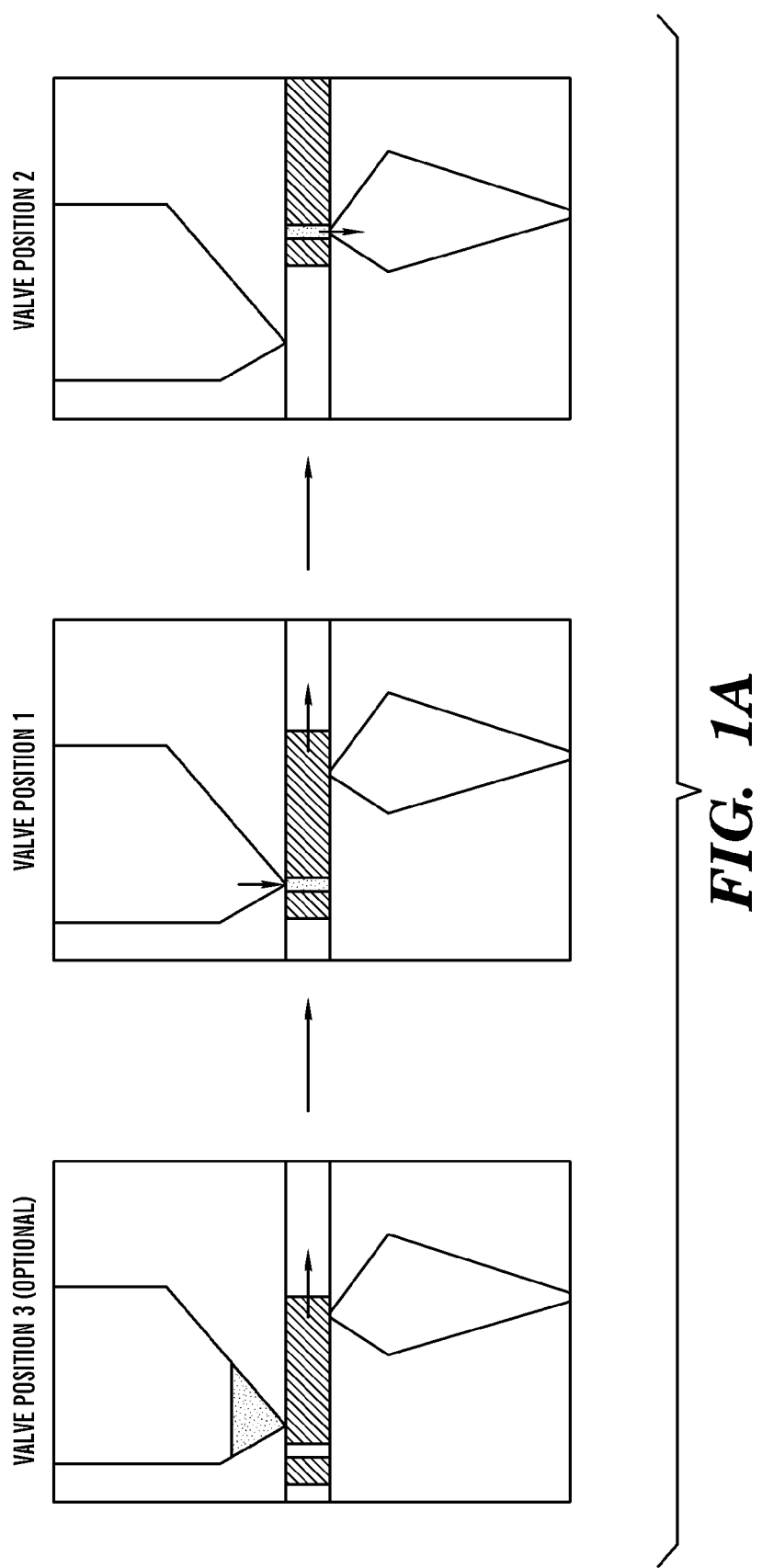
FIGS. 1A-1E show perspective view of the disposable separator/concentrator device.

In some embodiments, the valve can be operated, e.g., manually, or semi-manually or automatically to be in one of three different positions, as shown in FIG. 1A. For example, when the valve is operated to be in a first position (e.g. position 1), the collection reservoir in the valve collects sample from the first channel. The valve is operated to be in a second position (e.g. position 2) the collection reservoir in the valve deposits any collected sample from the first channel into the second chamber. Optionally and in some embodiments, before being operated into the first position, the valve can be operated to be in a third position (e.g. position 3) which is where the valve collection reservoir is closed the first chamber, thus preventing sample collecting in the collection reservoir, and therefore when the sample is centrifuged, the particulates collect at the output of the first chamber, ready to enter the valve collection reservoir when the valve is operated into position 2.

Thus, in some embodiments, the method to transfer the material from the first chamber to the second chamber requires a 3-valve operation method to operate the valves in the separator/concentrator device, the method comprising;

Step 1: Performing a first valve operation to move the valve to position 3 where the valve is aligned where the collection reservoir of the valve is closed to the outlet of the first chamber to prevent the material flow from the first chamber to a second chamber.

Step 2: Adding a fluid sample to be separated into the inlet of the first chamber and performing a first centrifuge cycle. The valve in position 3 obstructs material flow from the outlet of the first chamber into the valve collection reservoir, resulting in material being collected at the bottom of the first chamber during the first centrifuge cycle.

Step 3: Performing a second valve operation to move the valve to position 1, where the collection reservoir in the valve is open and aligned with the outlet of first chamber and performing a second centrifuge cycle. The valve in position 1 results in material being collected in the collection reservoir of the valve during the second centrifuge cycle.

Step 4: Performing a third valve operation to move the valve to position 2, where the collection reservoir in the valve is open and aligned with the inlet of the second chamber and performing a third centrifuge cycle. The valve in position 2 results in the material being transferred from the collection reservoir in the valve to the second chamber during the third centrifuge cycle.

In some embodiments, the method to transfer the material from the first chamber to the second chamber encompasses a more efficient 2-valve operation method to operate the valves in the separator/concentrator device, the method comprising;

Step 1: Adding a fluid sample to be separated into the inlet of the first chamber Step 2: Performing a first valve operation to move the valve to position 1, where the collection reservoir in the valve is aligned with the outlet of first chamber and performing a first centrifuge cycle. The valve in position 1 results in material being collected in the collection reservoir of the valve during the first centrifuge cycle.

Step 3: Performing a second valve operation to move the valve to position 2, where the collection reservoir in the valve is aligned with the inlet of the second chamber and performing a second centrifuge cycle. The valve in position 2 results in the material being transferred from the collection reservoir in the valve to the second chamber during the second centrifuge cycle. This process of valve operation from position 1 to position 2 can be repeated on any number of valves that separate an upper and a lower chamber to allow the sample to be transferred from an upper chamber to a lower chamber.

In some embodiments, a valve can be operated to move the valve from a position 1 to position 2 in a linear motion along the channel, such as a pulling (e.g., See FIG. 1A) or a pushing motion. In some embodiments, a valve can be configured with a helical screw-like mechanism which connects with the channel so that the valve can be operated so that rotation of the valve will move the valve in a linear direction from position 1 to position 2. In other embodiments, the valve can be operated by a rotational movement to rotate the valve from position 1 to position 2, e.g. see FIG. 1B.

The valve can be operated by any manual, semi-manual or automatic actuator as disclosed herein.

In some embodiments, the valve can be operated manually, for example by hand, where the valve is pushed in, or pulled out, by any means known to one of ordinary skill in the art. In one embodiment, the valves are operated by hand, without the aid of an operatively attached actuation device. In one embodiment, the valves are operated by hand without the aid of a rod to access the valves in their respective channels. In such an embodiment, a valve can be operated manually by hand after the stop of centrifugation.

In another embodiment, the valve can be operated semi-manually, e.g. using a cam sleeve actuator device as disclosed herein. In such embodiments, the valve can be operated using a cam sleeve device which attaches to the disposable separator/concentrator to operate the valves, where valves are operated by a manual rotation of the cam sleeve device which fits, e.g. transverse to the axis of the channels and valves. In other embodiments, other semi-manual actuation devices can be used to operate the valves, for example, sleeves which allow the valve to be operated using a lip-stick actuation device commonly known by persons of ordinary skill in the art. In some embodiments, a valve can be operated manually using a cam sleeve actuation device, or another semi-manual actuation device after the stop of centrifugation. As the valve operation requires manual operation of an attached valve operation device, e.g., a cam sleeve actuator device as disclosed herein, this valve operation is referred to herein as "semi-manual" valve operation.

In another embodiment, the valve can be operated automatically e.g. using an inertial actuation device as disclosed herein, where the valve operation occurs during centrifugation deceleration. During deceleration, the inertial actuation device pushes a piston against the valve thereby operating the valve in the channel. In some embodiments, the inertial actuation device can be fitted to rotors or buckets to be used in commercially available centrifuges, or in alternative embodiments, the inertial actuation device can be fitted into a purpose-built centrifuge.

Figure 28:
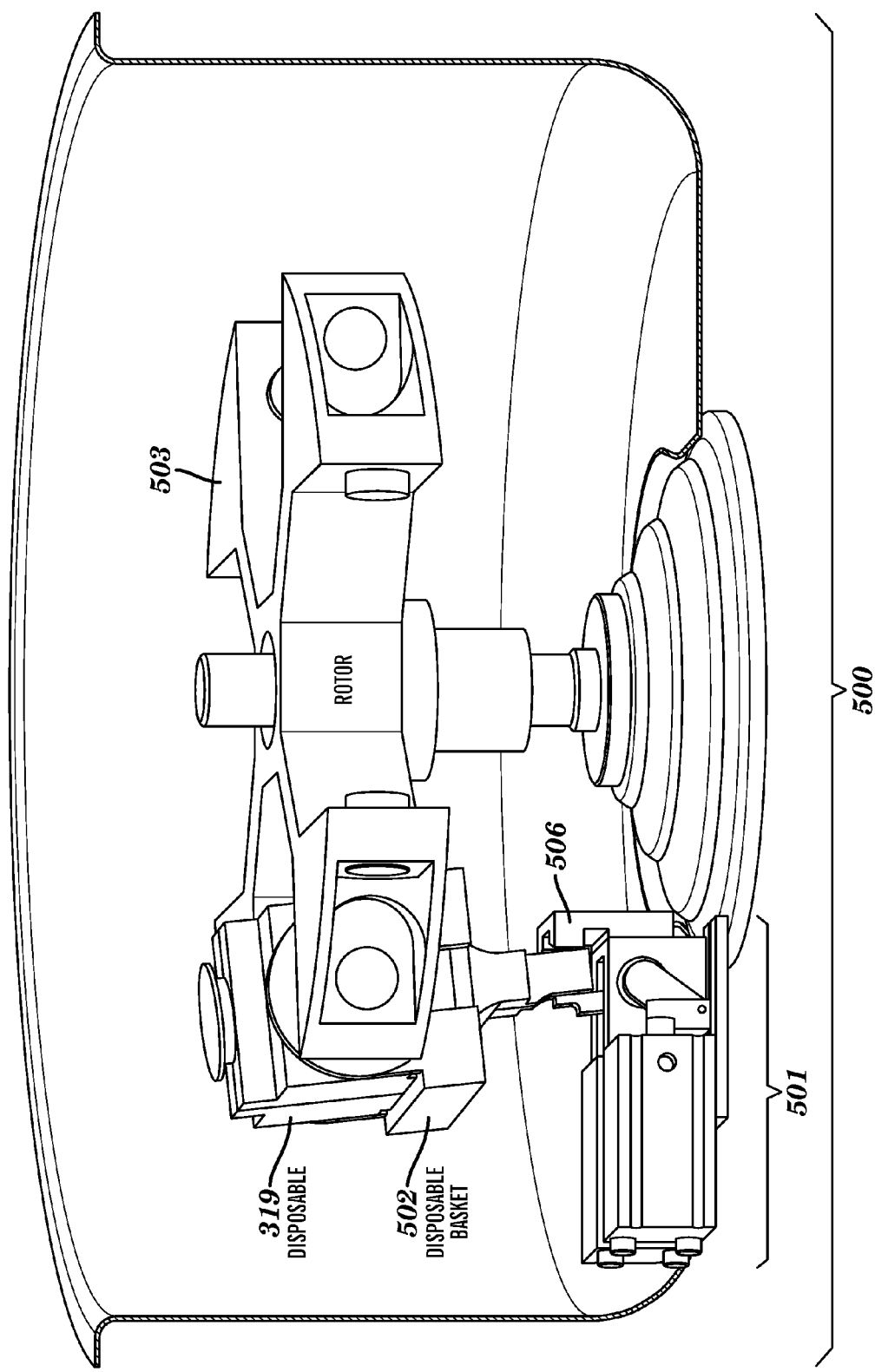
FIG. 28 shows an embodiment of actuation of the valve using an automatic actuator in a purpose-built centrifuge. The separator/concentrator 319 is placed in basket or holder 502 of the rotor of a purpose-built centrifuge 500, and the automatic actuator 501 is attached to the bottom of the purpose-built centrifuge where the automatic actuator 501 comprises external arms (not shown) which are configured to operatively connect to actuate the valves of the separator/concentrator. After each centrifuge cycle, the centrifuge is programmed to stop the basket holding the separator/concentrator 319 in a location so the external arms of the automatic actuator can actuate the appropriate valves in the separation/concentration process. In some embodiments, the purpose-built centrifuge can comprise one or more automatic actuators 501.

In an alternative embodiment, a valve is operated automatically using a mechanical external arm which is located in a specially adapted or purpose-built centrifuge, where valve operation occurs after a complete stop of the centrifuge (see, for example FIG. 28). In some embodiments, an external arm which operates the valves in a purpose-built centrifuge can be any mechanism for operating the valves, for example, where the mechanism includes, but is not limited to, motors, solenoids, pumps, mechanical pumps, levers, air cylinder actuation devices as disclosed herein, where an external arm comes into contact and operates at least one valve in at least one disposable separator/concentrator device in the centrifuge when the centrifuge cycle has come to a stop. In such an embodiment, at least one separator/concentrator device is placed in the purpose-built centrifuge such that an external arm which operates the valve (e.g. as part of a centrifuge-attached actuation device) can engage with a separator/concentrator device after each centrifuge cycle and operate the valve(s). In such embodiments, valve operation occurs automatically by a mechanism which moves the external arm to contact the valves. In some embodiments, valve operation occurs automatically, for example after centrifugation, e.g. when the separator/concentrator device has come to a stop after the centrifuge cycle and positioned to be in a location in the centrifuge such that the external arm of the mechanically operated actuation device can engage and operate the valves. For example, in a three-chambered device comprising two valves, each valve is are moved sequentially, e.g. the first valve is moved from position 1 to position 2 after completion of a centrifuge cycle and then the second valve is moved from position 1 to position 2 after a subsequent centrifugation.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

DEFINITIONS OF TERMS

Unless otherwise explained, all technical and scientific terms used herein have the same meaning as commonly understood by one of ordinary skill in the art to which this disclosure belongs.

As used herein, the term "fluid sample" means any aqueous solution, e.g. water, pond water, stagnant water (e.g., in a clinical or laboratory apparatus, such as an incubator), bodily fluids such as urine, whole blood, serum, cerebrospinal fluid, and a liquid cell culture or a suspension of cells in culture media.

As used herein, the term "particulate" refers to particles of solid, insoluble matter suspended in a liquid. For example, blood cells or bacteria suspended in blood. In pond water, particulates include bacteria and other microorganisms, dust, and decaying vegetation. Particulates, alternatively referred to as particulate matter (PM) or fine particles, are tiny subdivisions of solid suspended in liquid. In some embodiments, particulates are bacteria, of any shape (e.g. spherical, e.g., cocci, or rod-shaped, e.g., *bacilli*) and size or morphology. Bacterial cells typically about one tenth the size of a eukaryotic cell, and range typically between about 0.5-5.0 micrometers in length. In some embodiments, the particulates are ultramicrobacteria, which are bacteria that are considerably smaller than normal bacterial cells, and are about 0.3 to 0.2 micrometers in diameter, e.g., cocci found in seawater that are less than 0.3 µm in diameter. In some embodiments, the particulates are nanobacteria also referred to as "calcifying nanoparticles", which were living organisms that were 0.1 µm in diameter. In some embodiments, the particulates are L-form bacteria, also known as L-phase bacteria, L-phase variants or cell wall deficient (CWD) bacteria, which are strains of bacteria that lack cell walls. L-forms can be generated in the laboratory from many bacterial species that usually have cell walls, such as *Bacillus subtilis* or *Escherichia coli*.

In other embodiments, the particulate can be any pathogen, e.g. virus, fungus, algae (e.g. single cell algae), bacteria and the like. Particulates that are viruses can be any virus with a typical range between 20-300 nanometers in length. Pathogenic viruses include, for example but are not limited to, viruses from families of: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae. Some notable pathogenic viruses cause: smallpox, influenza, mumps, measles, chickenpox, ebola, and rubella. Particulates that are bacteria can be any bacteria with a typical range between 1-5 micrometers. Pathogenic bacteria include, for example but are not limited to, pathogenic bacteria such as *Mycobacterium tuberculosis, Streptococcus* and *Pseudomonas, Shigella, Campylobacter* and *Salmonella*. Pathogenic bacteria also cause infections such as tetanus, typhoid fever, diphtheria, syphilis and leprosy. Particulates that are fungi can be any bacteria with a typical range between 1-40 micrometer in length. Fungal pathogens comprise a eukaryotic kingdom of microbes that are usually saprophytes but can cause diseases in humans, animals and plants. Fungi are the most common cause of diseases in crops and other plants. Fungi are common problems in the immunocompetent population as the causative agents of skin, nail or yeast infections.

As used herein, the term "material" as used herein in reference to transfer of material from one chamber to another refers an admixture or combination of particles and insoluble matter, e.g. cell organelles, cell membranes etc., and a small volume of sample fluid. The size of the particles in the material transferred to the next chamber is dependent on the duration and the speed of the centrifuge cycle. For example, depending on the centrifuge cycle, the material can comprise an admixture comprising particles, e.g., bacterial cells and a small volume of the fluid supernatant. Stated another way, the "material" is a combination of particulates from the fluid sample and small volume of supernatant, where the supernatant is preferably v/w less than 1%, or less than 2%, or less than about 5% or less than about 10% or less than about 20% or less than about 30%, or less than about 50% or less than about 60% or less than about 70% or less than about 80% or less than about 90% of the total material volume. In some embodiment, the material comprises an amount of particulates which is at least about 1% or at least about 10%, or at least about 20% or at least about 30%, or at least about 40%, or at least about 50%, or at least about 60%, or at least about 70%, or at least about 80%, or at least about 90%, or at least about 95%, or at least about 98% of the total material volume (w/v). In some embodiments, the amount of particulates any integer between about 1 and 100% of the total material volume. In some embodiments, the particulates comprise 90-99% of the material volume.

As used herein, the term "valve" with respect to the separator/concentrator device described herein refers to a valve that seals, blocks, and moves within the channel connecting the chambers in the device. The movement of the valve within the channel controls the flow of materials from the chamber above the valve to the chamber below the valve.

As used herein, the term "physically separated" with respect to the chambers in the separator/concentrator device means that the chambers are not directly next to and connected with each other.

As used herein, the term "operatively attached" with respect to the valve actuator and the separator/concentrator device means that the valve actuator is physically attached and orientated to the separation device in such way that allows the valve actuator to access and actuate the valves in the separator/concentrator device.

As used herein, the term "purpose-built" centrifuge refers to a custom made centrifuge which is specially adapted to be used with the disposable devices as disclosed herein, and where the purpose-built centrifuge comprises an automatic actuating device to operate the valves in the separator/concentrator device between each spin cycle.

As used herein, the term "actuation device" refers to a device that moves the valves described herein.

As used herein, the term "arm" with respect to the inertial actuator device refers to swings harnessing the force generated during centrifugation to perform actions upon centrifugation deceleration. The swing arms rotate/swing away in the opposite direction from the valve of the separator/concentrator device (see FIG. 11) during acceleration (e.g. an increase in speed) in centrifugation. Stated another way, due to the centrifugal forces during centrifugation, the swing arms move in the opposite direction from the center of the rotational force.

As used herein, the term "a centrifugation cycle" with respect to a centrifuge means an acceleration of the centrifuge to reach the fixed pre-defined gravitational force setting, maintenance of the centrifugal force setting for a pre-determined fixed time, followed by a deceleration of the centrifuge at the end of the fixed time to a final stop.

Other than in the operating examples, or where otherwise indicated, all numbers expressing quantities of ingredients or reaction conditions used herein should be understood as modified in all instances by the term "about." The term "about" when used in connection with percentages may mean ±5%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "comprising" means that other elements can also be present in addition to the defined elements presented. The use of "comprising" indicates inclusion rather than limitation.

Separator/Concentrator Device—General Principals

Embodiments of the invention are directed to a separator/concentrator device, a separation system and methods for separation and concentration of particulates from a fluid sample using centrifugation.

One aspect of the present invention relates to a separator/concentrator device, such as a disposable separator concentrator device comprising at least two chambers, e.g. a first chamber and second chamber, where fluid flow between the chambers is controlled by a valve. Valve operation can be by any means, e.g. by manual operation, semi-manual operation, or by automatic operation, as disclosed herein. The valve allows a specific volume of fluid sample to be passed from one chamber to another chamber when the valve is operated from a first position to a second position in the channel of the separator/concentrator device. The volume of fluid transferred to one chamber to the next can comprise particulate matter, e.g. particulate matter from a pellet of any solid particulate matter of interest, e.g. a pellet of cells, e.g., blood cells, bacteria cells, platelets, water contaminants, e.g. pond water sediments and the like. FIGS. 1A-1C and FIG. 2 and FIG. 4 show the sequential steps of moving the valves in order to collect the concentrated particulate matter.

Figure 1B:
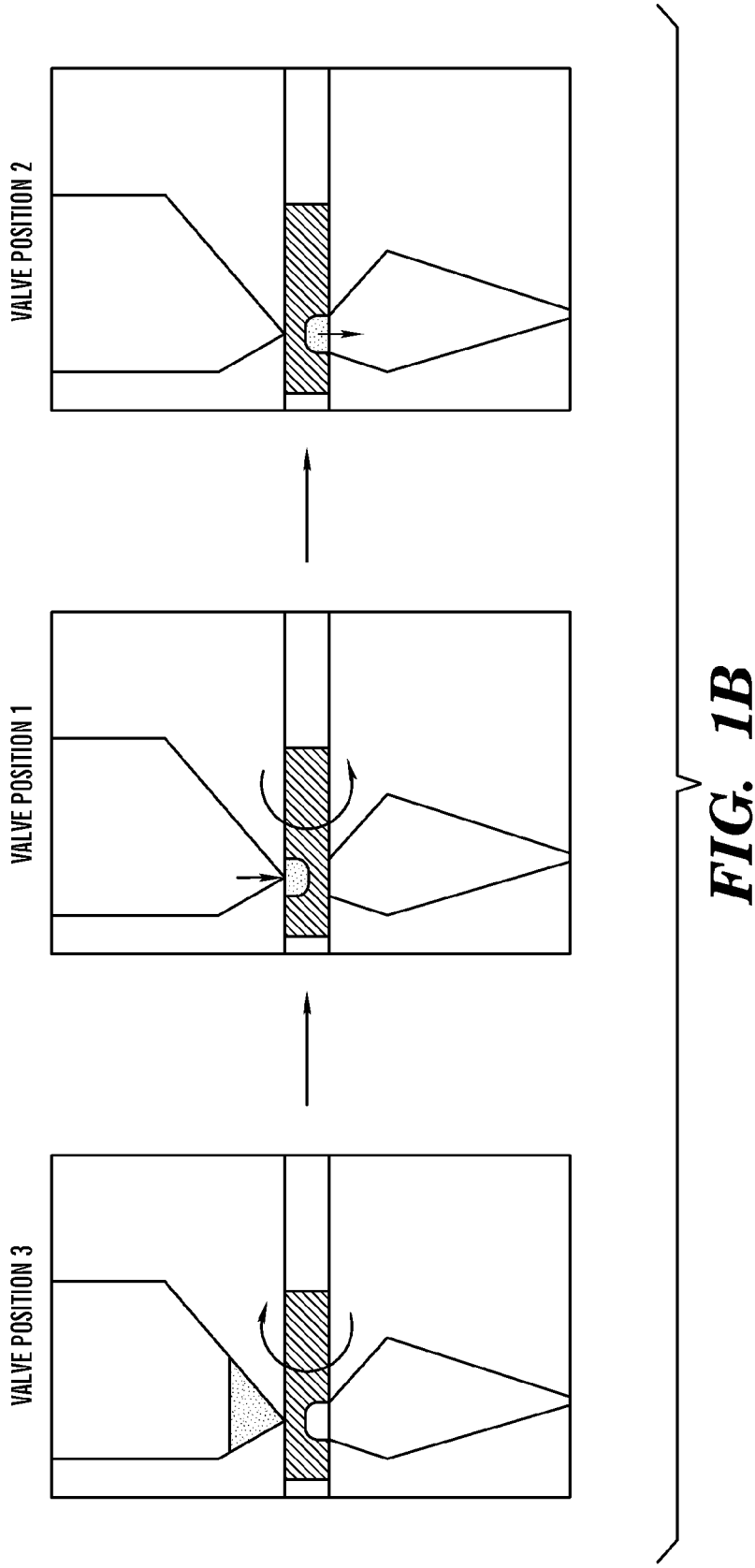
Figure 1C:
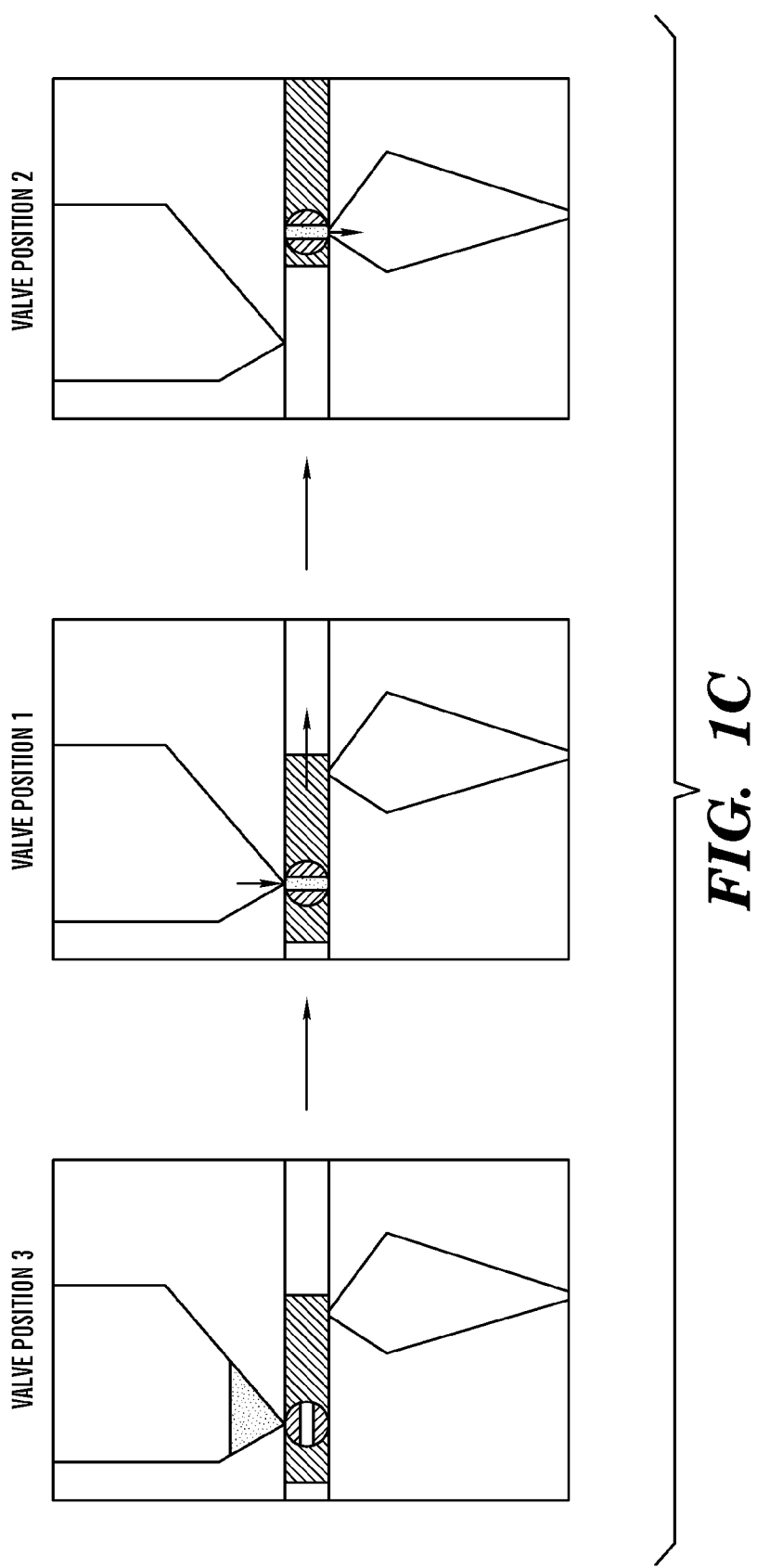
Figure 1E:
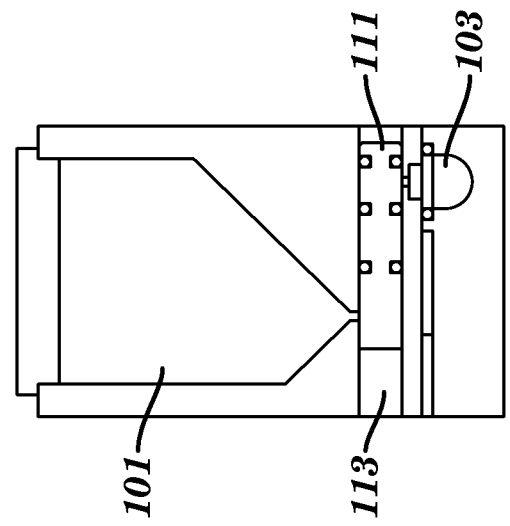
Figure 1D:
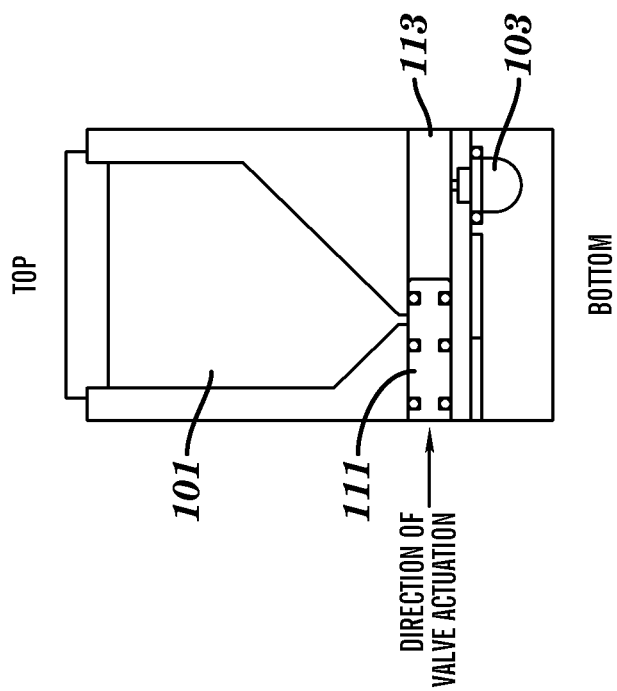

Now referring to FIG. 1D, 1E, and FIG. 2, in one embodiment, the invention provides a separator/concentration device for separation and concentration of particulates from a fluid sample by centrifugation comprising: (a) at least two chambers arranged vertically, a first chamber 101 and a second lower chamber 103, wherein the first chamber 101 has an inlet opening for sample application, wherein the first chamber 101 and second chamber 103 are connected by a first channel 113, which comprises a valve 111 which controls fluid sample transfer from the first chamber 101 to the second chamber 103; where the valve 111 housed within the first channel forms a tight seal preventing any material flowing from the first chamber to the second chamber. The movement of the first valve 111 from position 1 to position 2 allows fluid transfer from the first channel 101 to the second channel 103. In some embodiments, the valve 111 is a metered valve designed to dispense a pre-determined volume of particulate and fluid from the first chamber to the second chamber. FIG. 1A-1E show an embodiment of a separator/concentrator device that has two chambers.

Figure 2C:
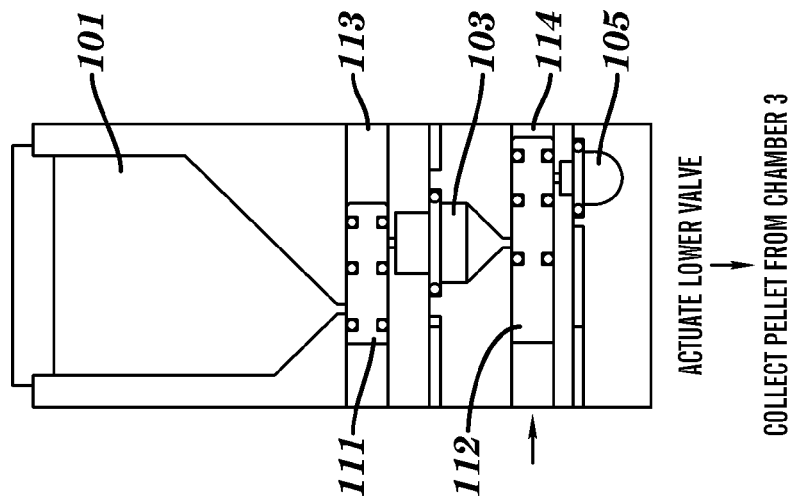
FIG. 2A-C illustrate the use of another embodiment of a separator/concentrator device comprising three chambers, a first chamber 101, a second chamber 103 and a third chamber 105, and a first valve 111 between the first and second chamber and a second valve 112 between the second and third valve for the separation, concentration and collection of particulates from a fluid sample.
Figure 2B:
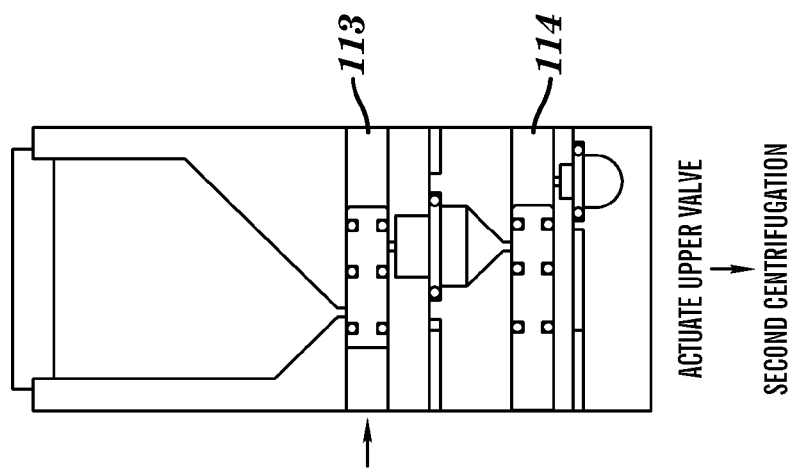
Figure 2A:
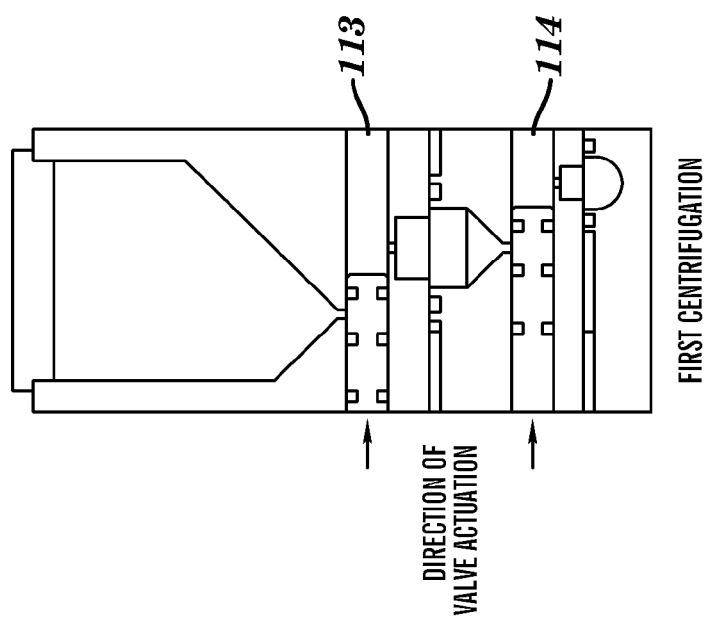

In one embodiment, the separator/concentrator device further comprises a third chamber, e.g., as shown in FIG. 2A-2B. In some embodiments, a third chamber is located below the second chamber 103, where the outlet of the second chamber 103 and inlet of the third chamber 105 are connected by second channel 115 which comprises a second valve 112 which controls fluid sample transfer from the second chamber 103 to the third chamber 105; where the second valve 112 housed within the second channel forms a tight seal preventing any material flowing from the second chamber to the third chamber. The movement of the second valve 112 from position 1 to position 2 allows fluid transfer from the second channel 103 to the third channel 105. In some embodiments, the second valve 112 is a metered valve designed to dispense a pre-determined volume of particulate and fluid from the second chamber to the third chamber. In some embodiments, as discussed herein, the first chamber can comprise a buffer before adding the fluid sample, for example where the buffer in the first chamber is a lysis buffer, for example, for preferentially lysing cells, e.g. blood cells while leaving bacterial cells intact. In some embodiments the lysis buffer a low percentage of tween-20. In some embodiments, a second or third chamber comprise a receiving fluid, e.g. a washing or rinsing fluid.

For example, in some embodiments where the separation device comprises three chambers, wherein the middle chamber can be use for "washing" or "rinsing" of the particulate material allowed into the middle chamber. In one embodiment, the second chamber further comprises a wash solution, such as water, saline, or buffers that are known in the art.

In some embodiments, the separator/concentrator device can comprise any number of chambers, for example, at least 2, or at least 3, or at least 4, or at least 5, or at least 6 or more chambers which can be configured to be fluidly connected to each other via at least one valve located between each chamber. In some embodiments, the second, third, fourth, fifth etc chambers are located anywhere in any order, and in some embodiments, the second, third, fourth and fifth chambers, etc. are located all together. In such embodiments, the outlet of the chamber above is connected to the inlet of the lower chamber by a channel comprising a valve, where valve operation from position 1 to position 2 controls the transfer of the fluid from the chamber situated above the lower chamber.

By way of an example only, a separator/concentrator device comprising four chambers has a first and second chamber connected by a first channel and a first valve, and a second chamber and third chamber connected by a second channel and a second valve, and a third chamber and a fourth chamber connected by a third channel and third valve, where valve operation of the first valve from position 1 to position 2 controls the transfer of fluid from the first chamber to the second chamber, and valve operation of the second valve from position 1 to position 2 controls the transfer of fluid from the second chamber to the third chamber, and valve operation of the third valve from position 1 to position 2 controls the transfer of fluid from the third chamber to the fourth chamber.

Figure 4B:
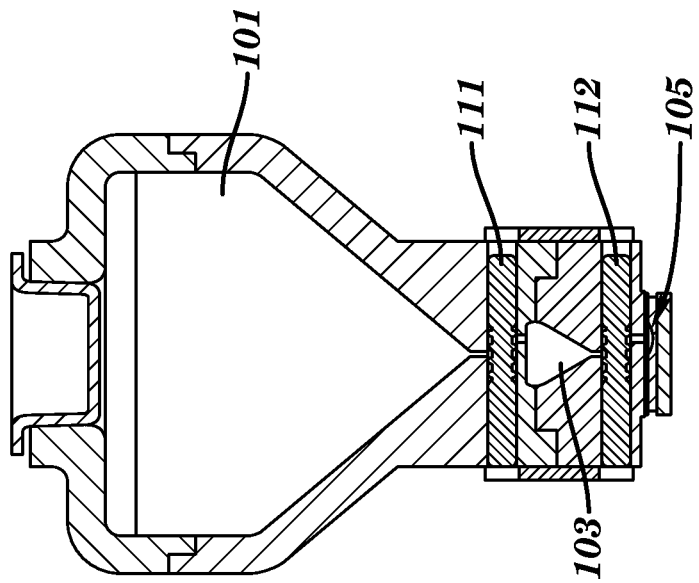
FIG. 4A-4E show perspective views of an embodiment of the disposable separator/concentrator device.
Figure 4A:
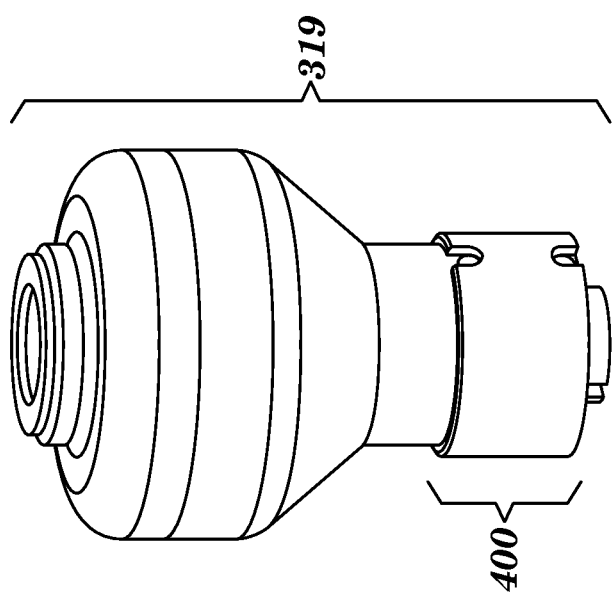
Figure 4E:
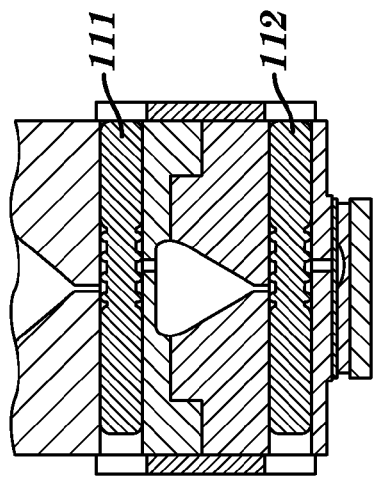
Figure 4D:
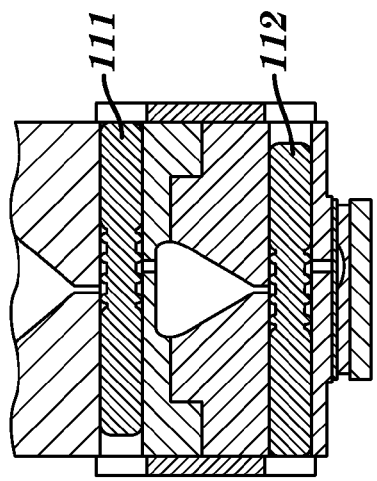
Figure 4C:
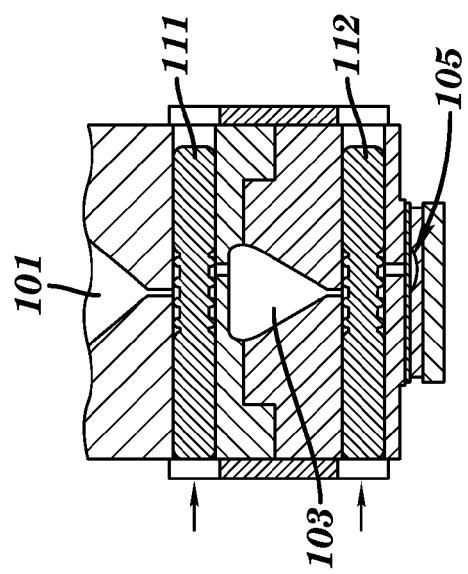

In some embodiments, the lowest positioned chamber serves as a collection chamber, which can be removed from the device to access the concentrated collected sample. For example, in embodiments where the separator/concentrator comprises 2 chambers, the second chamber 103 serves as the collection chamber. In other embodiments, where the separator/concentrator comprises 3 or 4 chambers, the third chamber 105 or fourth chamber serves as the collection chamber, respectively. In some embodiments, the lowest chamber, e.g. second, third or fourth chamber (or any other lowest chamber) which serves as a collection chamber is a slide. FIG. 4C shows an embodiment where the third chamber 105 functions as a slide collection chamber, where the slide collection chamber can be removed and directly analyzed under a microscope. In some embodiments, a separator/concentrator device comprises a first chamber and a first valve only, and can be configured to attach a collection chamber (e.g. a second chamber) to receive fluid from the first chamber.

In some embodiments, the lowest (e.g., the second chamber in a 2-chamber device, or a third chamber in a 3-chamber device etc) can function as a collection chamber, and collects the concentrated sample. Such collection chambers typically have an input for receiving a sample but do not have an output for sample outflow. In some embodiments, a collection chamber can be configured as any collection chamber, e.g. any collection tube, e.g., a 0.2 ml tube, or 0.5 ml tube, or 1.5 ml tube or 2.0 ml tube or any geometric configuration of a collection chamber to collect a concentrated sample, e.g., a collection chamber can be a slide, e.g., microscope slide which comprises in indentation to collect the sample from the outlet of the first channel. In some embodiments, the second chamber, or the lowest chamber (e.g. third, fourth, fifth chamber etc. of a multi-chamber device) which is a collection chamber can be removed from the separator/concentrator device after collection of the sample. In some embodiments, a collection chamber is separate from the device, and can be attached to a separator/concentrator device. In some embodiments, e.g., where a device comprises a first chamber and a first valve only, the device can be configured to attach a collection chamber to the lower portion of a 1-chamber, 1-valve device, such that the collection chamber can receive sample from the output of the first chamber, and where fluid transfer into the collection chamber is controlled by the operation of the first valve.

In some embodiments, the chambers can be vertically arranged on top of each other. In some embodiments the outlet of the top (e.g. upper) chamber and the inlet of the lower chamber are positioned directly vertically, e.g. in embodiments where a valve located in the channel separating the chambers comprises an indentation or void as the collection reservoir (e.g. see FIG. 1B). In alternative embodiments, the outlet of a top chamber and the inlet of a lower chamber are positioned vertically but at a small distance along the channel, e.g. in embodiments where a valve located in the channel separating the chambers comprises a metered groove as the collection reservoir (e.g., FIG. 1A, 1D, 1E and FIG. 2).

Disposable Separator/Concentrator Devices

FIG. 4 shows one embodiment of a single use, disposable separator/concentration device for use in a centrifuge, e.g., a swinging bucket centrifuge. In some embodiments, the disposable separator/concentration device shown in FIG. 4 can be used to isolate bacteria from a biological sample, e.g., a 100 mL sample of whole blood in approximately 10 minutes. In some embodiments, a disposable device as shown in FIG. 4A comprises at least one metering valve, and has a collection chamber, e.g. a third chamber, to extract a particulate from the sample directly from the bottom of a disposable device.

In some embodiments, a disposable device is useful in a method for separating bacteria from blood. For example, using a device as shown in FIG. 4, the method comprises adding blood to a first chamber comprising lysis buffer, e.g., where the lysis buffer preferentially lyses blood cells while leaving any bacteria cells intact, centrifuging the device with the first valve in position 3 to create a pellet of bacteria. In this embodiment, the blood lysis chemistry was optimized by modifying the concentration, volumetric ratios of lysis buffer to blood, and times involved. The first valve can be operated to position 1 to collect a portion of the pelleted bacteria, and centrifuging the device. A next valve operation of the first valve 111 to position 2 will transfer a portion of the supernatant from the first chamber into a second chamber, where the sample is diluted. The process is repeated, e.g. where device is spun, valve operation (operation of valve 2 to from position 3 to 1), spin, valve operation (operation of valve 2 to from position 1 to 2) to transfer a portion of the supernatant from the second chamber into a third chamber.

In some embodiments, the valves are metered valves. FIG. 4A shows an embodiment of the exterior of a disposable separator/concentrator device and FIGS. 4B and C show a cross-section of an embodiment of the disposable separator/concentrator device during a first centrifuge cycle. In some embodiments, the sample reservoir in a first chamber 101 can accommodate at least about 100 mL fluid sample, e.g. a blood sample and at least about 10-95 mL of buffer agent, e.g. a lysis buffer in the top chamber. In some embodiments, the first chamber 101 is sealed with a removable cover. At its base of the first chamber, the sample reservoir funnels down to a collection reservoir in the metering valve, e.g., a 10 μL metering valve. Once the blood has lysed, and any bacteria in the blood has pelletized in the metering valve, the valve is operated (e.g. manually, semi-manually or automatically) and the 10 μL of sample in the metering valve is transferred to the second chamber, e.g., a dilution chamber. FIG. 4D shows one embodiment of the disposable separator/concentrator after a first valve (top valve) 111 operation to position 2. The second chamber 103, e.g., a dilution reservoir can comprises a dilution fluid, e.g., 900 μL water or other dilution buffer in order to dilute the sample by 1:100 and thus dilute the lysis buffer transferred by approximately 99%.

Any bacteria that has been transferred to the second chamber 103 e.g., a dilution reservoir is re-pelletized with a second centrifugation into a second metering valve. FIG. 4E shows an embodiment where the first and second valves of a 3-chamber disposable separator/concentrator are in position 2 after operation of a second valve. In some embodiments, when the second (or lower) valve is operated to position 2, 5 μL of the sample from the second chamber is transferred to the third chamber 105 (e.g. a collection chamber or transfer reservoir) where the concentrated sample can then be retrieved by the user.

The first chamber 101 is designed to hold the volume of the fluid needing separation. In some embodiment, the first chamber can hold a volume from a range of about 10 nanoliters to about 1 liter. In one embodiment, the volume can range from 10 nanoliters to 100 microliters. In other embodiments, the volume can range from 10 microliters to 100 milliliters. In some embodiments, the first chamber is designed to hold the volume of the fluid needing separation, the volume can range from 10 nanoliters to 10 L. In some embodiments, a first chamber is designed to hold a volume of between 100 ml and 1 L, or any integer between about 100 ml and 1 L. In one embodiment, the volume can range from about at least 1 ml to about 10 ml, or about at least 10 ml to about 100 ml, or about 100 ml to about 500 ml, or about 500 ml to about 1 L, or about 10 nanoliters to 100 microliters. In other embodiments, the volume can range from 10 microliters to 20 milliliters or any integer between. In some embodiments, the volume can be about 10 ml, or about 100 ml. Any fluid with insoluble particles can be used, e.g. whole blood with blood cells or bacteria, water (e.g., pond, river, sedimentary water) with microbes, urine, bronchoalveolar lavage, cerebral spinal fluid and the like.

In the embodiments described herein, a first chamber 101 is also designed to be wide at the inlet at the top for ease of fluid input and funnel into an outlet at the bottom of the chamber (see FIG. 7-9) that connects to the first channel which connects to the inlet of the second chamber. The sizes and shapes of the chambers and channels can be changed accordingly to adapt to the type of fluid needing separation, the type, volume, and size of particles to be collected, and the desired collection volume. In one embodiment, the bottom chamber, e.g., a third chamber 105 in a three-chamber device is smaller than the first chamber 101. In one embodiment, the bottom chamber, e.g., a third chamber 105 in a three-chamber device can contain a wash or suspension solution for collection of the pellet particle.

In one embodiment of the separator/concentrator device described herein, the fluid sample is a blood sample. In other embodiments, the fluid sample can be any biological sample, e.g. water, or bodily fluids such as urine, aspirates, or cerebrospinal fluid (CSF), plasma, semen and the like. In other embodiments, the fluid is a sample, e.g. water sample, for example pond or beverage or other water sample, and can be used, for example to check for impurities and contaminants present in a fluid sample.

In some embodiments, the separator/concentrator device described herein contains a first and/or second solution in any of the chambers, for example, a lysis buffer or a surfactant solution in the first chamber. In some embodiments, a lysis buffer can be used to lyse blood cells but not bacterial cells when the fluid sample is a blood sample. In one embodiment, the lysis buffer is 0.005% tween 20 solution. In one embodiment, the lysis buffer is a 0.8% $Na_2CO_3$/0.05% TRITON X-100 solution. In one embodiment, the ratio of lysis buffer to blood sample in the top chamber is 1:1. In other embodiments, the ratio of lysis buffer to fluid sample is 1:2, 1:3, 1:4 or 1:5, 1:9, 1:20. In some embodiments, the concentration of tween 20 is 0.005%.

In one embodiment, the chambers of the separator/concentrator device are coated with 0.5 g/L pluronic or 1% BSA or any other coating materials for preventing the particulate matter from adhering to the walls of the separation device. Depending on the material used for the walls of the separation device and also the fluid and particulate matter needing separation, coating of the walls may or may not be required. One skilled in the art would be able to determine this with the simple testing procedures described herein.

In one embodiment, the first chamber 101 of the separator/concentrator device contains a lysis buffer. In one embodiment, the lysis buffer lyses blood cells or other cells or microorganisms.

In one embodiment, the second chamber 103 of the separator/concentrator device contains a volume of diluting fluid, e.g., water or washing solution for rinsing the particulate matter, e.g. the second chamber can comprise at least a volume of about 1000 microliters or less than 1000 µL, for example, where a device comprises three chambers.

In one embodiment, the first chamber 101 of the separator/concentrator device contains a lysis buffer and the second chamber 103 of a separation device contains a volume of buffer, e.g., water, wherein the device comprises three chambers.

In some embodiments, the separator/concentrator device can be constructed of any appropriate material including but are not limited to polymer materials to polyacetal, polyurethane, polyester, polytetrafluoroethylene, polyethylene, polymethylmethacrylate, polyhydroxyethyl methacrylate, polyvinyl alcohol, polypropylene, acetal Copolymer, PEEK, PEVA, Acrylic, polycarbonate, polymethylpentene, polyetherketone, polyphenylene oxide, polyvinyl chloride, polycarbonate, polysulfone, acrylonitrile-butadiene-styrene polyetherimide, polyvinylidene fluoride, and copolymers and combinations thereof. Other preferred materials include polysiloxane, fluorinated polysiloxane, ethylene-propylene rubber, fluoroelastomer and combinations thereof. Other preferred materials include polylactic acid, polyglycolic acid, polycaprolactone, polyparadioxanone, polytrimethylene carbonate and their copolymers.

In one embodiment, the separator/concentrator device is constructed as a one-piece device, e.g. by injection molding or other methods known in the art. In other embodiments, the separation device is constructed from several pieces or parts, as in a separation device made of modular units. For example, each modular unit can comprise a chamber with an inlet and an outlet, where the outlet connects to a channel which can house a valve, and where the chamber has an outlet which connects to the inlet of another chamber, where the other chamber is the next chamber in a next modular unit. In such embodiments, any number of modular units can be fitted together, e.g. 3 modular units for a three-chamber device as described herein. In some embodiments, the units can be assembled together by various methods known in the art (see FIG. 3, 7-9 and the Example section).

Figure 3:
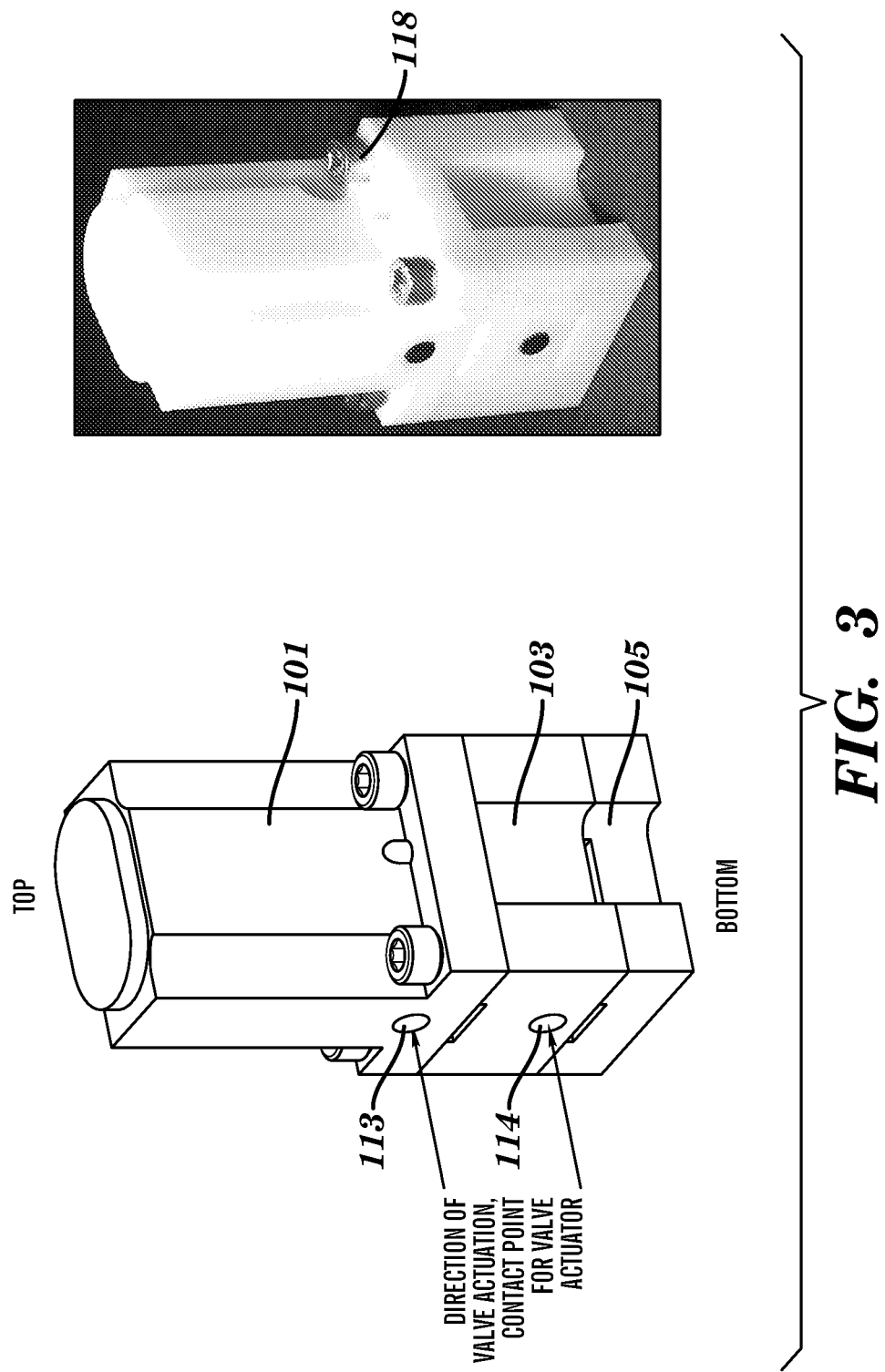
FIG. 3 shows two perspective views showing an embodiment of a separator/concentrator device comprising three chambers 101, 103 and 105 shown in FIG. 2.
Figure 8:
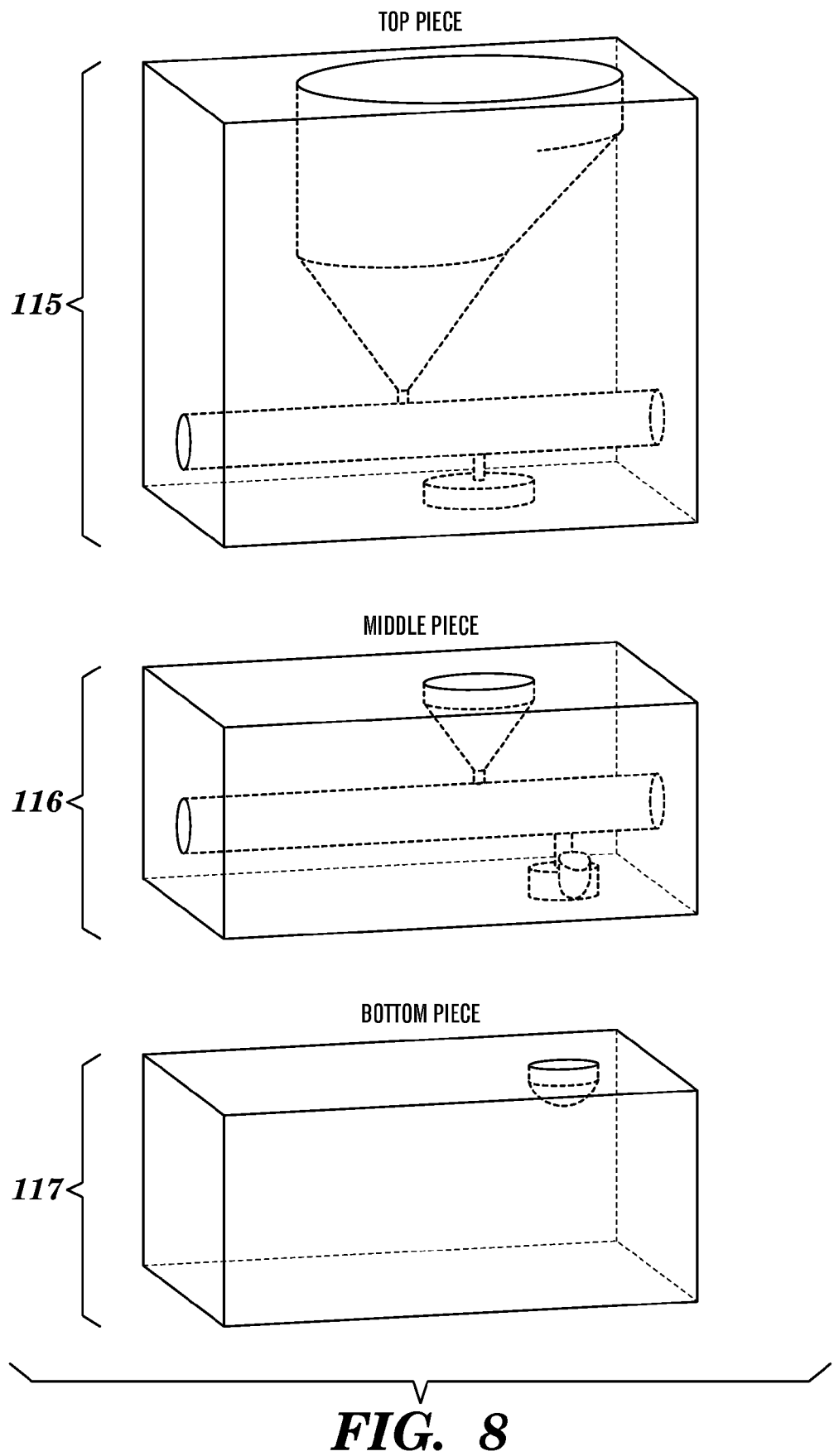
FIG. 8 is a schematic diagram showing the three pieces cut from the design of FIG. 7. These pieces can be cast, e.g. molded or machined, and can be held together by fasteners through the shown fastener holes.
Figure 9B:
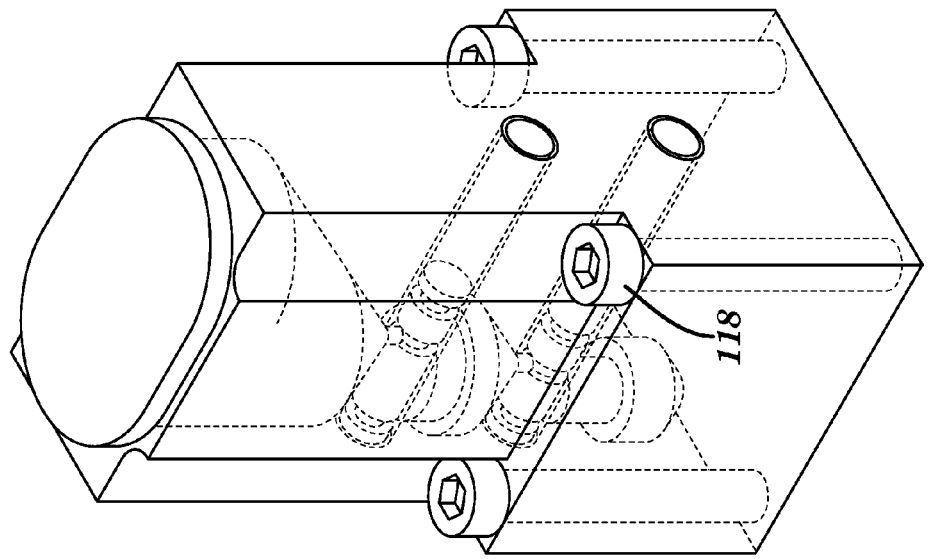
FIGS. 9A-9B are schematic representations of one embodiment of a separator/concentrator device.

Injection molding is one possible method of producing a one-piece disposable separation device. Alternate method is to build the separation device in parts and assemble them together as shown in FIG. 3-9. In some embodiments, a three-chamber separation device can be manufactured using three machineable pieces that can be fastened together by any secure method, e.g., with a plurality of bolts or clasps at each corner of the device, as shown in FIG. 9B. In some embodiments, for a three-chamber device the machineable pieces can be configured as follows: (i) a first top machineable part 115 comprises the first chamber 101, the first channel 113 and a first portion of the second chamber 103, (ii) a middle machineable part 116 can comprise the remaining portion of the second chamber 103, the second channel and a first portion of the third chamber 105, (iii) and a bottom machineable part 117 comprising the remaining portion of the third chamber 105, as shown in FIG. 8. However, any means to manufacture the disposable device is encompassed. A schematic diagram of the three pieces is shown below in FIG. 7-8. In some embodiments, the three pieces can be configured to be assembled together to form a secure seal, where the bottom of the first manufactured piece 115 is configured to securely attach to the top of the second manufactured piece 116, and the bottom of the second manufactured piece 116 is configured to securely attach to the top of the bottom manufactured piece 117. In some embodiments, the manufactured parts can fit or slide together like a jig-saw as shown in FIG. 4B. In some embodiments, the manufactured parts, 115, 116, 117 are held in place with an adhesive, sealant, or glue, and in other embodiments, the manufactured parts 115, 116, 117 can be held together using an ensheathing material, e.g. plastic surrounding the entire device.

Figure 9A:
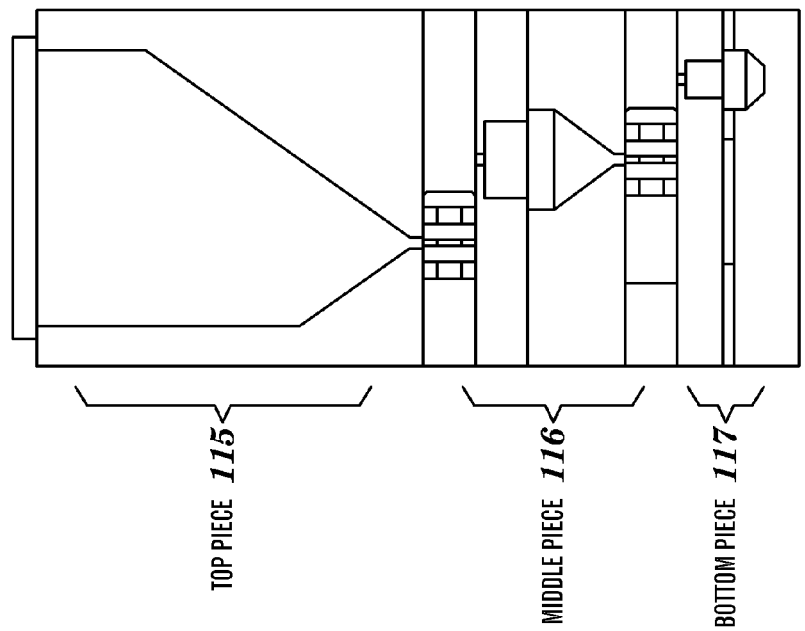

In some embodiments, the manufactured parts 115, 116, 117 are held together securely using a fastener 118, e.g. bolts, for example, as shown in FIG. 9B, where each manufactured piece has been configured to have room for fasteners. In some embodiments, where a fastener such as a bolt is used to secure the manufactured parts 115, 116, 117 together, the bottom manufactured part 117 contains a bolt counter-bored thru-hole, the middle part 116 is configured with a bolt thru-hole, and the top part 115 is configured to have a bolt-thread area. In some embodiments, the top manufactured part 115 is configured to comprise a lid for the top chamber 101 in order to prevent accidental fluid sample spills. FIGS. 3 and 9 show the final assembled three-piece device separation device.

In one embodiment, the separator/concentrator device is a single use device, meaning that the device is use only once and then discarded. In another embodiment, the separation device is a multiple-use device, wherein after a first use to separate a first fluid sample, the device is washed and cleaned, and in some embodiments, sterilized and used again for a second and subsequent fluid sample separations.

Operation of the Separator/Concentrator Device

Figure 6B:
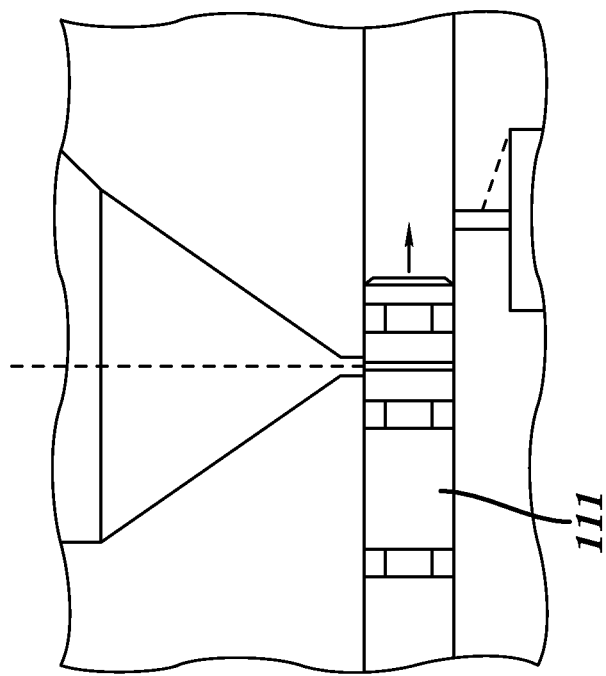
FIGS. 6A-6B show a cutaway representation of one embodiment of a valve system showing the valve connecting the top and middle chambers.
Figure 6A:
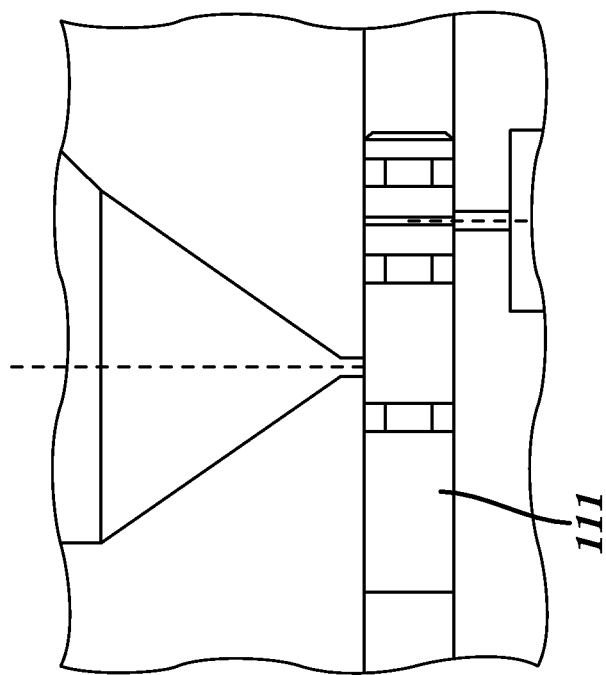

The separator/concentrator device is designed to be used with centrifugation. For example, in fluid separation/concentration using a two-chamber device, before the beginning of a centrifugation cycle, the first valve 111 is positioned within the channel 113 in position 3 or 1 to tightly seal and block any leakage from the first chamber 101 into the second chamber 103. If the first valve 111 is in the first position, fluid flow occurs from the top chamber 111 to the collection reservoir, e.g., a metered groove of the first valve 111 as shown in FIG. 6A. Tight seal can be achieved by rubber "O" rings on the valve. During centrifugation, the particulate materials in first (e.g., top) chamber 101 will sediment to the bottom outlet of the funnel-shaped first chamber (FIG. 1A) and enter the collection reservoir, e.g., the metered groove of the first valve 111. After the particulate material has accumulated at the bottom of the first chamber and in the collection reservoir (e.g., metered groove) of the first valve 111 at the end of the first centrifugation cycle, operation of the first valve 111 to a second position (position 2) in the channel 112 allows the flow of material from the valve collection reservoir (e.g., from the metered groove) of the first valve 111 to the inlet of the second chamber 103 as shown in FIGS. 1B and 6B. A second centrifugation cycle moves the particulate material from valve collection reservoir (e.g., from the metered groove) of the first valve into the second chamber 103 and to the outlet at the bottom of this second chamber.

In the embodiment of a three-chambered separator/concentrator device, there will be two valves, an first valve 111 and a second valve 112, and a respective first channel 112 and a second channel 114, a first valve 111 is in a first channel 113 that connects the first chamber 101 and second chamber 103, and a second valve 112 in a second channel 114 that connects the second chamber 103 and third chamber 105 as shown in FIG. 2 and FIG. 4.

Before the beginning of any centrifugation cycle, the first valve 111 and second valve 112 are positioned, either in position 1 or 3, in their respective channels 113 and 114 to tightly seal and block any leakage from the chamber above the valve to the chamber below the valve with respect to that valve and respective channel. In some embodiments, the first valve 111 is positioned so that the valve collection reservoir is aligned with the inlet of the first chamber 101, to allow a clear flow passage of material from the first chamber 101 to the valve collection reservoir e.g., metered groove of the valve. After the first centrifugation, the first valve 111 is operated to be moved into position 2 so that the valve collection reservoir is aligned with the inlet of the second chamber 103 to allow a clear flow of material from the valve collection reservoir, e.g., a metered groove of the valve to the second chamber 103. A second centrifugation cycle is started wherein the particulate material from the valve collection reservoir, e.g., a metered groove of the first valve 111 is sediment into the second chamber 103, and to the outlet at the bottom of the second chamber, and where the second valve 112 is into the first position, into the valve collection reservoir of the second valve 112. After a second centrifugation cycle, the second valve 112 is operated to be moved into a second position (e.g. position 2) so that the valve collection reservoir is aligned with the inlet of the third chamber 105, allowing a clear flow passage from the valve collection reservoir in the second valve 112 into the third chamber 105 for final collection (FIGS. 2 and 4).

As disclosed herein, the separator/concentrator device, e.g. a disposable separator/concentrator device can be combined with an actuation mechanism for operating the valves. Exemplary actuation devices are disclosed herein, and include semi-manual actuation devices (e.g. a cam sleeve actuation device) and automatic actuation device (e.g. an inertial actuation device), however, such actuation devices are by no means the only actuation devices which can be configured to actuate the valves of the disposable separator/concentrator device. Typically, the actuation devices provide a mechanism to operate the valves in the correct order and thus prevent incorrect operation of the disposable separator/concentrator by operation of the valves in the wrong order.

In some embodiment, the centrifugation of the separator/concentrator device is performed in a fixed-angle, a swing-bucket, or purpose-built centrifuge. In one embodiment, the centrifugation is performed in a standard commercially available centrifuge. In another embodiment, the centrifugation is performed in a clinical centrifuge. Clinical centrifuges are well known in the art and are used for analysis of blood, other bodily fluids, and environmental samples.

The following is a general operating procedure for an embodiment where the separator/concentrator device is a three-chamber, two-valve separator/concentrator device as shown in FIGS. 3, 4, 9, 13 and 14.

A. Thoroughly cleaned all surfaces before after use. Cleaning can be done by any methods commonly known by persons of ordinary skill in the art, and include for example, cleaning by the manufacturer, or any sterile cleaning system such as steam, autoclave, radiation sterilization and the like. In some embodiments, assembly steps 1-11 can be performed by the manufacturer.

B. Assembly:
1. Lay O-ring in groove around chamber bottom piece 117 housing the third chamber 105 (final collection chamber) (See FIGS. 8 and 9).
2. If required, fill third chamber 105 with water.
3. Align and place middle piece 116 on the bottom piece 117 so the output of the middle piece 116 is aligned with the top portion of the third chamber 105.
4. Lay O-ring in groove around the chamber of middle piece 116.
5. If required, fill middle chamber 103 with water. This can be done after assembly, if required volume overfills chamber.
6. If required, lay filter over O-ring on middle chamber 103.
7. Align and place top piece 115 on the middle piece 116 so the output of the top piece 115 is aligned with the top portion of the second chamber 103.
8. Securely attach the top, middle and bottom pieces 115, 116, 117. Insert four 1¾" ¼"-20 screws. Tighten evenly. Avoid under-tighten as it will ruin the threads during centrifuge cycles. In some cases, using two screws may be adequate.
9. Install three O-rings on each valve 111, 112. Ensure that none are twisted.
10. Carefully insert valves 111, 112 chamfered end first into the side nearest the top chamber output hole. Insert until exposed end is flush with the outside of the prototype.
11. If required, fill second chamber 102 through angled side port.
12. Fill first chamber 101 with sample.
13. Cover first chamber 101 with lid. Optionally, tape lid down.
14. Ensure opposite bucket is counter-balanced within ½ gram.

Disassembly
1. Remove the separator/concentrator from the centrifuge, carefully keeping upright. Place on a firm level surface.
2. If water level in second chamber 103 is above the O-ring, use a syringe with a 1" needle, through the angled port, to lower the water level.
3. Detach each of the manufactured parts 115, 116, 117 by unscrewing all the screws.
4. Properly dispose of liquid in first 101 and second 103 chambers.
5. Use plastic tweezers or other plastic tool to remove O-rings from valves.

Clean-Up
1. Dispose of all O-rings after every test involving biological.
2. Clean all surfaces, inside and out.
   a. If using blood, use 10% bleach followed by rinsing with water.
   b. If using just bacteria, use 70% ethanol on all parts.
3. Dry thoroughly with paper towels and compressed air.

Uses of the Disposable Separator/Concentrator Device

In some embodiments, the disposable separator/concentrator device is useful as a disposable medical device that can be used to quickly and efficiently (~10 mins) extract particles, e.g., bacteria from a biological sample, e.g., from blood or other biological samples such as liquid physiological samples; urine, CSF, etc) and concentrates it for analysis. As this is a disposable closed system it also reduces risk of contamination of the sample, and/or exposure of the operator to potential harmful pathogens and bacteria. Also, as the process does not require a technician to add any buffers or samples other than the biological sample to be concentrated, reduces human error and the process can be operated with by users with minimal training. Furthermore, the use of such a disposable separator/concentrator device in a separation system enables one to steamline a labor intensive process of concentrating a sample and also removes the need for delicate pipetting operations. The separator/concentrator device incorporates valves that maintain a liquid seal, transferring a precise amount of liquid, and can be operated quickly and safely actuated either manually or semi-manually by hand, or automatically using the actuation devices as disclosed herein.

In some embodiments, the separator/concentrator device extracts the pelleted material directly from the bottom of a sample, without disturbing the remaining non-pellet sample or supernatant.

In one embodiment, the separator/concentrator device is a single use device, meaning that the device is use only once and then discarded. In another embodiment, the separation device is a multiple-use device, wherein after a first use to separate a first fluid sample, the device is washed and cleaned, and then used again for a second/different fluid sample.

In some embodiments, the disposable separator/concentrator device is useful for concentrating a sample for use in subsequent downstream diagnostics, and the concentrated sample can be used in methods where concentration of particulates in a sample is beneficial, e.g. bacteria from blood or other fluids, which can be used in subsequent analysis e.g. PCR, bioMEMS devices, etc.

In some embodiments, the disposable separator/concentrator device is useful for particle or cell separation to separate particles of different sizes, e.g., specific cell types such as neutrophils or stem cells or particles from bodily fluids, e.g., platelets and other blood products such as red cells and plasma. In some embodiments, the disposable separator/concentrator device is useful for concentration of particles in bodily fluids, e.g., compositions which are enriched in platelets and depleted in neutrophils.

In some embodiments, the disposable separator/concentrator device could be adapted to concentrating and extracting contaminants and precipitates from any type of solution. In some embodiments for example, the first chamber 101 can be pre-loaded to comprise different lysis buffers depending on the cell type which is required to be lysed in the fluid sample loaded into the top chamber. In some embodiments, the second chamber 103 can be pre-loaded with different buffers, e.g. washing solutions can be used to wash the pelleted sample which is obtained from the first (top) chamber 101. In addition, the disposable separator/concentrator device can comprise filters to remove larger solids from the fluid sample to be concentrated before loading into the top chamber of separator/concentrator device. Such filters can be mesh filters or other filters commonly known in the art which allow penetration of cells but prevent the penetration of large cells aggregates or fibrous tissue.

In some embodiments, the disposable separator/concentrator device is fully disposable. In other embodiments, parts of the separator/concentrator device are disposable, and parts are reusable. For example, in some embodiments, the chambers and housing of the separator/concentrator device is disposable, and the valve, e.g. the metered valve is reusable. The reusable metered valve can be sterilized by any means know by one of ordinary skill in the art between each use in different separator/concentrator devices. Further, reusable versions of the separator/concentrator device, including reusable cambers and housing of the separator/concentrator device and the valve, e.g. the metered valve are also encompassed herein.

Valves of the Separator/Concentrator Device

As disclosed herein the flow of the sample from one chamber to another in the separator/concentrator device is controlled by a valve located in a channel which is between and connects each chamber. The valve can be operated by any a variety of different ways, for example, manually, semi-manually, semi-automatically or automatically, as disclosed herein.

The valve can be operated in a linear motion such as a pulling or a pushing motion. For example, in some embodiments, a valve can be operated to move the valve from a position 1 to position 2 in a linear motion along the channel, such as a pulling (e.g., See FIG. 1A) or a pushing motion. Alternatively, the valve can be operated in a linear motion using a screw-like rotational motion, for example, a valve can be configured with a helical screw-like mechanism which connects with the channel so that the valve can be operated so that rotation of the valve will move the valve in a linear direction from position 1 to position 2. In other embodiments, the valve can be operated by a rotational movement to rotate the valve from position 1 to position 2, e.g. see FIG. 1B. The valve can be operated by any manual, semi-manual or automatic actuator as disclosed herein. In some embodiments, where a separator/concentrator has at least two valves, the valves can be configured to be operated by different mechanisms, e.g., a first valve 111 can be operated by moving the valve in a linear direction along the channel 113 from position 1 to position 2 (see FIG. 1A), and a second valve 112 can be operated by a rotational movement to rotate from position 1 to position 2 (see FIG. 1B). In such embodiments, the inlet of the second chamber 103 is typically offset from the outlet of the first chamber 101, and the inlet of the third chamber 105 is located substantially aligned with the outlet of the second chamber 103.

The valve can be operated by any manual, semi-manual or automatic actuator as disclosed herein. In some embodiments, where a separator/concentrator has at least two valves, valve operation of each valve, e.g., can be by different operation mechanisms, e.g., a first valve 111 can be operated manually and a second valve 112 can be operated automatically. Thus, one can use any combination of different methods to operate a plurality of valves a separator/concentrator device as disclosed herein. Typically, in some embodiments, all the valves in a separator/concentrator device are operated the same method, e.g., by a manual, semi-manual or automatic method of operation.

In some embodiments, the valve can be operated manually, for example by hand, where the valve is pushed in, or pulled out, by any means know to one of ordinary skill in the art. In one embodiment, the valves are operated by hand, without the aid of an operatively attached actuation device. In one embodiment, the valves are operated by hand with or without the aid of a rod to access the valves in their respective channels. In such an embodiment, a valve can be operated manually by hand after the stop of centrifugation.

In one embodiment, the valves in the separator/concentrator device are operated to allow a specific volume of fluid from the one chamber (e.g., the chamber above the valve) into a second chamber (e.g. the chamber below the valve) The specific volume which is transferred is determined by the volume of the valve collection reservoir, and can be a volume of any amount depending on the type, volume, quantity and size of particles to be collected, and the desired collection volume. For example, the volume of the valve collection reservoir can range from 10 nanoliters to 10 milliliters. In some embodiments, the volume of the valve collection reservoir, and thus the volume which is transferred between chambers can range from about at least 10 nanoliters to 10 milliliters. The volume transferred between chambers can be predetermined if a metered valve is used, e.g. a valve with a metered groove collection reservoir or a metered void collection reservoir, where the collection reservoir allows the transfer of at least 10 nl, or more, for example, about 5 μl, or about 10 μl, or about 100 μl or about 1 ml, or about 2 ml, or between 2 ml and 10 ml, or any integer between 10 nl and 10 ml.

In some embodiments, the valve is a metered valve. In one embodiment of the separator/concentrator device described herein, the valve is a metered valve e.g., where a valve configured to have a collection reservoir of a specific volume which collects a volume of sample from the outlet of an upper chamber, and is then operated to dispense the specific predetermined volume collected in the collection reservoir into the inlet of a receiving chamber, e.g., a second chamber. In some embodiments, a valve collection reservoir collects 10 μl from the outlet of one chamber and dispenses 10 μl into the inlet of another chamber. Such metered valves comprising collection reservoirs permit a predetermined volume of sedimented particulate matter from the outlet of one chamber (e.g. the chamber above the valve) into the inlet of a second chamber (e.g. the chamber below the valve). A metered valve is a valve comprising a collection reservoir, e.g. a void (see FIG. 1B) or a groove (see FIG. 1A or FIG. 5) which allows a pre-defined volume of sample to pass from one chamber to the next. In some embodiments, the valve collection reservoir has any desired volume, e.g., any volume, e.g. between 10 nl to 10 μl or 100 μl to 1 ml, and in some embodiments the valve collection reservoir, e.g., grove allows for the transfer of about at least 5 μl, or in some embodiments the grove allows for the transfer of about at least about 5 μl, or at least about 6 μl, or at least about 7 μl, or at least about 8 μl, or at least about 9 μl, or at least about 10 μl, or at least about 15 μl, or at least about 20 μl, or at least about 30 μl, or at least about 40 μl, or at least about 50 μl, or at least about 100 μl, or more than 100 μl of fluid volume to be transferred to the next channel.

Figure 5A:
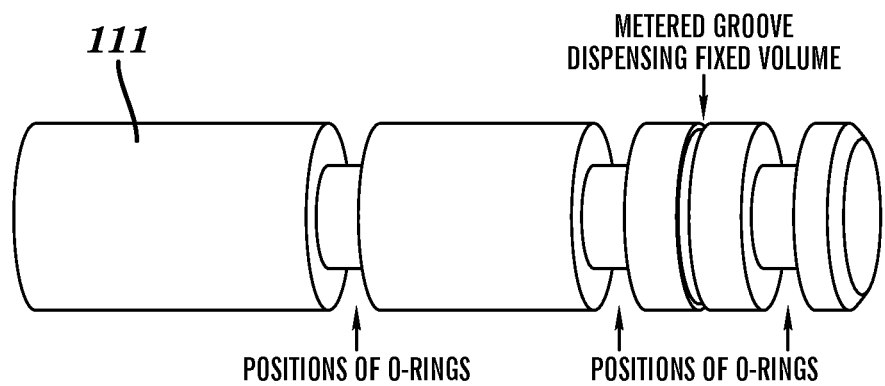
FIG. 5 is a perspective view of one embodiment of a metered valve designed for transferring a fixed volume from the top chamber. Shown are the metered grooves or chambers for dispensing a pre-defined fixed volume from an upper chamber to a lower chamber.
Figure 5B:
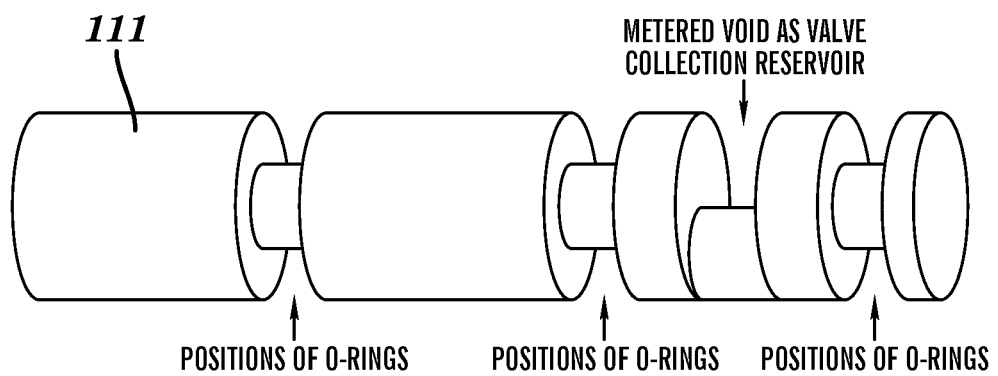

In some embodiments, where a separator/concentrator has at least two valves, the collection reservoirs in the different valves can be of different volumes. For example, in a separator/concentrator comprising three chambers, a first valve 111 can have a collection reservoir with a volume of about between 10 nl and 10 ml, e.g., about 1000 μl, and the second valve 112 can have a collection reservoir with a volume of about between 10 nl and 10 ml, e.g., about 10 μl. In some embodiments, a valve collection reservoir has a volume of any amount such as any volume between 10 nl and 10 ml. In other embodiments, a valve collection reservoir has a volume ranging from 5 μl to 10 mL. An embodiment, a valve collection reservoir of a metered valve is shown in FIG. 5. One skilled in the art can configure a valve to have a valve collection reservoir of any desired geometric shape for dispensing a desired pre-determined volume into the inlet of a second or subsequent chamber.

FIGS. 5 and 6 show an embodiment of a metered valve comprising a groove as the valve collection reservoir and its design for moving from position 1 to position 2 within a channel of the separator/concentrator device. A metered valve can be designed and positioned to tightly seal and block any leakage from the upper chamber to the lower chamber during acceleration and at targeted gravitational force. Tight seals can be achieved by "O" rings on the valve, such as "O" rings made of rubber.

The metered valve can be made out of any material, for example, can be a disposable material of plastic, synthetic or other devices. In some embodiments, a metered valve is a disposable movable device. In some embodiments, a metered valve is a reusable movable device, which can be sterilized by any means known to one of ordinary skill in the art between uses in the methods and deposable separator/concentrator devices. In some embodiments, the valve can be constructed of any appropriate material known to persons of ordinary skill in the art including but are not limited to polymer materials to polyacetal, polyurethane, polyester, polytetrafluoroethylene, polyethylene, polymethylmethacrylate, polyhydroxyethyl methacrylate, polyvinyl alcohol, polypropylene, acetal Copolymer, PEEK, PEVA, Acrylic, polycarbonate, polymethylpentene, polyetherketone, polyphenylene oxide, polyvinyl chloride, polycarbonate, polysulfone, acrylonitrile-butadiene-styrene polyetherimide, polyvinylidene fluoride, and copolymers and combinations thereof. Other preferred materials include polysiloxane, fluorinated polysiloxane, ethylene-propylene rubber, fluoroelastomer and combinations thereof. Other preferred materials include polylactic acid, polyglycolic acid, polycaprolactone, polyparadioxanone, polytrimethylene carbonate and their copolymers.

Manual Actuation of the Valves

In some embodiments, valve operation occurs manually after each centrifugation cycle without the help of any additional apparatus that is physically and operatively attached to the separator/concentrator device. In such embodiments, the valves are moved by hand.

In some embodiments, a rod can be used to reach into the channels and push the valves in the channel of the device. In some embodiments, the pushing is done manually by hand. The rod represents a non-physically attached apparatus for moving the valves. In some embodiments, the rod can be used to manually pull the valves in the channel of the separator/concentrator device, for example where there is a toggle catch on the valve which connects to a toggle catch on the rod, so the rod can be used to pull the valve. In some embodiments, the rods are disposable. In some embodiments, the rod and the valve are reusable.

In one embodiment of a two chambered separator/concentrator device, the first valve 111 is pushed in after the end of the first centrifugation cycle when the centrifuge has come to a stop. In one embodiment of a three chambered separator/concentrator device, the two valves, 111, 112 are operated sequentially after each of two consecutive centrifugation cycles. After the centrifuge comes to a stop at the end of the first cycle, the first valve 111 is operated manually. A second centrifugation cycle is then performed, and at the end of the second cycle, the second valve 112 is pushed.

In some embodiments, the valves of the separator/concentrator device can be operated manually after each centrifugation cycle. In some embodiments, valves operation occurs manually without the aid of an apparatus attached to the device.

The following are the exemplary steps for manual valve operation of a separator/concentrator device having two chambers (FIG. 1) after each centrifugation cycle. The manual operation of the valve does not have to involve an apparatus physically attached to the device, e.g. an actuation device.

Step 1: Before the beginning of any centrifugation cycle, the first valve 111 is positioned within the channel 113 in position 1 or 3 to tightly seal and block any leakage from the first chamber 101 to the second chamber 103. If the valve is position 1, the valve collection reservoir is aligned with the outlet of the first chamber 101 to allow a clear flow passage from the first chamber 101 to the collection reservoir, e.g., metered groove of the first valve.

Step 2: Load the first chamber 101 with the fluid sample to be separated and/or concentrated. Cap the top of this chamber to avoid spillage during centrifugation.

Step 3: Place the separator/concentrator device into a centrifuge. Start a first centrifugation cycle for 5 minutes at 3000 rcf to sediment the particulate matter in the first chamber 101, the particulate matter will sediment towards the outlet at the bottom of the first chamber and into the collection reservoir, e.g., metered groove of the first valve 111.

Step 4: At the end of the first centrifugation cycle, after the centrifuge has stopped, remove the separator/concentrator device from the centrifuge and manually operate the first valve 111 to a second position in the channel so that the valve collection reservoir is aligned with the inlet of the second chamber 103 to allow a clear flow passage from the metered groove of the valve to the second chamber 103 as shown in FIGS. 1B and 6B. A rod can be used to reach the valve in the channel.

Step 5: Replace the separator/concentrator device into the centrifuge. Start a second centrifugation cycle for 5 minutes at 3000 rcf to move the particulate material from the collection reservoir, e.g., metered groove of the first valve 111 into the inlet of the second chamber 103 and to the bottom of this chamber for collection.

Step 6: At the end of the second centrifugation cycle, after the centrifuge has stopped, remove the separator/concentrator device from the centrifuge, access the second chamber and collect the sedimented/concentrated sample.

The following are the exemplary steps for operating a separator/concentrator device having three chambers with manual actuation of the valves with each centrifugation cycle. In some embodiments, the valves are moved without the aid of an apparatus attached to the device.

In the embodiment of a three-chambered separator/concentrator device, there will be two valves, 111, 112 and respective channels 113, 114, a first valve 111 is in a first channel 113 that connects the first chamber 101 and second chamber 103, and a second valve 112 in a second channel 114 that connects the second chamber 103 and third chamber 105 as shown in FIG. 2 and FIG. 4.

Step 1: Before the beginning of any centrifugation cycle, the both valves 111, 112 are positioned within the channels to tightly seal and block any leakage from the chamber above the valve to the chamber below the valve with respect to that valve and respective channel. At the same time, each valve can be positioned in the first position (position 1) to allow a clear flow passage from the chamber above the valve to the metered groove of the valve.

Step 2: Load the top chamber 101 with the fluid sample to be separated and/or concentrated. Cap the top of this chamber to avoid spillage during centrifugation.

Step 3: Place the separator/concentrator device into a centrifuge. Start a first centrifugation cycle for 5 minutes at 3000 rcf to sediment the particulate matter in the first chamber 101, the particulate matter will sediment towards the outlet of the bottom of the first chamber and into the collection reservoir, e.g., metered groove of the first valve 111.

Step 4: At the end of the first centrifugation cycle, after the centrifuge has stopped, remove the separator/concentrator device from the centrifuge and manually operate by pushing the first valve 111 to the second position (position 2) align the collection reservoir, e.g., metered groove of the first valve 111 with the inlet of the second chamber 103 to allow a clear flow passage from the collection reservoir, e.g., metered groove of the first valve to the second chamber 103 as shown in FIGS. 2B and 4D. A rod can be used to reach the valve in the channel.

Step 5: Replace the separator/concentrator device into the centrifuge. Start a second centrifugation cycle for 5 minutes at 3000 rcf to move the particulate material from the collection reservoir, e.g., metered groove of the first valve 111 into the inlet of the second chamber 103 and, where the second valve 112 is in position 1, into the collection reservoir, e.g., metered groove of the second valve 112.

Step 6: After the second centrifugation cycle, after the centrifuge has stopped, remove the separator/concentrator device from the centrifuge and manually operate by pushing the second valve 112 to a second position (e.g. position 2) to align the collection reservoir, e.g., metered groove of the second valve 112 with the inlet of the third chamber 153 to allow a clear flow passage from the collection reservoir, e.g., metered groove of the second valve into the third chamber 105 as shown in FIGS. 2B and 4D. A rod can be used to reach the valve in the channel.

Step 7: Replace the separator/concentrator device into the centrifuge. Start a third centrifugation cycle for 5 minutes at 3000 rcf to move the particulate material from the collection reservoir, e.g., metered groove of the second valve 112 into inlet of the third chamber 105 and to the bottom of this chamber for collection.

Step 8: At the end of the third centrifugation cycle, after the centrifuge has stopped, remove the separator/concentrator device from the centrifuge, access the third chamber 105 and collect the sedimented/concentrated sample.

In some embodiments, the valves of the separator/concentrator device are operated manually after each centrifugation cycle with the aid of an apparatus attached to the device. For example, an actuation device can operate the valves in a sequential order where the actuation device can be physically and operatively attached to the separator/concentrator device described herein. In some embodiments, the actuation device for operating the valve is actuated manually, i.e. by hand, where the valve operating device is a cam sleeve actuating device.

Semi-Manual Actuation of the Valves

In other embodiments, valve operation can be done manually after each centrifugation cycle with the assistance of an actuation device. Such actuation of the valves is referred to herein as "semi-manual actuation", as it requires a user to hand-move an actuation device which actuates the valves in the separator/concentrator device. In some embodiments, valve operation with the actuation device requires manual operation, i.e. by hand. Such actuation devices can be configured to be operatively attached to the separator/concentrator device.

In alternative embodiments, one can use any semi-manual actuation device to operate the valves in the separator/concentrator device, for example, sleeves which allow the valve to be operated, or lip-stick actuation devices commonly known by persons of ordinary skill in the art. In one embodiment, valve operation occurs using an operatively attached cam sleeve actuation device, or other semi-manual actuation device is actuated manually by hand after the stop of centrifugation. In some embodiments, valve operation can be done using a semi-manual actuation device which comprises a rod with a spiral or helical grove, and is configured to fit within a channel with a complementary spiral or helical indentation, so that that a manual twist of the rod in the chamber moves and operates the valve within the separator/concentrator device.

Figure 26:
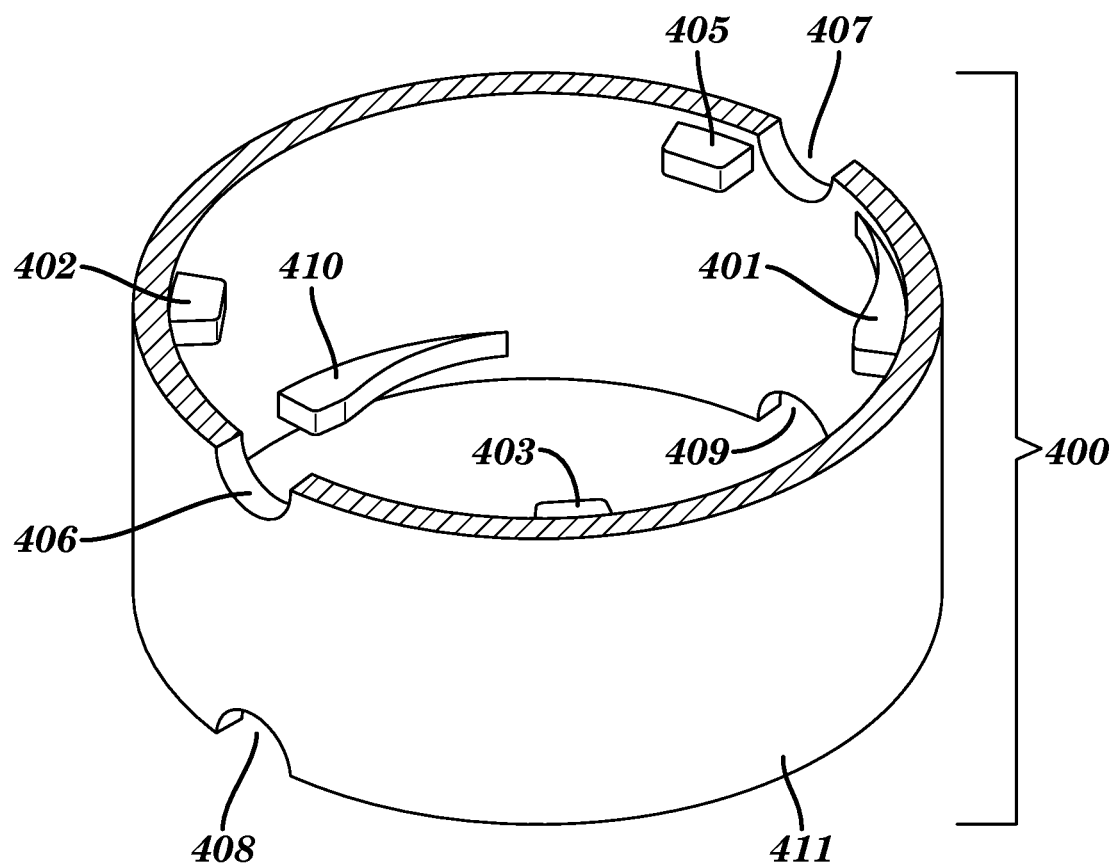
FIG. 26 is a three dimensional prospective image of one embodiment of a semi-manual valve actuator which is a cam sleeve actuator device 400.

In some embodiments, valve operation can be actuated semi-manually, e.g. using a cam sleeve actuation device 400 as disclosed herein. One embodiment of such a cam sleeve device is shown in FIG. 26. In some embodiments, the valve can be actuated using a cam sleeve device 400 which operatively attaches to the disposable separator/concentrator to actuate the valves using a manual rotating or twisting action of the cam sleeve actuation device.

In some embodiments, the cam sleeve actuator device 400 is a rotating a ring around the valve section that actuates the metering valves using internal cams to push the valves 0.1 inches inwards from their starting position. The cam sleeve actuator device 400 has a combination of driving cams 401, 410 and guiding tabs 402, 403, 405, which function as over-rotation-stops. This allows the user to only rotate the cam ring in the allowed direction, eliminating any possibility of actuating the wrong valve first.

Referring to FIG. 26, shows one embodiment of a semi-manual valve actuator which is a cam sleeve actuator device 400 which is suitable for actuating a first valve 111 and a second valve 112 of a separator/concentrator device, where the cam sleeve actuator device 400 has a first cam 401 (cam 1) configured to actuate a first valve 111 in the separator/concentrator device, and a second cam 410 (cam 2) configured to actuate a second valve 112 in the separator/concentrator device. The cam sleeve actuator device 400 also comprises stop tabs 402, 403, 405, which are configured to be located in a the same plane as the upper cam 401 to control the direction and distance of the rotation of the cam sleeve actuation device to actuate the valves in the separator/concentrator device.

In the embodiment of a three-chambered separator/concentrator device, a cam sleeve actuator device 400 is configured to move the first and second valve 111, 112 in their respective channels, a first valve 111 in a first channel 113 that connects the first chamber 101 and second chamber 103, and a second valve 112 in a second channel 114 that connects the second chamber 103 and third chamber 105 as shown in FIG. 4.

The cam sleeve actuator device 400 can surround the separator/concentrator device and in some embodiments, is not physically attached to the device, yet is configured to operate at least one valve when the cam sleeve actuation device is rotated by hand in an appropriate direction.

In some embodiments, a cam sleeve actuator device 400 is configured to sequentially move two valves 111, 112 in a two chamber separator/concentrator device. For example, the cam sleeve actuator device surrounds the second and third chambers 103, 105 of the sleeve actuator device, such that the cams, e.g. the first cam 401 and the second cam 410 are in line with the first valve 111 and second valve 112 in the channels 113, 114 of the separator/concentrator device. For example, the first cam 401 is aligned and can contact and operate the first valve 111 within the first channel 113 that connects the first chamber 101 and second chamber 103, and the second cam 410 is aligned with the second valve 112 within the second channel 114 that connects the second chamber 103 with the third chamber 105.

The following are the exemplary steps for valve operation in a separator/concentrator device having two chambers (FIG. 1) by rotating the cam sleeve actuator device 400 shown in FIG. 26 after each centrifugation cycle.

Figure 27:
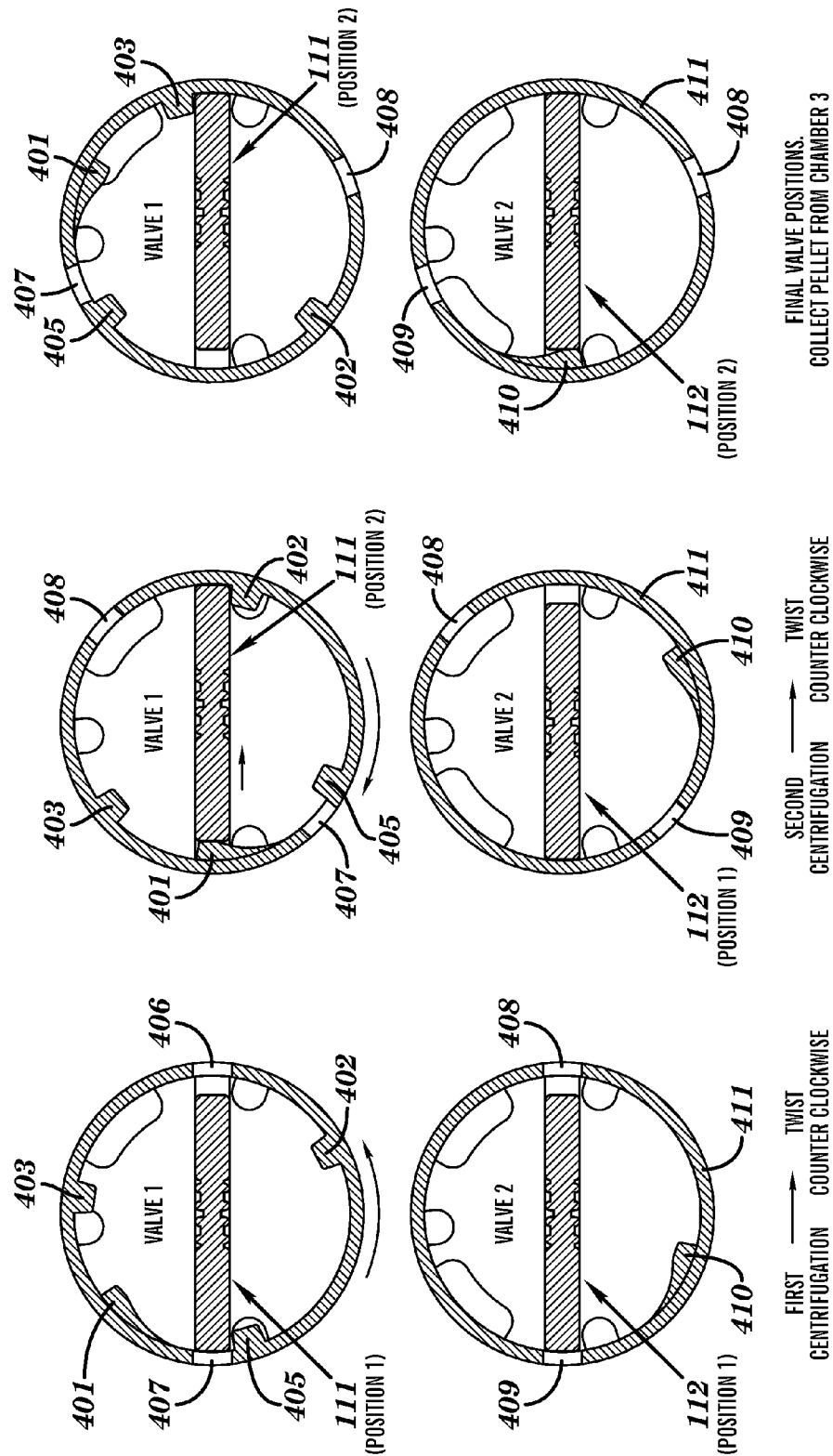
FIGS. 27A-27B are schematic drawings showing the operation of a first and a second valve 111 in a separator/concentrator device from a first position to a second position by the cam sleeve device 400 shown in the embodiment of FIG. 26.
FIG. 27C shows the second cam 410 has connected and actuated the second valve 111 to slide it along the second channel away from the second cam 410, where the first valve has not been moved. The cam sleeve actuator device can not be rotated in a counter-clockwise direction as the first valve 111 contacts the stop tab 402, and thus can only be rotated a clockwise direction. Further, the cam sleeve actuator device can only be rotated a certain distance in a clockwise direction before the first valve 111 contacts the stop tab 403 preventing further clockwise rotation of the cam sleeve actuator. It is in this configuration (e.g. the first and second valves are both in position 2) that a third centrifuge cycle occurs.

Step 1. As shown in FIG. 27, the cam sleeve actuator device 400 is positioned around part of the separator/concentrator device so that it is orientated such that the first valve 111 is in the first position for the first centrifuge cycle, e.g. the collection reservoir is aligned with the outlet of the first chamber for collecting the pellet in the metered valve.

Step 2: Load the first chamber 101 with the fluid sample to be separated and/or concentrated. Cap the top of this chamber to avoid spillage during centrifugation.

Step 3: Place the separator/concentrator device into a centrifuge. Start a first centrifugation cycle for 5 minutes at 3000 rcf to sediment the particulate matter in the first chamber 101, the particulate matter will sediment towards the outlet at the bottom of the first chamber and into valve-collection reservoir in the first valve 111.

Step 4: At the end of the first centrifugation cycle, after the centrifuge has stopped, remove the separator/concentrator device with the cam sleeve actuation device 400 from the centrifuge and manually rotate the cam sleeve actuation device 400 in an anti-clockwise direction so that the first cam 401 comes into contact and pushes the first valve 111 from position 1 to a second position (position 2) in the channel so the valve-collection reservoir is aligned with the inlet of the second chamber 103 to allows a clear flow passage from the valve-collection reservoir of the first valve 111 to the inlet of the second chamber 103 as shown in FIGS. 2B and 4D.

By way of example, the second cam 401 connects and operates the first valve 111 to slide it along the channel 113 away from the first cam 401. The second valve 112 has not been operated by the cam sleeve actuator device at this time. It is in this configuration the second centrifuge cycle occurs. The cam sleeve actuator device can not be rotated in a clockwise direction as the valve 111 contacts the stop tab 405, and thus can only be rotated a counter-clockwise direction. Further, the cam sleeve actuator device can only be rotated a certain distance in an counter-clockwise direction before the valve 111 contacts the stop tab 402 preventing further counter-clockwise rotation of the cam sleeve actuator.

Step 5: Replace the separator/concentrator device with the attached cam sleeve actuation device 400 back into the centrifuge. Start a second centrifugation cycle for 5 minutes at 3000 rcf to move the particulate material from the valve-collection reservoir of the first valve 111 into the second chamber 103 and to the metered groove of the second valve.

Step 6: After the second centrifugation cycle, after the centrifuge has stopped, remove the separator/concentrator device and the attached cam sleeve actuation device 400 from the centrifuge and manually rotate the cam sleeve actuation device 400 in a clockwise direction to push the second valve 112 to a second position (position 2) in the channel 114 so the valve collection reservoir is aligned with the inlet of the third chamber, to allow a clear flow passage from the collection reservoir of the second valve 112 to the third chamber 105 for final collection as shown in FIGS. 2C and 4E.

FIG. 27C shows the second cam 410 has connected and operated the second valve 112 to slide it along the channel away from the second cam 410, where the first valve has not been operated by this cam movement. The cam sleeve actuator device can not be rotated in a counter-clockwise direction as the first valve 111 contacts the stop tab 402, and thus can only be rotated a clockwise direction. Further, the cam sleeve actuator device can only be rotated a certain distance in a clockwise direction before the first valve 111 contacts the stop tab 403 preventing further clockwise rotation of the cam sleeve actuator.

Step 7: Replace the separator/concentrator device with the attached cam sleeve actuation device 400 into the centrifuge. Start a third centrifugation cycle for 5 minutes at 3000 rcf to move the particulate material from collection reservoir of the second valve 112 into the inlet of the third chamber 105 and to the bottom of this chamber for collection.

Step 8: At the end of the third centrifugation cycle, after the centrifuge has stopped, remove the separator/concentrator device and the cam sleeve actuation device from the centrifuge, access the third chamber 105 and collect the sedimented/concentrated sample.

In alternative embodiments, other devices for semi-manual actuation of the valves in the separator/concentrator device are encompassed, for example, using a device which functions as a sleeve surrounding the valves which functions like a lip-stick twist mechanism to move the valves. In another embodiment, a semi-manual actuation device can comprise a sleeve around the valves which comprises buttons or levers to actuate the valves in a sequential order at appropriate timepoints in the separation method.

Automatic Actuation of the Valves

In other embodiments, valve operation in the separator/concentrator device can be performed automatically, e.g. using an automatic actuator device. In some embodiments, an automatic actuator device can be configured to be operatively attached to the disposable device, and thus is centrifuged along with the separator/concentrator device and is configured to operate the valves during the deceleration phase of the centrifuge cycle. Such a suitable automatic actuator device is an inertial actuation device as disclosed herein.

In alternative embodiments, valve operation in the separator/concentrator device can occur using an automatic actuator device located in a purpose-build centrifuge. In some embodiments, the valve operation occurs automatically using an external arm located in a specially adapted centrifuge where the valve is actuated after a complete stop of the centrifuge.

Automatic Actuation—Inertial Activation Devices

In one embodiment, the valves are operated automatically, for example by an operatively attached actuation device, e.g. an inertial actuation device as disclosed herein. In one embodiment, the actuation device operates with a piston. In one embodiment, the valves are operated using an inertial actuation device during deceleration in a centrifuge. During deceleration, the inertial actuation device pushes a piston against the valve in the separation device thereby operating the valve in the channel. In some embodiments, the valves are operated automatically, for example during centrifugation, for example, during the centrifugation deceleration. For example, in a three-chambered device where there are two valves, the valves are operated sequentially, the first valve 111 is moved during deceleration in a first centrifugation, and the second valve 112 is moved during deceleration in a second subsequent centrifugation. In some embodiments, the inertial actuation device can be used in a purpose-built centrifuge.

Figure 13:
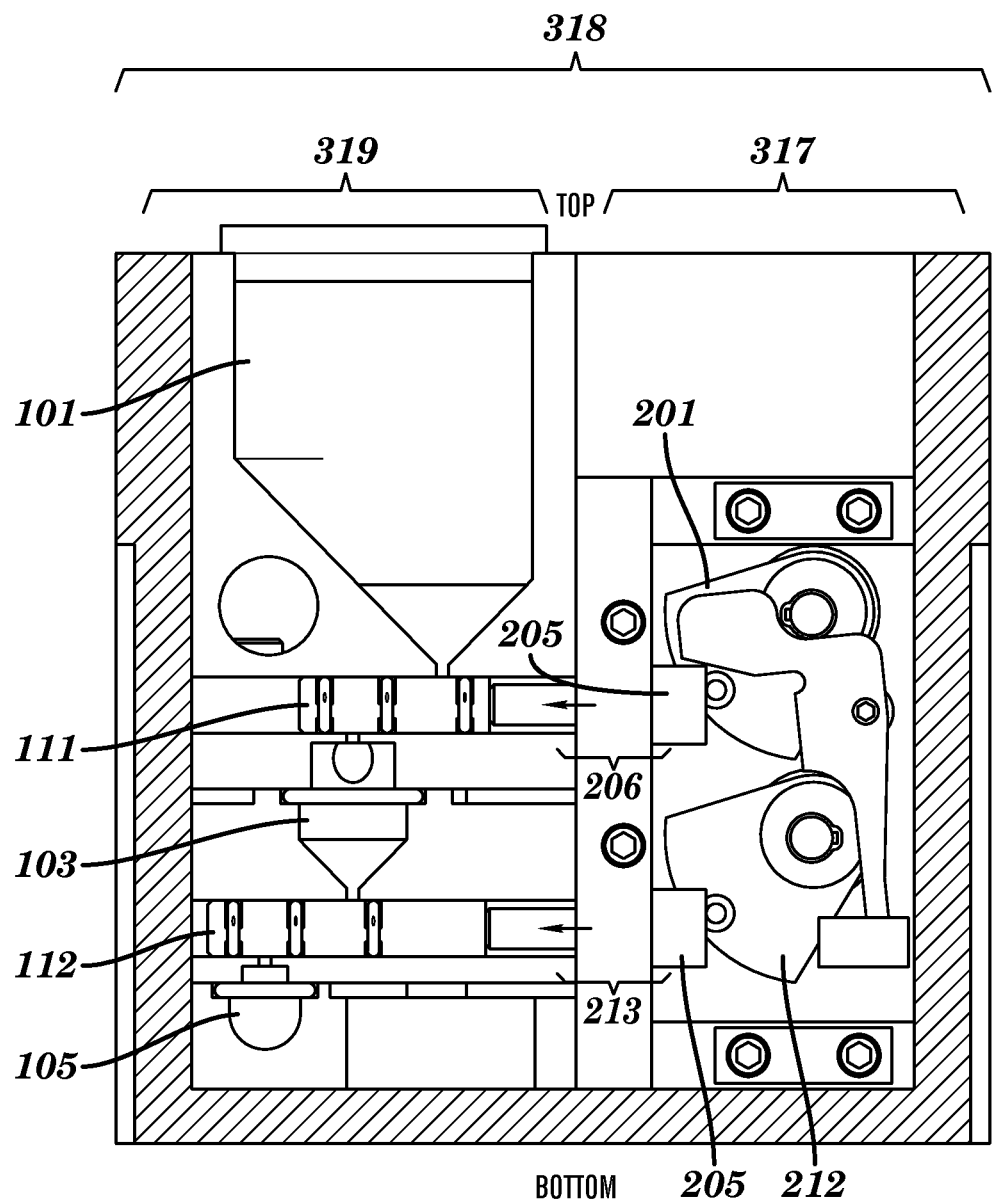
FIG. 13 is a line drawing of a perspective view of the separator/concentrator device 319 of FIG. 2 which is configured to be operatively attached to an inertial actuation device which comprises a piston valve actuator 317 to form a combined automatic separation unit 318.
Figure 14B:
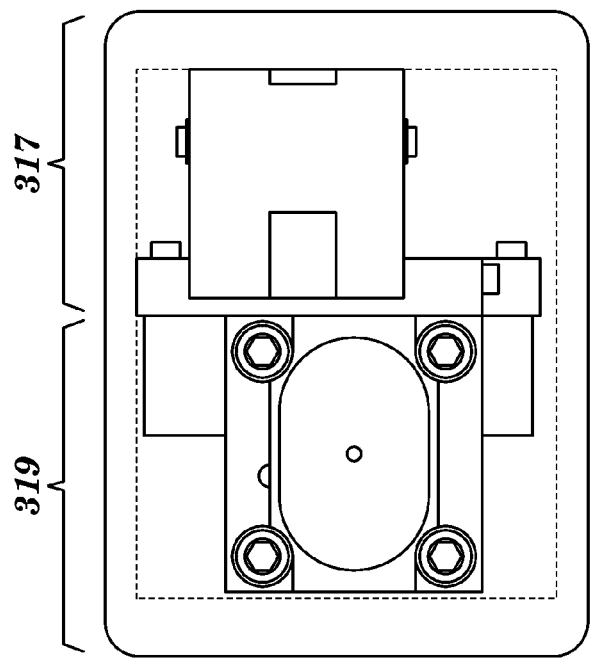
FIG. 14A-14C shows perspective views and a prototype picture of one embodiment of a combined automatic separation unit 318 comprising a separator/concentrator unit 319 and attached an automated actuation device 317 shown in FIG. 13.
Figure 14A:
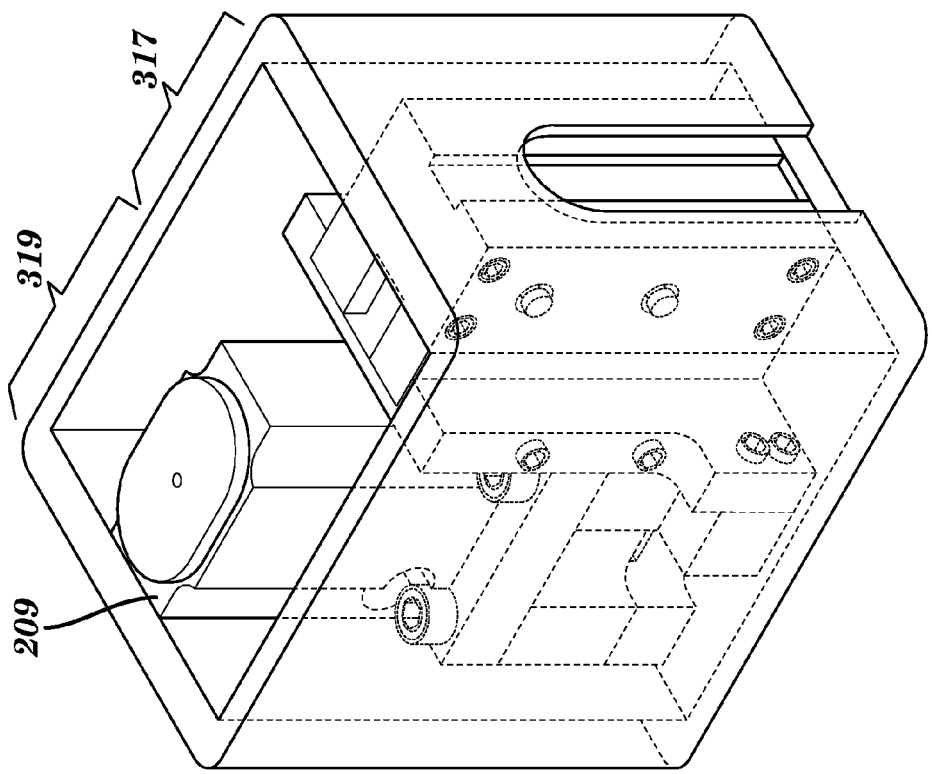
Figure 14C:
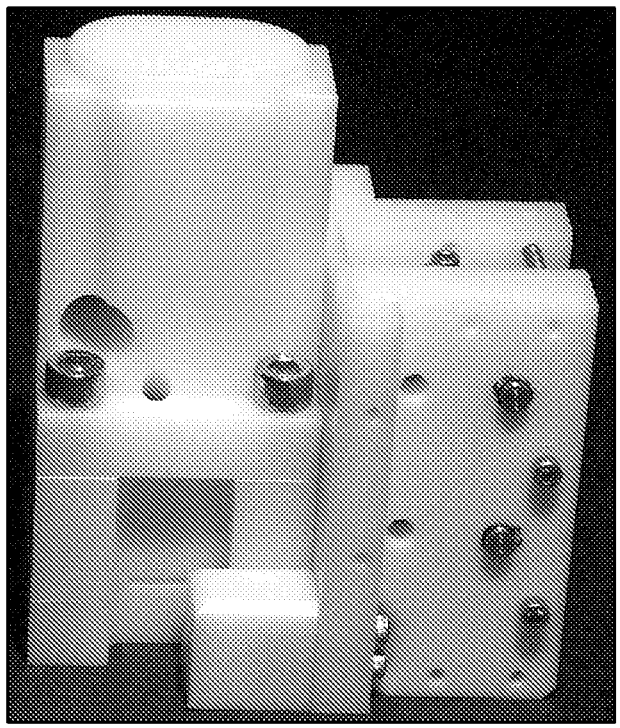

In some embodiments, an inertial actuation device operates the valve automatically, e.g. during the deceleration phase of a centrifugation cycle. In some embodiments, actuation devices comprise pistons that push the valve during the deceleration phase of a centrifugation cycle. In some embodiments, the actuation device is physically and operatively attached to the separator/concentrator device, forming a combined actuator/separator device. Embodiments of such a combined device are shown in FIGS. 13, 14 and 17. In some embodiments, the actuation device is part of a purpose-built centrifuge, wherein the purpose-built centrifuge is specifically adapted to house the separator/concentrator to be in contact with the actuation device in the purpose-built centrifuge during centrifugation.

In the embodiments where the inertial actuation device can be configured to be part of a centrifuge rotor, for example to be internally located in the rotor which holds the separator/concentrator device during the centrifuge cycle. In alternative embodiments, an inertial actuation device can be configured to be part of the bucket which holds the separator/concentrator device. Such embodiments, e.g. configuring a rotor or bucket to house the inertial actuation device allows an ordinary commercially available centrifuge can be adapted to allow automatic actuation of the movable devices in the separator/concentrator device, where the centrifuge is used with the specially adapted rotor or bucket which houses the inertial actuation device.

In one embodiment of the separator/concentrator devices described herein, valve operation occurs automatically during deceleration in a centrifuge. As such, during a first centrifugation cycle, when acceleration is occurring to achieve the targeted gravitational force, the particulates sediment to the bottom of the top chamber. The valve is designed and positioned to tightly seal and block any leakage from this chamber during acceleration and at targeted gravitational force. Tight seals can be achieved by "O" rings on the valve, such as "O" rings made of rubber. After the targeted gravitational force has been maintained for a defined time period, deceleration starts. During deceleration, valve operation occurs allowing a volume of sedimented particulate from the metered groove to enter the chamber below the valve.

In one embodiment of the separator/concentrator devices described herein, valve operation occurs by an operatively attached inertial actuation device. In one embodiment, a separator/concentrator device and an operatively attached inertial actuation device forms a combined separation unit for use with a centrifuge (see FIGS. 13, 14 and 17).

In one embodiment of the separator/concentrator device described herein, valve operation occurs using an actuation device that operates with a piston. The piston pushes the valve in the separation device during deceleration.

For a three chambered separator/concentrator device, there are three chambers: a first, second and third chamber 101, 103, 105, two valves: a first 111 and a second valve 112, and two channels: a first 113 and a second channel 114. In one embodiment of a three chambered device wherein an automatic actuation device is operationally attached, the first valve 111 is operated during deceleration in a first centrifugation cycle, and the second valve 112 is moved during deceleration in a second subsequent centrifugation cycle.

In one embodiment of a separator/concentrator device having three chambers wherein an automatic actuation device is operatively attached, the valves are moved sequentially during deceleration in two consecutive centrifugations.

In some embodiments, valve operation of the separator/concentrator device occurs with the assistance of an actuation device for automatic operation of the valves, e.g. during the deceleration phase of a centrifugation cycle. In some embodiments, the actuation device is physically and operatively attached to the separator/concentrator device. In some embodiments, the actuation device is part of a purpose-built centrifuge, wherein the purpose-built centrifuge is specifically adapted to house the separator/concentrator to be in contact with the actuation device in the purpose-built centrifuge during centrifugation.

Figure 15:
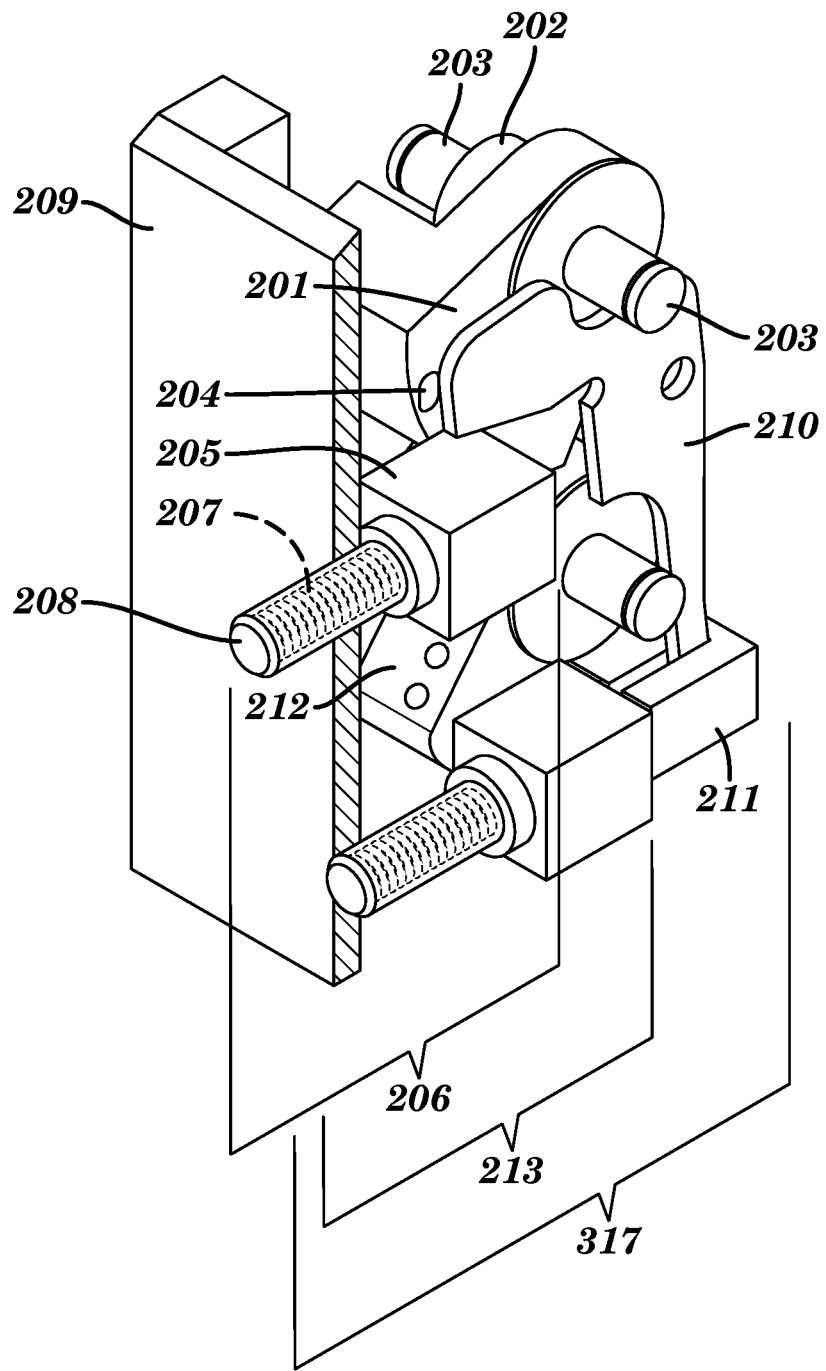
FIG. 15 is a perspective view of one embodiment of an automated actuation device comprising two swing arms 201 and 212 and two moveable actuators 206 and 213 that is used in valve actuation as shown on FIGS. 13 and 14.

An embodiment of an automated actuation device is shown in FIG. 15. Such an automated actuation device is designed to be operatively attached to a separator/concentrator device and operate valves of the separator/concentrator device during the deceleration phase of a centrifugation cycle. In one embodiment, the automated actuation device arms during centrifugal acceleration and actuates during centrifugal acceleration. The automated actuation device comprises a casing 209 housing a swing arm 201, a torsion spring 202, a non-movable shaft 203, a latch 204 on the swing arm 201, and a movable actuator 206 mounted on the casing 209, wherein the swing arm 201 is rotationally attached to the torsion spring 202 and also rotationally attached to the non-movable shaft 203 mounted on the casing 209, wherein the swing arm can swings pivotally from the shaft when experiencing variable centrifugal force during centrifugal acceleration and deceleration, wherein the swing arm 201 rotational pivot off the shaft 203 compresses the torsion spring 202 during centrifugal acceleration, wherein release of compressed energy from the torsion spring 202 during centrifugal deceleration rotates the swing arm 201, wherein the latch 204 is retractable, is retracted during centrifugal acceleration and becomes extended during and when top centrifugation speed is attained, wherein the movable actuator 206 is juxtapose to the swing arm 201 and makes contact with the latch 204 of the swing arm during deceleration, the latch 204 being in the extended state after top centrifugation speed and during deceleration, wherein the movable actuator 206 is moved by a recoil swing of the arm 201 through contact with the latch 204 during deceleration.

Figure 10B:
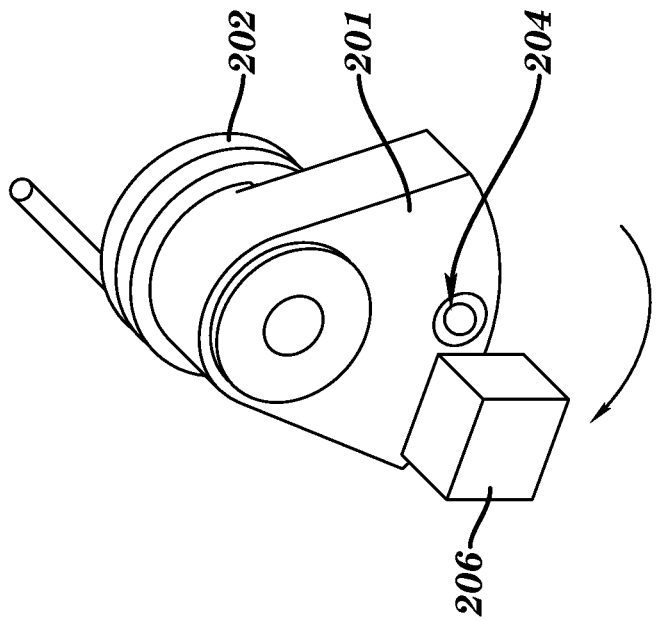
FIGS. 10A-10E show schematic representations of an embodiment of an inertial actuation device for moving the valves of the separator/concentrator device of FIG. 1 and various motions by such device attached to a moveable actuator. The actuation device comprises rotational motion of a swing arm 201.
Figure 10A:
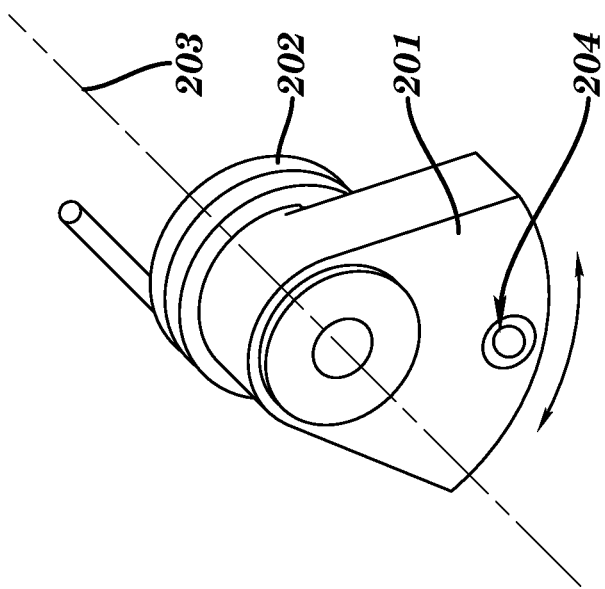

FIGS. 10A and 10B show the orientations, positions and arrangements of the swing arm 201, the torsion spring 202, the latch 204, non-movable shaft 203, a movable actuator 206 and the axis of rotation of the swing arm 201 during a centrifugation run. In FIG. 10B, when the extended latch 204 catches the movable actuator 206 in a recoil backward swing, the movable actuator 206 can be moved backward too.

In some embodiments, the swing arm of an automated actuation device can be any solid object and of various shape that can pivot around the non-movable shaft and compress the attached torsion spring during acceleration and recoil during deceleration.

Figure 10D:
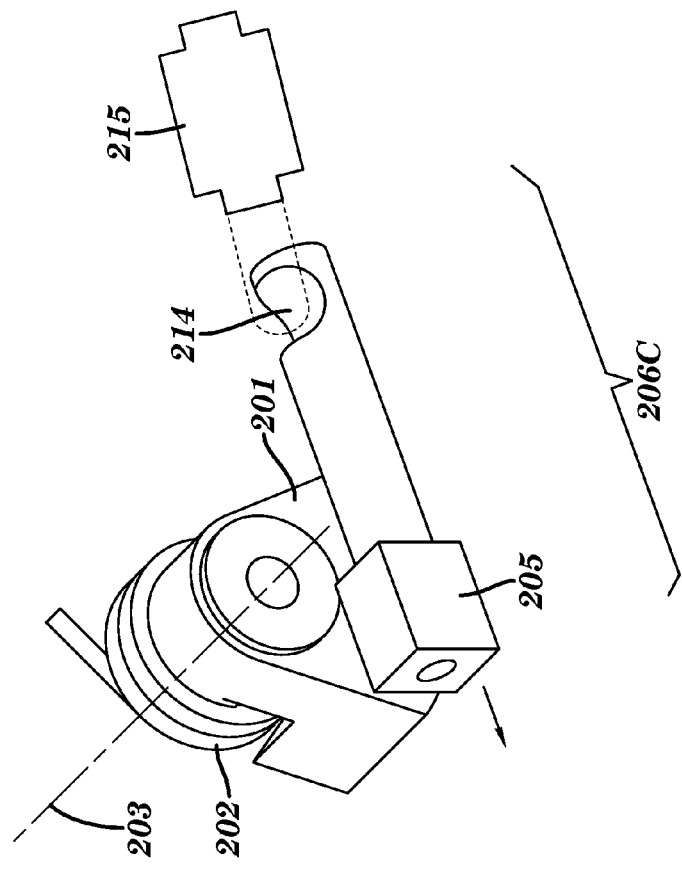
Figure 10C:
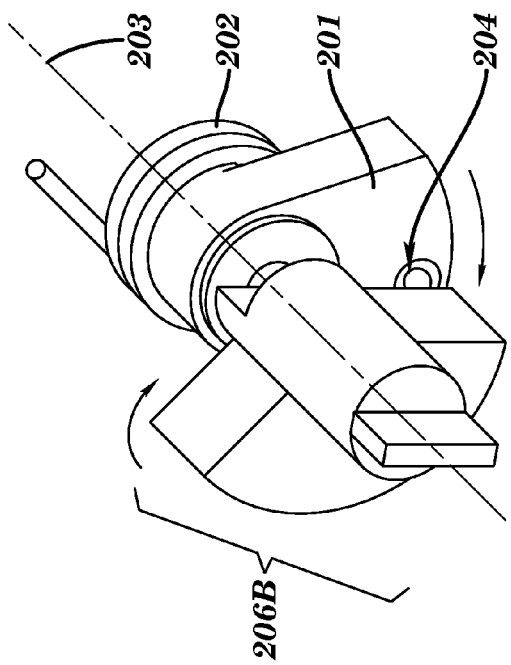
Figure 10E:
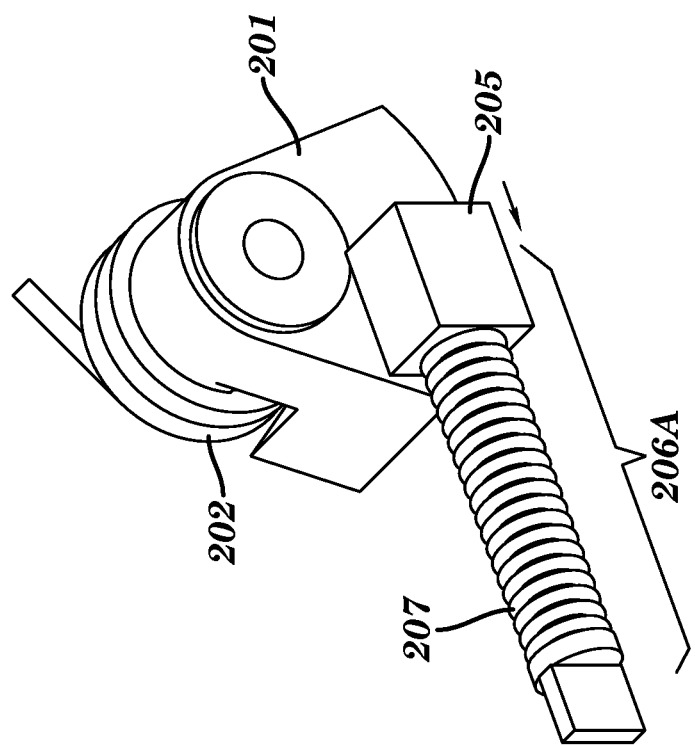

In one embodiment of the automated actuation device, the movable actuator 206 is moved in a linear motion. The linear motion can be a pulling or a pushing motion. FIGS. 10D and 10E are embodiments showing movable actuators for executing linear motions. The movable actuator of FIG. 10D executes a pulling motion. The concave 214 can be attached to any movable part 215. When the swing arm 201 recoils during deceleration, it moves the actuator in such a way that the attached movable part 215 is pulled towards closer to the swing arm 201. The movable actuator of FIG. 10E executes a pushing motion. When the swing arm 201 recoils during deceleration, it pushes the movable actuator away from the swing arm 201.

In another embodiment of the automated actuation device, the movable actuator 206 is moved in a rotational motion. An embodiment showing a movable actuator for executing rotational motion is in FIG. 10C. When the swing arm 201 recoils during deceleration, it rotates the movable actuator around the swing arm 201.

In one embodiment of the automated actuation device, the moveable actuator is a valve actuator; the valve actuator functions to open, close or move a valve.

In one embodiment, the valve actuator is a piston valve actuator, meaning that the actuation process is performed using a piston. Embodiments of the automated actuation devices having piston valve actuators are shown in FIGS. 15, 10E, 11A-F, 12 and 16A-E. An automated actuation device comprises a piston valve actuator comprising a head 205, a light compression spring 207 and a piston 208, wherein the head 205 in attached to the piston 208, wherein the light compression spring 207 encases the piston 208, and wherein the head 205 juxtapose to the swing arm 201.

Figure 11A:
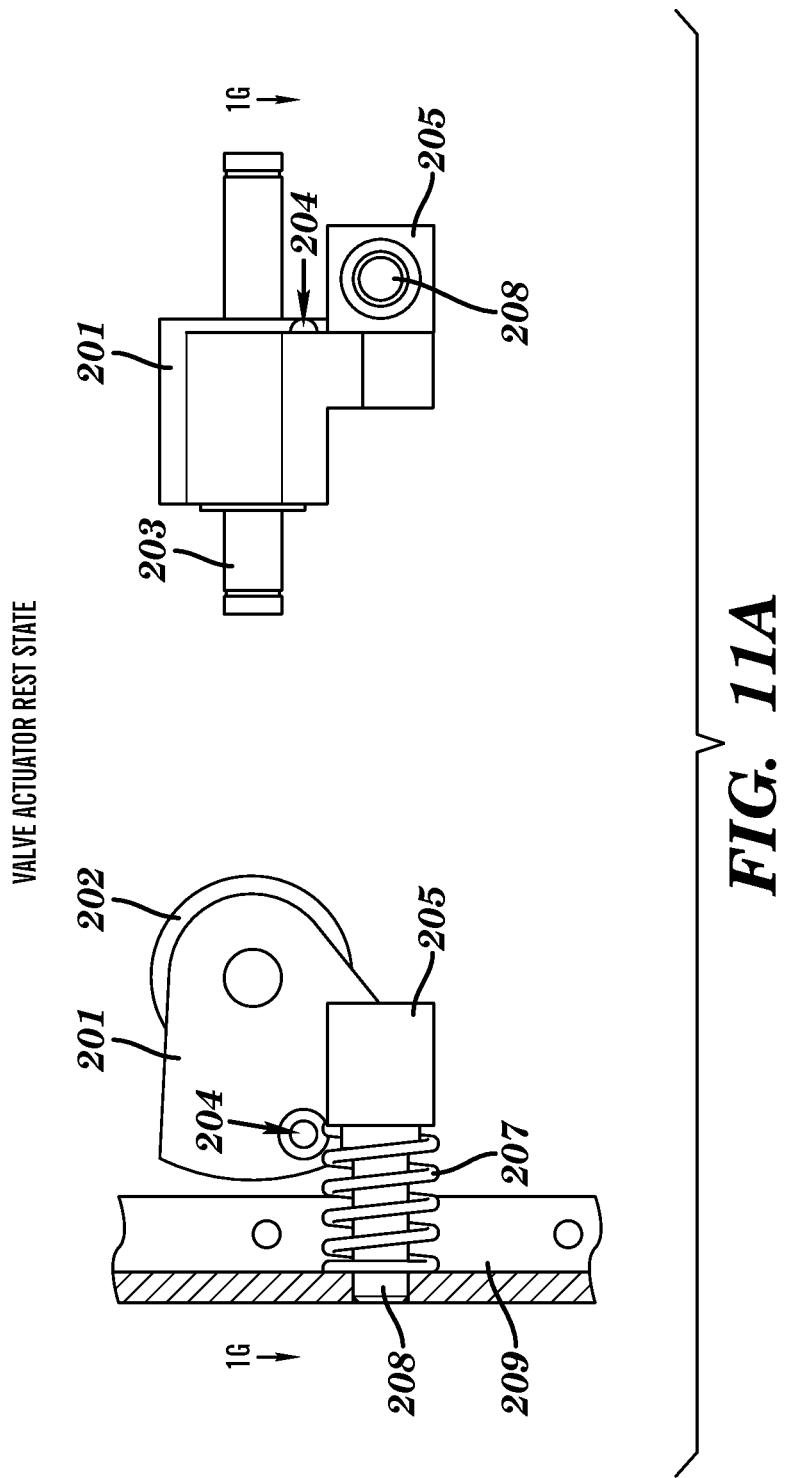
FIGS. 11A-11F illustrate the use of the embodiment of FIG. 10E where the moveable actuator executes a linear pushing motion.

In one embodiment, the movable actuator 206 of the automated actuation device comprises a compression or torsion spring 207. Embodiments of the automated actuation devices having piston valve actuators having compression springs are shown in FIGS. 15, 10E, and 11A. The compression or torsion spring functions to bring the movable actuator back to the starting position after a single actuation is completed, when the swing arm 201 has completed its recoil and the extended latch 204 is not catching the movable actuator 206.

A piston actuation device comprises: a casing 209 housing a swing arm 201, a torsion spring 202, a non-movable shaft 203, a retractable latch 204 on the swing arm 201, and a moveable actuator 206 mounted on the casing 209, the moveable actuator comprising a head 205, a compression spring 207 and a piston 208, wherein the swing arm 201 is rotationally attached to the torsion spring 202 and also rotationally attached to the non-movable shaft 203 mounted on the casing 209, wherein the swing arm can swings pivotally from the shaft when experiencing variable centrifugal force during centrifugal acceleration and deceleration, wherein the swing arm 201 rotational pivot off the shaft 203 compresses the torsion spring 202 during centrifugal acceleration, wherein release of compressed energy from the torsion spring 202 during centrifugal deceleration rotates the swing arm 201, wherein the latch 204 is retractable, the latch is retracted during centrifugal acceleration and becomes extended during top centrifugation speed, wherein the head 205 is juxtapose to the swing arm 201 and makes contact with the latch 204 of the swing arm during deceleration, the latch 204 being in the extended state after top centrifugation speed and during deceleration, wherein the head 205 in attached to the piston 208, wherein the light compression spring 207 encases the piston 208, wherein the head 205 juxtapose to the swing arm 201, and wherein the head 205 is moved by a recoil swing of the arm 201 through contact with the latch 204 during deceleration. Embodiments of a piston valve actuator and the operational orientation with the separation device are shown in FIGS. 13 and 15.

Another embodiment of the automated actuation device is one comprising a top swing arm 201, a bottom swing arm 212, a top movable actuator 206 and a bottom movable actuator 213, wherein each swing arms has a retractable latch 204, wherein one swing arm and latch contacts to one movable actuator, wherein the swing arms and corresponding movable actuators are arranged vertically, one on top of another. Essentially, the automated actuation device has with two swing arms and two corresponding movable actuators instead of one swing arm and one corresponding movable actuator. Such a device can actuate two movable parts or objects during a single centrifugation run, wherein both movable actuators execute simultaneously during deceleration. Alternatively, the movable actuators can execute sequentially in two consecutive centrifugation runs. FIGS. 15 and 16A-E are embodiments of automated actuation devices with two swing arms and two corresponding movable actuators 206 and 213.

One embodiment of the automated actuation device having two swing arms and two corresponding movable actuators comprises a movable latch stop 211, wherein the latch stop 211 is in contact with the bottom movable actuator 213 as shown in FIGS. 15 and 16.

One embodiment of the automated actuation device having two swing arms and two corresponding movable actuators comprises a latch stop release 210, wherein the latch stop release 210 is in contact with the top movable actuator 206 at one end and in contact with the latch stop 211 at the other end, and wherein the actuation of the top movable actuator 206 disengages the latch stop 211 away from the bottom movable actuator 213 as shown in FIGS. 15 and 16.

Figure 11B:
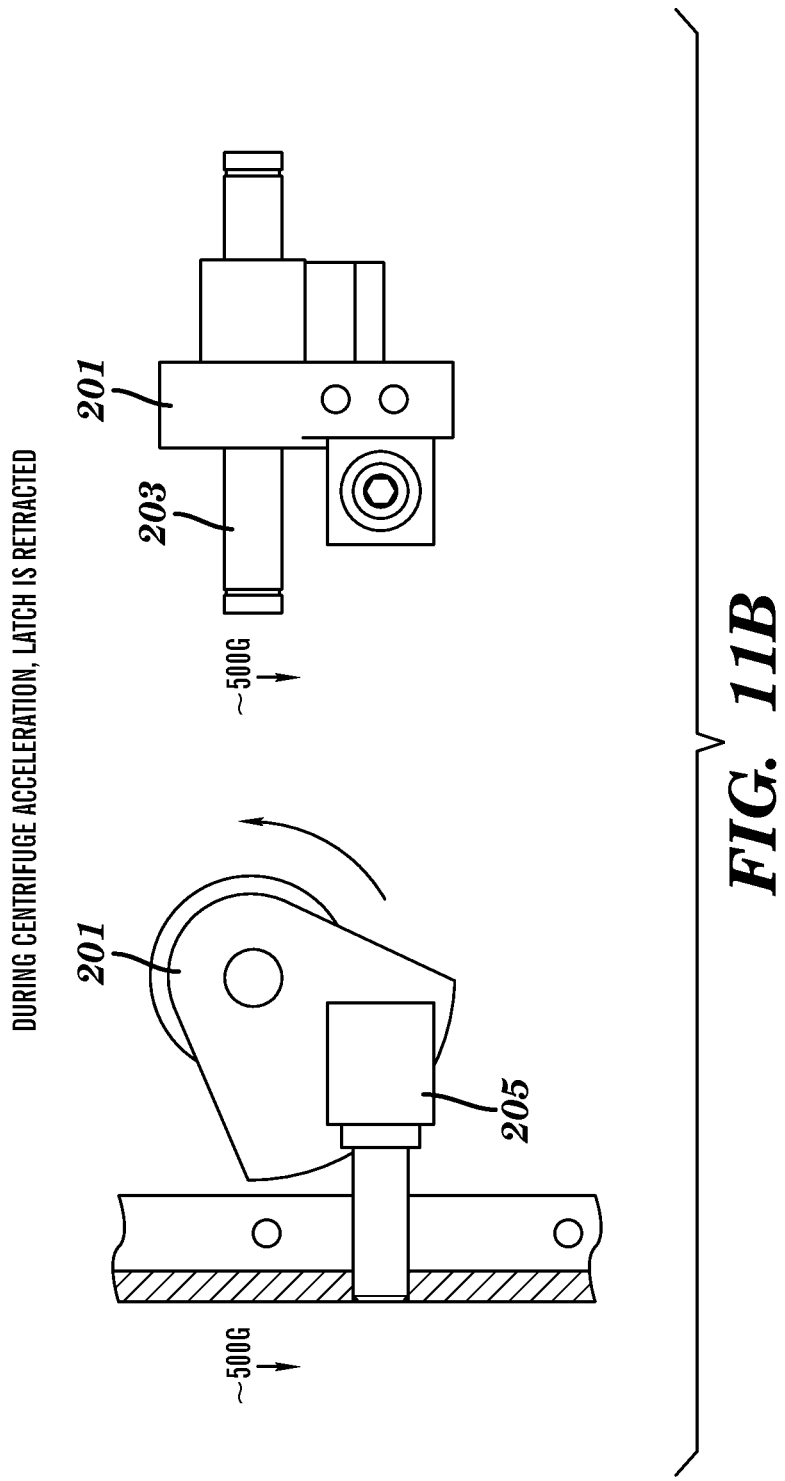
Figure 11C:
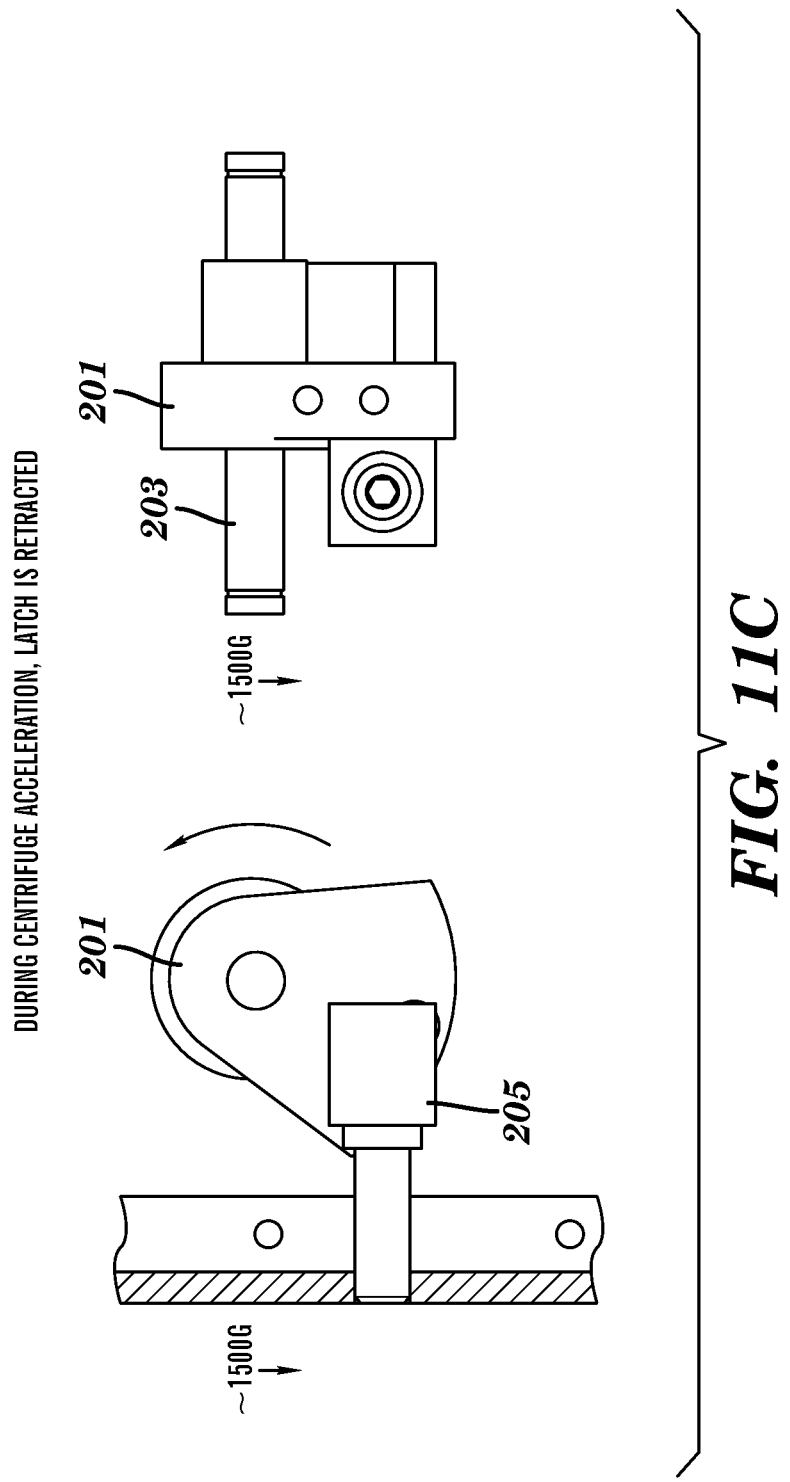
Figure 11D:
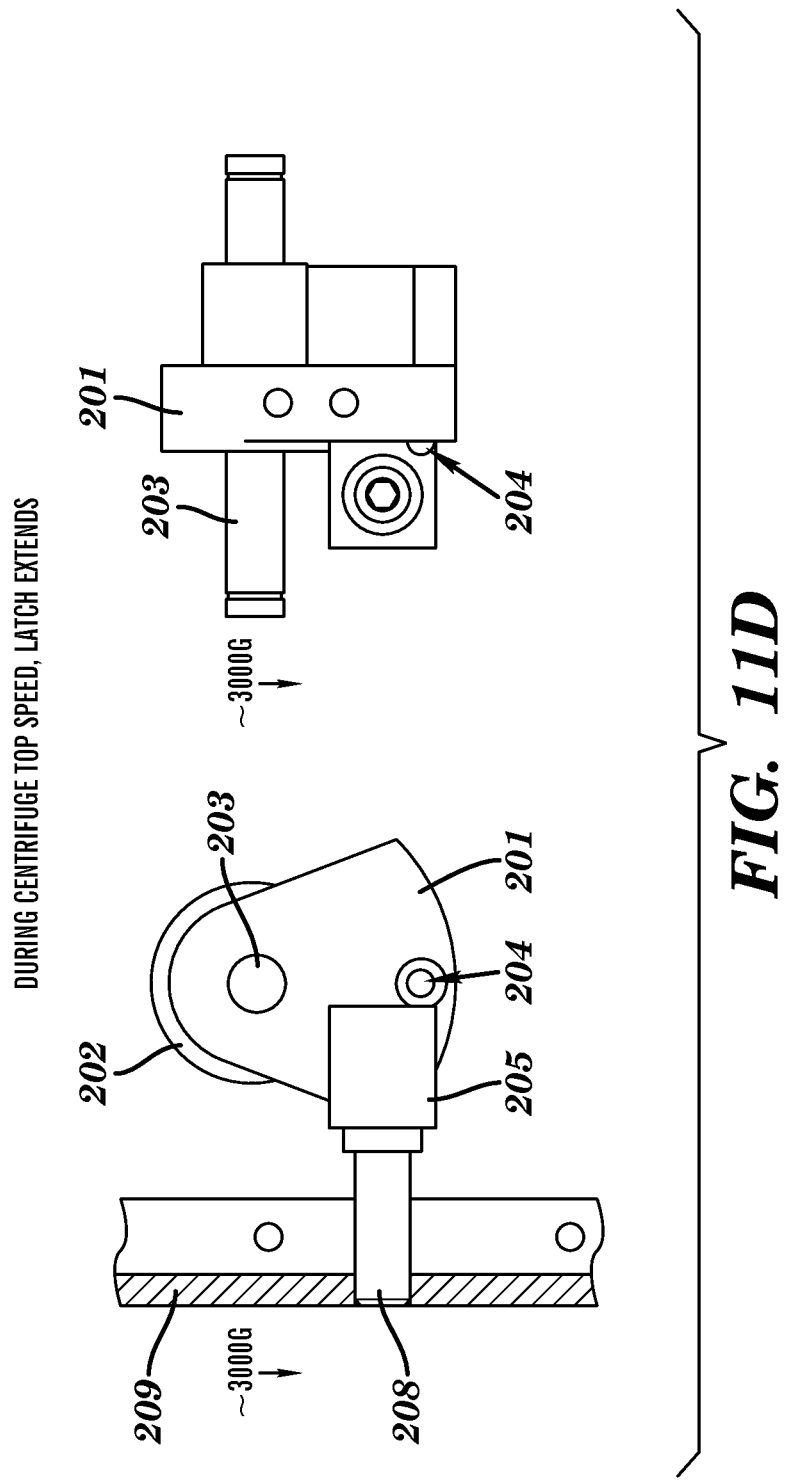
Figure 11E:
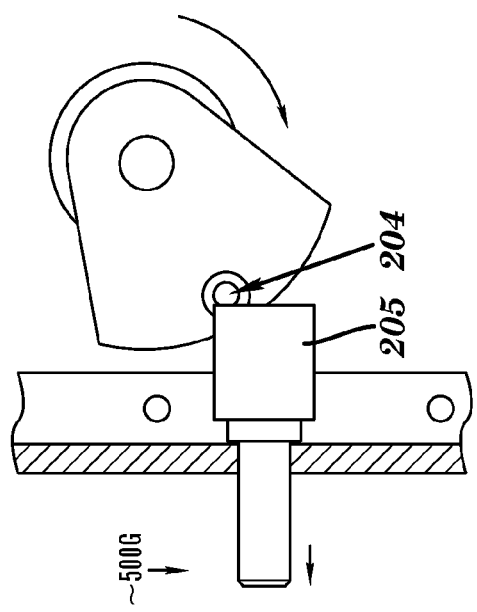
Figure 11F:
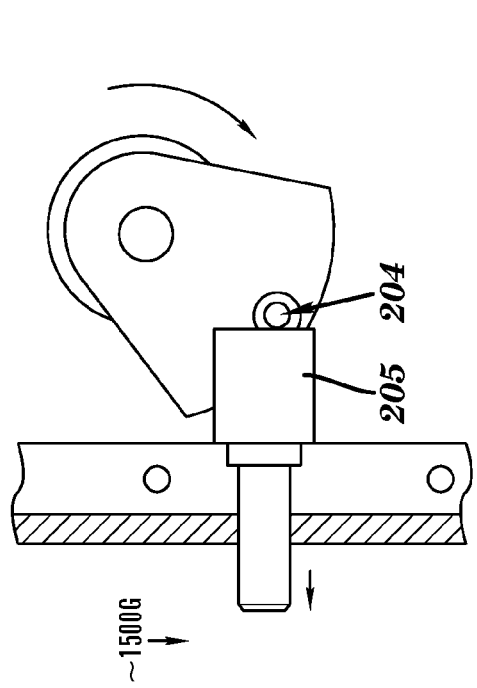

FIG. 11A-F and FIG. 12 illustrate the exemplary workings of an automated actuation device having a single swing arm 201 and one movable actuator 206 which is a piston valve actuator comprising a head 205, compression spring 207 encases a piston 208, wherein the head 205 juxtapose to the swing arm 201 during a single centrifugation run. When the device is at rest or standing at gravitational force, e.g. at ~1 G (FIG. 11A), the latch 204 is retracted such that the swing arm 201 can swing freely right next to the head 205 without moving the head 205 during acceleration, the force generated by the centrifugation rotates the swing arm 201 in a forward direction as shown in FIG. 11B-C. This rotation compresses the attached torsion spring 202. The energy from the force generated by the centrifugation is stored in torsion springs. The swing arm 201 rotates pass the head 205 (FIG. 11D) when the centrifuge reaches top speed and gravitational force of 3000 G during which the latch 204 extends. During centrifuge deceleration, the energy stored in the compressed torsion spring is release to rotate the swing arm 201 in a backward direction as shown in FIG. 11E-F towards its original position. Upon this backward rotation of the swing arm 201, the extended latch 204 now catches the head 205 of the moveable piston valve actuator 206 and pushes the piston 208. This movement of the piston compresses the light compression spring 207. Once the piston 208 has reached the end of its travel, and the latch 204 has disengaged from the head 205 of the movable piston valve actuator 206, and the light compression spring 207 returns the moveable piston valve actuator 206 to the starting position.

FIG. 16A-E illustrate the exemplary workings of an automated actuation device having two swing arms 201 and 212, two moveable actuator 206 and 213, a movable latch stop 211, a latch stop release 210, wherein the moveable actuator are piston valve actuators, each comprising a head 205 that is attached to a piston 208, a compression spring 207 encases the piston 208, wherein the head 205 juxtapose to the swing arm 201 or 212, wherein the latch stop 211 is in contact with the bottom movable actuator 213, wherein the latch stop release 210 is in contact with the top movable actuator 206 at the head 205 at one end of the stop release 210 and in contact with the latch stop 211 at the other end, and wherein the actuation of the top movable actuator 206 disengages the latch stop 211 away from the bottom movable actuator 213 during two consecutive centrifugation runs. The movable actuators 206 and 213 are actuated sequentially during these two consecutive centrifugation runs.

Figure 16B:
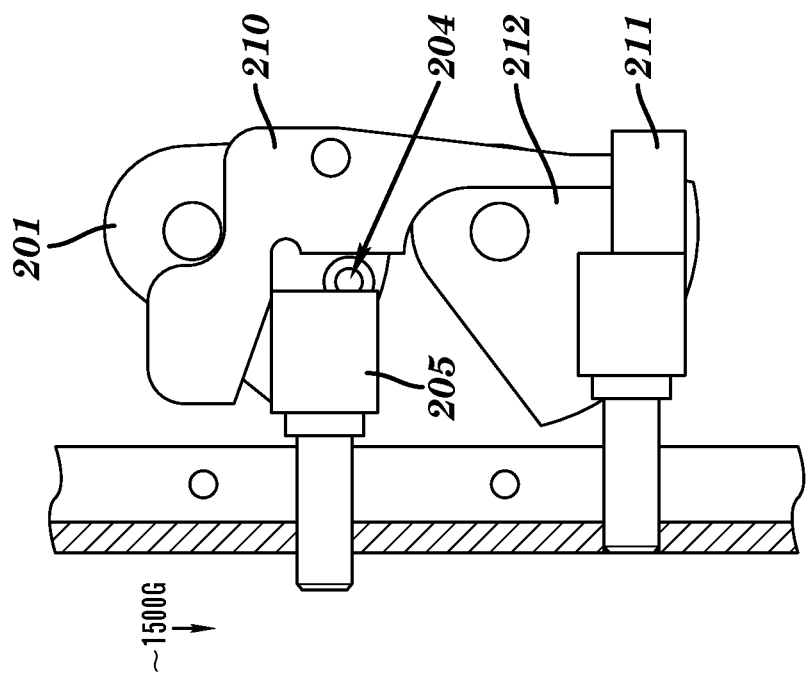
Figure 16E:
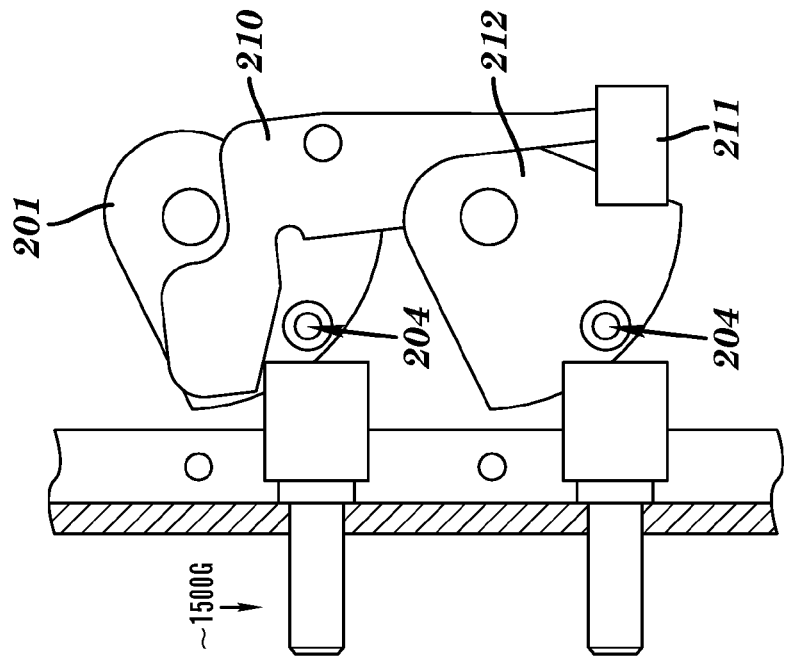
Figure 16D:
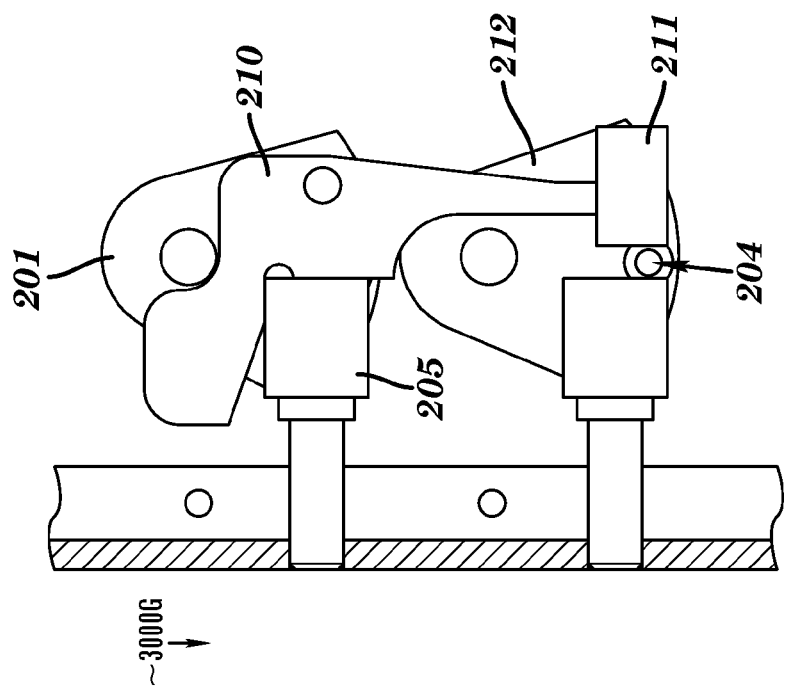
Figure 17A:
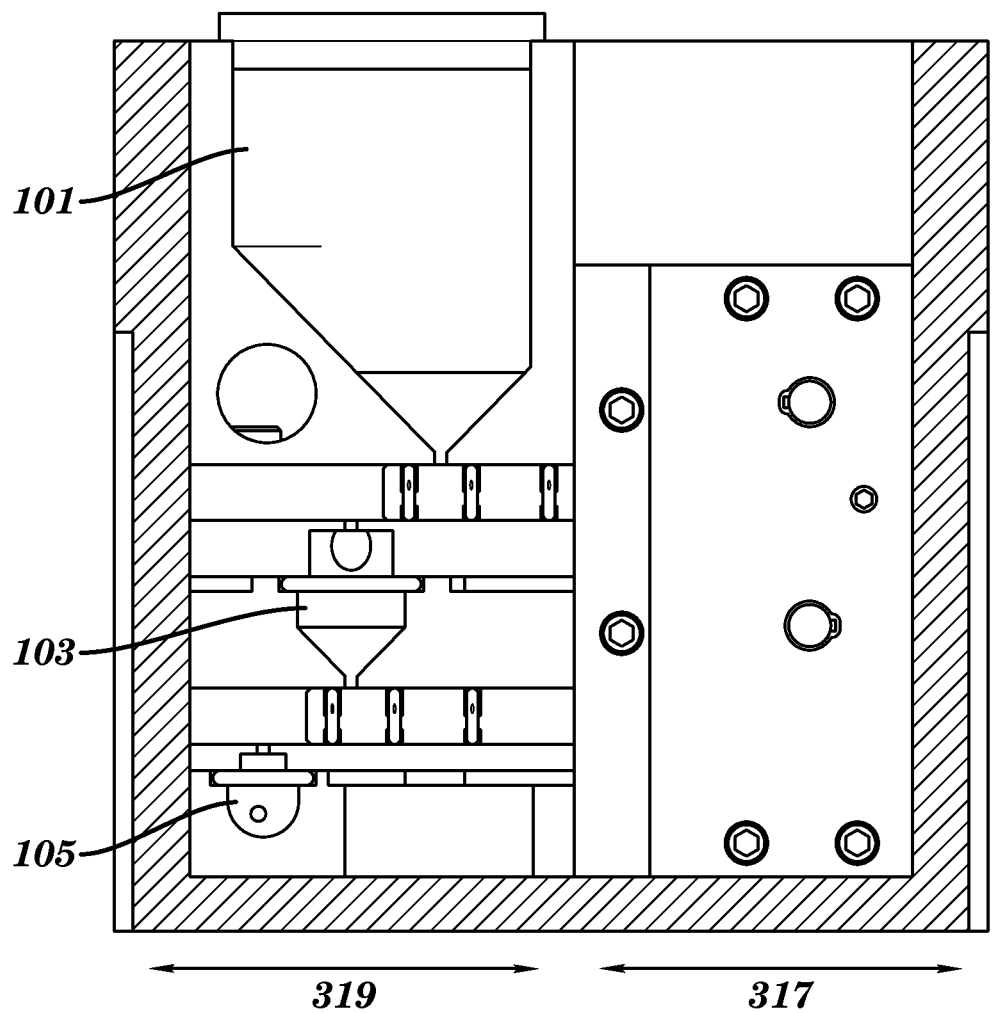
FIGS. 17A-17D illustrate the sequential actuation of the dual mechanical valves in a combined automatic separation device 319 of FIG. 13 using an attached embodiment of two automatic inertial actuator devices shown in FIG. 15A during two consecutive centrifugation cycles.
Figure 17B:
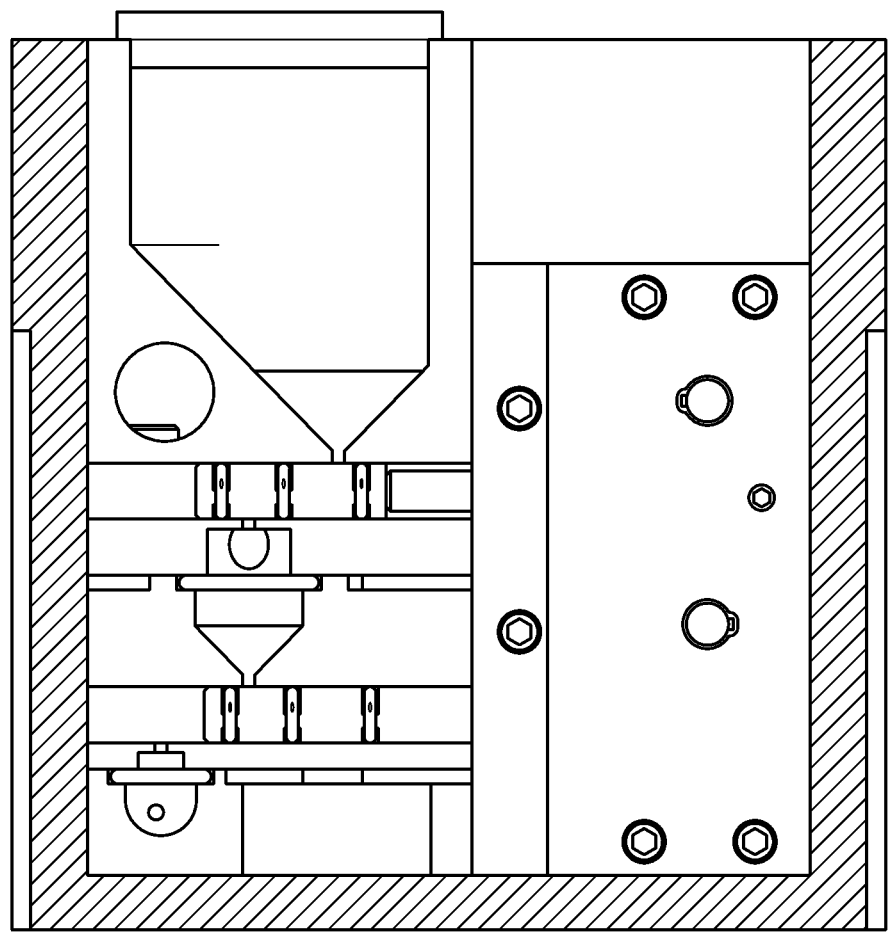
Figure 17C:
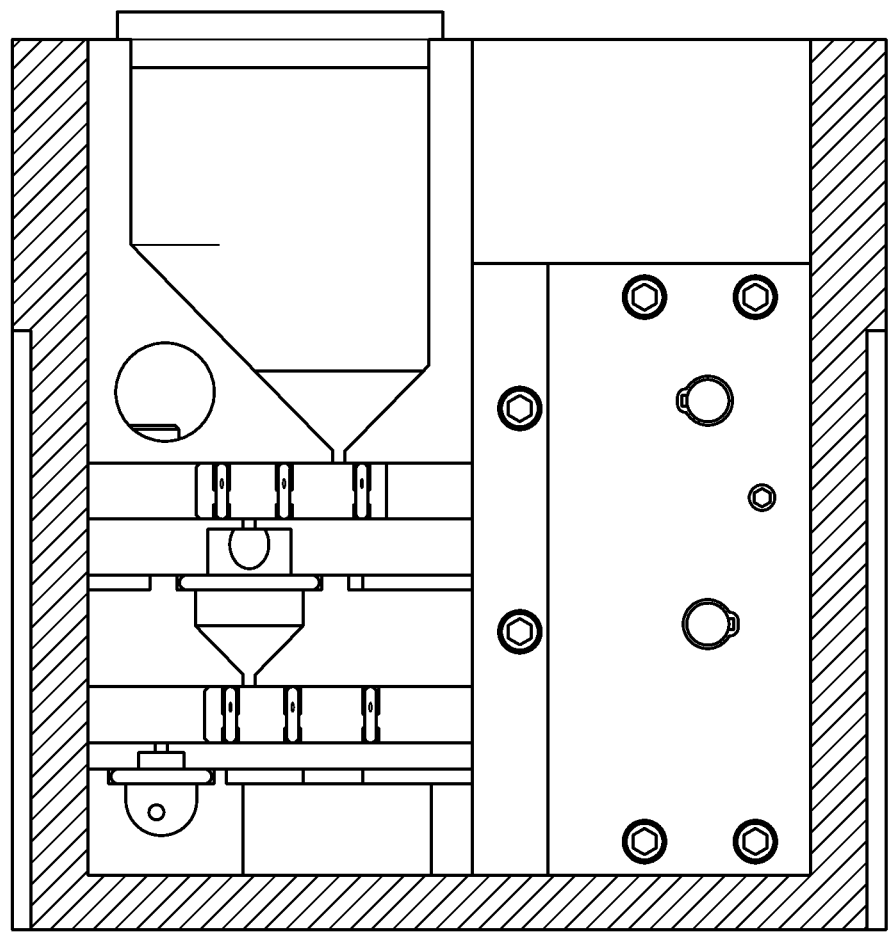
Figure 17D:
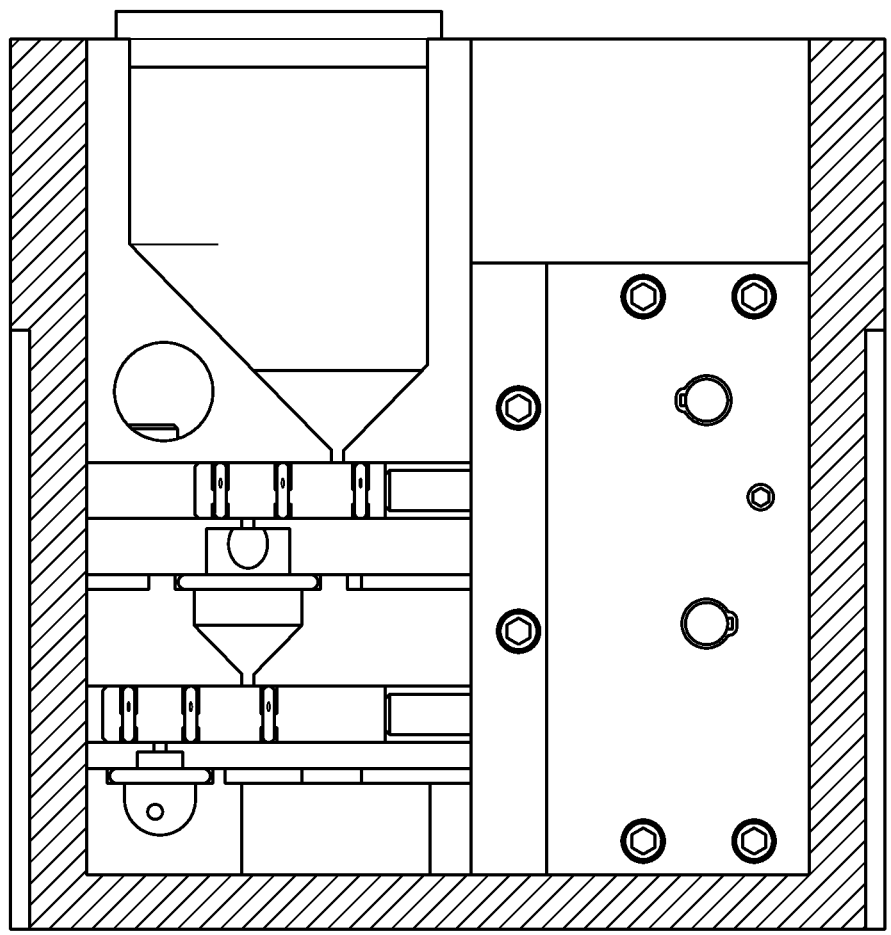

When the automated actuation device is at rest or standing at gravitational force at sea level, the latch 204 of both swing arms 201 and 212 are set in the retracted position. The movable latch stop 211 is aligned directly next to the head 205 of the bottom movable actuator 213. During the first centrifugation cycle, when centrifuge reaches top speed and gravitational force of 3000 G, both swing arms 201 & 212 would have rotated pass their respective heads. The latch of the top swing arm 201 becomes extended. The latch of the bottom swing arm 212 does not extend because it is blocked by the movable latch stop 211 (FIG. 16A). During first centrifuge deceleration (FIG. 16B), the top swing arm 201 actuates the top movable piston actuator 206 as described herein and illustrated in FIG. 11E-F. As the top movable piston actuator 206 completes its motion, the latch stop release 210 pivots and moves the latch stop 211 back and away from the bottom movable piston actuator 213, so the second latch is free to engage during subsequent centrifuge cycles (FIG. 16C-E). The latch stop 211 is manually reset for use of the automated dual actuation device.

For the embodiments illustrated in FIGS. 11 and 16, the movable piston actuators are actuated 0.4 inches inwards from their starting position. Approximately five pounds of force is required. The high centrifugal forces (3000 G). Each valve is actuated by a 10 in-lb torsion spring with 27 g eccentric weight, or swing arm. At full speed, the 27 g swing arm effectively weighs 180 lbs, which "arms" the spring. In other embodiments, the centrifugal forces can be adjusted to the particular torsion spring used and the actuation force required. One skilled in the art can readily adapt the embodiments shown herein for the particular torsion spring used and the actuation force required.

In some embodiments, the actuation device can be constructed of any appropriate material including but are not limited to polymer materials to polyacetal, polyurethane, polyester, polytetrafluoroethylene, polyethylene, polymethylmethacrylate, polyhydroxyethyl methacrylate, polyvinyl alcohol, polypropylene, acetal Copolymer, PEEK, PEVA, Acrylic, polycarbonate, polymethylpentene, polyetherketone, polyphenylene oxide, polyvinyl chloride, polycarbonate, polysulfone, acrylonitrile-butadiene-styrene polyetherimide, polyvinylidene fluoride, and copolymers and combinations thereof. Other preferred materials include polysiloxane, fluorinated polysiloxane, ethylene-propylene rubber, fluoroelastomer and combinations thereof. Other preferred materials include polylactic acid, polyglycolic acid, polycaprolactone, polyparadioxanone, polytrimethylene carbonate and their copolymers.

In one embodiment, the automated actuation device having two swing arms and two corresponding movable actuators is operatively attached to a separator/concentrator device as described herein. Exemplary embodiments are illustrated in FIGS. 13 and 15. The combined automated separation device 318 comprises a separator/concentrator unit 319 and an automatic actuation unit 317. The separator/concentrator unit 319 comprises three chambers; a first chamber 101, a second chamber 103 and a third chamber 105, wherein the first chamber have an inlet opening for sample application into the top chamber, wherein all three chambers connected by channels that are sealed by valves 111, 112, a first valve 111 and a second valve 112 as shown in FIG. 13. The separator/concentrator unit 319 and the automatic actuation unit 317 are physically and operatively attached together to form a combined automated separation device 318 (FIGS. 13 and 14), the positions of the valves 111, 112 are aligned and can be engaged and operated by the movable piston valve actuators 206 & 213.

In one embodiment, the combined automated separation device 318 can be centrifuged in a standard fixed-angle, a swing-bucket, or purpose-built centrifuge.

FIG. 2, FIG. 4, FIG. 16A-F, and FIG. 17A-D illustrate the exemplary workings of a combined automated separation device 318. During the first centrifugation of the combined automated separation device 318, the upper swing arm 201 of the automatic actuation device arms and actuate upper valve when decelerating. In the second centrifugation of the device 318, the lower swing arm 212 of the automatic actuation device arms and actuate upper valve when decelerating.

Automatic Actuation—Purpose-Built Centrifuges with Automatic Activation Devices

In one embodiment, the valves are operated automatically by actuation devices that are part of a purpose-built centrifuge (see, for example FIG. 28). In some embodiments, a centrifuge automatic actuation device 501 can be any mechanism for actuating the valves, for example, where the mechanism includes, but is not limited to, motors, solenoids, pumps, mechanical pumps, levers, air cylinder actuation devices as disclosed herein, which have an external arm which operates each valve in the separator/concentrator device. In such an embodiment, at least one separator/concentrator device is placed in the purpose-built centrifuge such that a centrifuge-attached actuation device 501, e.g. an external arm of the mechanical actuation device can be operatively connected to the disposable separator/concentrator device after each centrifuge cycle. In such embodiments, the valve is operated automatically using the centrifuge-attached actuation devices.

In some embodiments, the valves are moved automatically, for example, where the separator/concentrator device has come to a stop after a centrifuge cycle and is positioned in a location in the centrifuge to be engaged by an external arm of the mechanical actuation device for operation of one or more of the valves. For example, in a three-chambered device where there are two valves, the valves 111, 112 are moved sequentially, the first valve 111 is operated after completion of the first centrifugation, and the second valve 112 is operated after a second subsequent centrifugation.

In one embodiment, the following are exemplary steps for valve operation in a purpose-build centrifuge for automatic operation of the valves in a separator/concentrator device.

Step 1: The separator/concentrator device is inserted into swinging basket 502 hanging from centrifuge rotor 503. All external arms, e.g., a first external arm 504, and a second external arm 505 are reclined and out of the way of the swinging disposable.

Step 2: Centrifuge rotor spins up to 4000 rpm. As rotor spins, due to centripetal force, the disposable and bucket swing out to nearly horizontal. During the (3-10 minute) spin, the blood in the disposable stratifies and any bacteria present pellets at the bottom of the first chamber 101 of the separator/concentrator device, and into the collection reservoir of the first valve 111.

Step 3: As the rotor comes to a controlled stop, the separator/concentrator device is positioned in the centrifuge located next to the backstop 506 in position to be engaged by one of the external arms 504, 505 for valve operation in the separator/concentrator device.

Step 4: The first external arm 504 is mechanically operated to contact the separator/concentrator to push it back into the backstop, where the first external arm 504 is configured to have a protrusion 507 which operates to move the first valve 111 from position 1 to position 2. Valve operation by the first external arm 504 consists simply of mechanically moving the external arm 504 so that the protrusion at the end of the external arm moves the first valve 111 0.1 inch from position 1 to position 2, so that the valve collection reservoir is moved from the output of the first chamber 102 to the input of the second chamber 103 (see FIG. 29).

Step 5: The rotor 503 moves a defined amount in order to position next separator/concentrator device in the centrifuge located next to the backstop 506 in position to be engaged by one of the external arms 504, 505 for valve operation in the separator/concentrator device.

Step 6: Steps 4 and 5 are repeated for each separator/concentrator device in the centrifuge loaded on the rotor 503.

Figure 30:
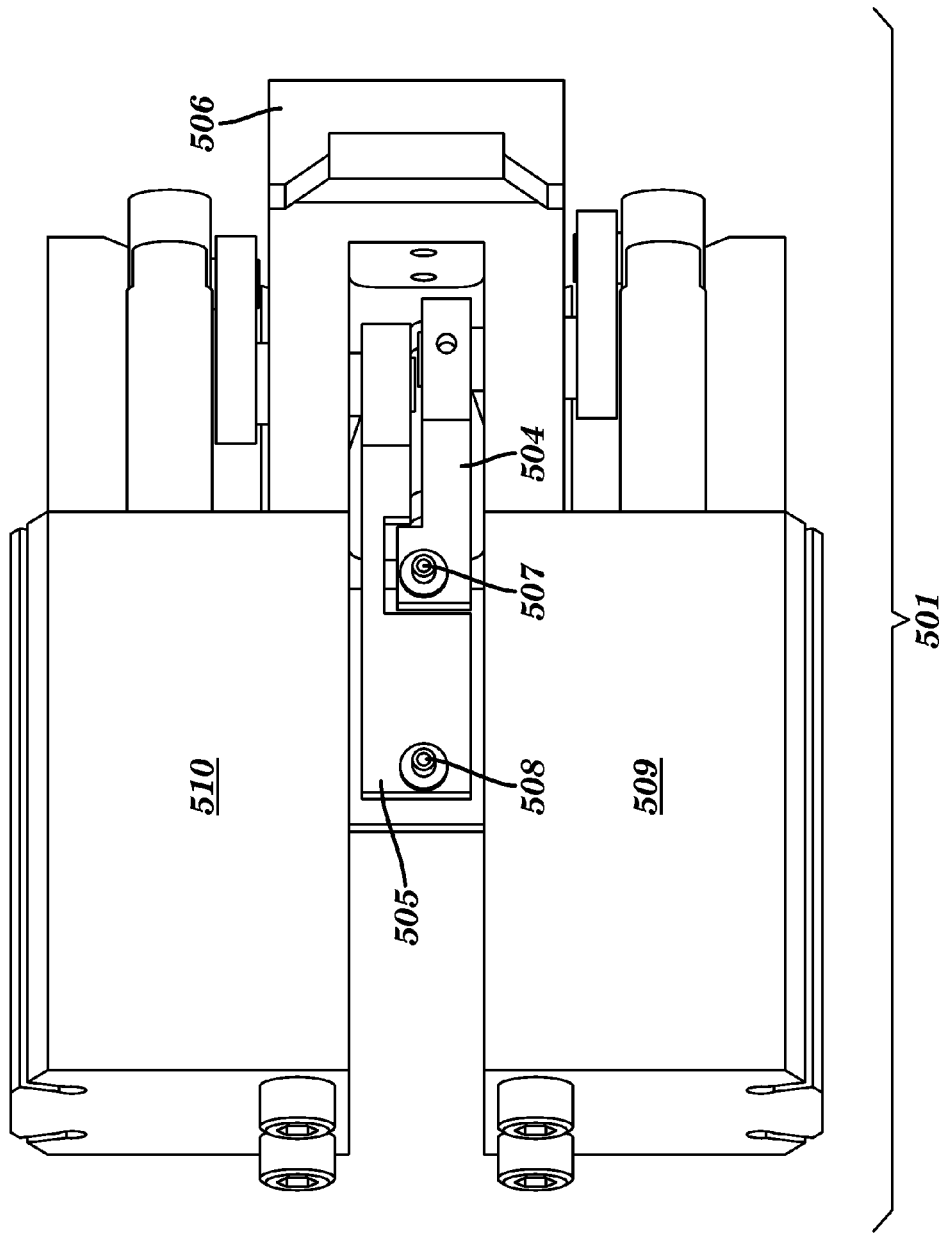
FIG. 30 shows a two-dimensional top view of an embodiment of an automatic actuator 501 shown in FIG. 29.

Step 7: After the first valve 111 operation is completed in all separator/concentrator devices in the centrifuge, the first external arm 504 is mechanically moved to be out of the way during the second centrifuge cycle (see FIG. 30).

Step 8: Centrifuge rotor again spins up to 4000 rpm. During the (1-3 minute) second centrifuge cycle, whatever material transferred by operation of the first valve 111 passes through the second chamber 103 and any particulate, e.g., bacteria, pellets at the bottom of the second chamber 103 and into the second valve 112 where the second valve is in position 1 (e.g., the valve collection reservoir is aligned with the outlet of the second chamber 103).

Step 9: As the rotor comes to a controlled stop after the second centrifuge cycle, the separator/concentrator device is positioned in the centrifuge located next to the backstop 506 in position to be engaged by one of the external arms 504, 505 for valve operation in the separator/concentrator device.

Step 10: The second external arm 505 is mechanically operated to contact the separator/concentrator to push it back into the backstop, where the second external arm 505 is configured to have a protrusion 508 which operates to move the second valve 112 from position 1 to position 2. Valve operation by the second external arm 505 consists simply of mechanically moving the second external arm 505 so that the protrusion at the end of the external arm moves the second valve 112 0.1 inch from position 1 to position 2, so that the valve collection reservoir is moved from the output of the second chamber 103 to the input of the third chamber 105.

Step 11: The rotor 503 moves a defined amount in order to position next separator/concentrator device in the centrifuge located next to the backstop 506 in position to be engaged by one of the external arms 504, 505 for valve operation in the separator/concentrator device.

Step 12: Steps 10 and 11 are repeated for each separator/concentrator device in the centrifuge loaded on the rotor 503. After operation of the second valve 112 is completed on all disposables, the second external arm 505 is positioned in the centrifuge to be out of the way of the third centrifuge spin cycle (see FIG. 30).

Step 13: Centrifuge rotor spins up to 2 or 3000 rpm. During the brief final spin, whatever material in the $2^{nd}$ valve is deposited onto the sample slide. During the final (1-3 minute) third centrifuge cycle, whatever material transferred by operation of the second valve 112 passes through the third chamber 105 and any particulate, e.g., bacteria, pellets at the bottom of the third chamber 105 and into the collection outlet of the third chamber 105.

Step 14: The rotor comes to a stop and the separator/concentrator device is ready to be removed. The concentrated sample can be collected from the separator/concentrator device for subsequent analysis.

In some embodiments, the external arms 504, 505 in a centrifuge controlled automatic actuation device can be moved by any mechanism, for example, where the mechanism includes, but is not limited to, motors, solenoids, pumps, mechanical pumps, levers, air cylinder actuation devices as disclosed herein. In some embodiments, as shown here, the first external arm 504, and second external arm 505 are controlled by a first air pump 509 and a second air pump 510, respectively.

In some embodiments, the centrifuge is programmed to operate the external arms and the centrifuge cycles through steps 1 to 14 above without the need of user. In some embodiments, a purpose-built centrifuge comprising an automatic actuation device 501 is connected to a computer. In some embodiments, a purpose-built centrifuge comprising an automatic actuation device 501 is connected to a user interface and a digital display and a computer. In some embodiments, a system for separation and concentration of a fluid sample comprises a purpose-built centrifuge comprising an automatic actuation device 501, a user interface connected to the purpose-built centrifuge, and a computer.

Figure 29:
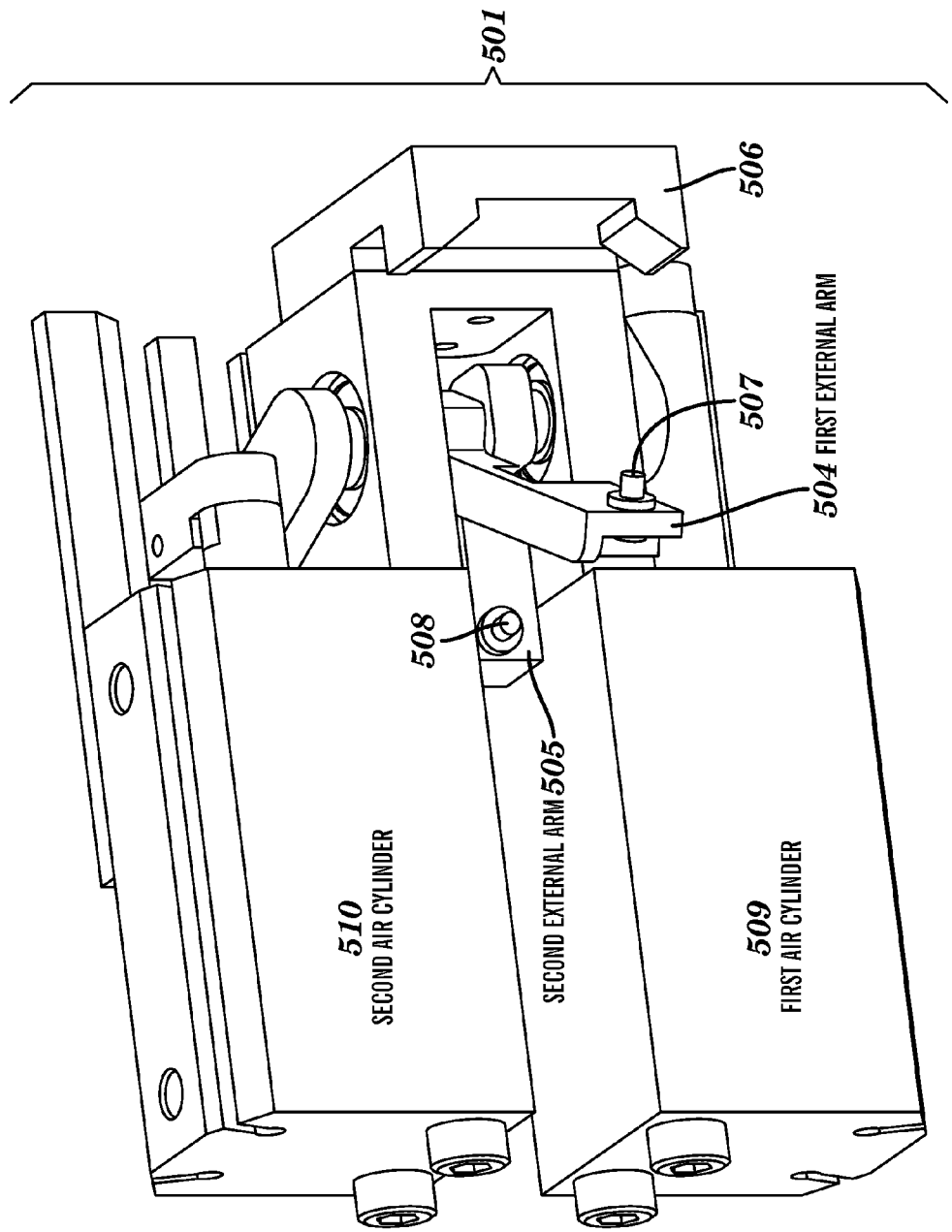
FIG. 29 shows a three-dimensional prospective view of an embodiment of an automatic actuator 501 of the purpose-built centrifuge shown in FIG. 28. Embodied herein is an automatic actuator having two air cylinders as the mechanical means to operate two external arms which are configured to operatively connect with the valves of the separator/concentrator device. In the embodiment shown, the external arm which operatively connects to the first valve is in the position to actuate the first valve.

In some embodiments, a centrifuge controlled automatic actuation device can comprise as many external arms as there are valves in the separation/concentration device, for example, where the separator/concentrator device comprises three chambers and two valves, the centrifuge automatic actuation device 501 can comprise two external arms, e.g., a first and second external arm configured to contact and operate a first valve and a second valve, as disclosed in FIG. 29. In some embodiments, a centrifuge automatic actuation device 501 comprises one external arm 504 which is configured to have a protrusion 507 which can be moved to different defined heights along the external arm shaft, where the protrusion 507 positioned at each defined height of the shaft of the external arm allows the operation of a first valve, 111 or a second valve 112 after sequential first and second centrifuge cycles. For example, an external arm can have a protrusion 507 located at a first height for operation of a first valve 111 from position 1 to position 2, and then the protrusion can be moved to a second height for operation of a second valve 112 from position 1 to position 2. The protrusion 507 on the external arm can be moved to any number of different heights to operate a first valve, a second valve, a third valve, a fourth valve, a fifth valve or more valves, for example in separator/concentrator devices comprising three, four, five, and six or more chambers respectively.

In one embodiment of the methods described herein, the centrifugal force ranges from 100 G to 5000 G. In one embodiment of the methods described herein, the separation system is centrifuged for a time range of 30 seconds to 30 minutes. In other embodiments, the centrifugation time is 2, 5 or 10 minutes.

In some embodiments of the methods described herein, the centrifugation time and speed are: 2 minutes at 500 G, 10 minutes at 500 G, 2 minutes at 3300 G, and 10 minutes at 3300 G.

The separation device described herein can be used to concentrate and isolate live bacteria out of a sample of blood in approximately 10 minutes. The concentrated sample can then be identified using Raman Spectroscopy or other diagnostic techniques commonly known by one of ordinary skill in the art (e.g. PCR, microscopy, biochemical tests, etc.).

The separation device described herein can be constructed and manufacture for use as a disposable separation device having three chambers and two valves. In some embodiments, the firsts chamber, e.g., a sample chamber has a volume capacity of about at least 10 to 100 mL which is sufficient to accommodate 10 mL of blood sample and about 90 ml of blood cell lysis buffer. In such an embodiment, the first chamber funnels down to a first metering valve, when the first valve is in position 1. Once the blood has lysed, and any bacteria in the blood has pelletized in the first metering valve, the first valve is operated from position 1 to position 2, and 5 µL of material is transferred from the first chamber to the second chamber, where the second chamber comprises a dilution buffer or other buffer (e.g. a wash buffer). In some embodiments, the second chamber comprises about 100 µL water, to dilute any lysis buffer transferred by 95%. Bacteria that has been transferred from the first chamber to the second chamber is repelletized with a second centrifugation into a second metering valve. When the second valve is operated from position 1 to position 2, 5 µL of material is transferred to the third chamber, e.g. the collection chamber where the concentrated sample can then be retrieved. In some embodiments, the third chamber is a microscope slide, configured with an indentation to hold the collected concentrated sample, where the slide (e.g. the entire third chamber) can be removed from the concentrator/separator device, and the slide can be used in an instrument, e.g., a microscope for analysis of the concentrated sample.

In alternative embodiments, the first chamber can have a volume of at least about 10-15 ml which is sufficient to accommodate about 10 ml of blood sample and 1-5 ml of blood cell lysis buffer.

In some embodiments, the present invention can be defined in any of the following alphabetized paragraphs:

[A] A device for rapid separation and concentration of particulates from a fluid sample by centrifugation comprising:
  a. two chambers arranged vertically, a top chamber and a bottom chamber, wherein the top chamber have an inlet opening for a first fluid sample application into the top chamber,
    wherein the top chamber and bottom chamber are physically separated but connected by a channel, and
    wherein the channel is sealed by a valve;
  b. a channel connecting the two physically separated chambers; and
  c. a valve housed within the channel wherein the valve forms a tight seal preventing any direct material flowing from the top chamber to the bottom chamber.

[B] The device of paragraph [A], further comprising a third chamber between the top and bottom chambers, wherein all three chambers are physically separated but connected by channels that are sealed by valves, a upper valve and a lower valve.

[C] The device of paragraph [A] or [B], wherein moving the valve within the channel allows a volume from the chamber above the valve into the chamber below the valve.

[D] The device of paragraph [C], wherein the valve is moved during deceleration in a centrifuge or after the centrifuge has stopped.

[E] The device of paragraph [B], wherein the valves are moved sequentially.

[F] The device of paragraph [E], wherein the upper valve is moved during deceleration in a first centrifugation, and the lower valve is moved during deceleration in a second subsequent centrifugation.

[G] The device of any of paragraphs [A]-[F], wherein the valve is moved by an operatively attached actuation device.

[H] The device of paragraph [G], wherein the actuation device operate with a piston.

[I] The device of any of paragraphs [A]-[H], wherein the valve is a metered valve.

[J] The device of any of paragraphs [A]-[I], wherein the fluid sample has a volume range of 10 nanoliters to 1 liters.

[K] The device of any of paragraphs [A]-[I], wherein the fluid sample has a volume range of 10 milliliters to 100 microliters.

[L] The device of any of paragraphs [A]-[K], wherein the fluid sample is a blood sample.

[M] The device of any of paragraphs [A]-[L], wherein the centrifugation is performed in a fixed-angle, a swing-bucket, or purpose-built centrifuge.

[N] The device of any of paragraphs [A]-[M], wherein any of the chambers contain a second or third fluid sample.

[O] The device of any of paragraphs [A]-[N], wherein the top chamber contains a lysis buffer.

[P] The device of paragraph [O], wherein the lysis buffer lyses blood cells.

[Q] The device of paragraph [A] or [B], wherein the valve is moved manually, without the aid of an actuation device in operative connection with the device.

[R] The device of paragraph [G], wherein the attached actuation device is actuated manually.

[S] The device of paragraph [G], wherein the attached actuation device is actuated automatically during centrifugation in the deceleration.

[T] The device of paragraph [A] or [B], wherein the valve is moved by an actuation device that is part of a centrifuge in which the device is used with.

[U] A system of rapid separation and concentration of particulates from a fluid sample by centrifugation comprising:
  a. a device comprising two chambers arranged vertically, a top chamber and a bottom chamber, wherein the top chamber have an inlet opening for sample application into the top chamber, wherein the top chamber and bottom chamber are physically separated but connected by a channel, and wherein the channel is sealed by a valve; and
  b. a centrifuge.

[V] A system of paragraph [U], wherein the device further comprises a third chamber between the top and bottom chambers, wherein all three chambers are physically separated but connected by channels that are sealed by valves, a upper valve and a lower valve.

[W] The system of paragraph [U] or [V], wherein the device further comprises an actuation device in operative connection with the device to move the valve during deceleration in a centrifuge, allowing a volume from the chamber above the valve into the chamber below the valve.

[X] The system of paragraph [U] or [V], wherein the actuation device operates with a piston.

[Y] The system of paragraph [X], wherein the actuation device is operated manually or automatically.

[Z] The system of any of paragraphs [U]-[Y], wherein the valve is a metered valve.

[AA] The system of any of paragraphs [U]-[Z], wherein moving the valve within the channel allows a volume from the chamber above the valve into the chamber below the valve.

[BB] The system of any of paragraphs [U]-[AA], wherein the valve is moved during deceleration in a centrifuge or after the centrifuge has stopped.

[CC] The system of any of paragraphs [U]-[AA] where there are two valves, the valves are moved sequentially.

[DD] The system of paragraph [CC], wherein the upper valve is moved during deceleration in a first centrifugation, and the lower valve is moved during deceleration in a second subsequent centrifugation.

[EE] The system of any of paragraphs [U]-[DD], wherein the centrifuge is a fixed-angle, a swing-bucket, or purpose-built centrifuge.

[FF] A method of rapid separation and concentration of particulates from a fluid sample by centrifugation comprising:
  a. introducing a fluid sample containing particulates into a top chamber of a device of a separation system, the separation system comprising a device comprising two chambers arranged vertically, a top chamber and a bottom chamber, wherein the top chamber have an inlet opening for sample application into the top chamber, wherein the top chamber and bottom chamber are physically separated but connected by a channel, and wherein the channel is sealed by a valve; centrifuging the separation system in a centrifuge; wherein the valve is moved during deceleration in a centrifuge or after the centrifuge has stopped, allowing a volume from the chamber above the valve into the chamber below the valve;
  b. allowing the separation system to decelerated to a complete stop in the centrifuge; and
  c. collecting the particulates from the bottom chamber of the separation system.

[GG] A method of rapid separation and concentration of particulates from a fluid sample by centrifugation comprising:
  a. introducing a fluid sample containing particulates into a top chamber of a device of a separation system, the separation system comprising a device comprising three chambers arranged vertically, a top chamber, a middle chamber and a bottom chamber, wherein the top chamber have an inlet opening for sample application into the top chamber, wherein all three chambers are physically separated but connected by channels that are sealed by valves, a upper valve and a lower valve; wherein the valves are moved during deceleration in a centrifuge or after the centrifuge has stopped, allowing a volume from the chamber above the valve into the chamber below the valve.
  b. centrifuging the separation system in a centrifuge;
  c. allowing the separation system to decelerated to a complete stop in the centrifuge;
  d. centrifuging the separation system in a centrifuge a second time;
  e. allowing the separation system to decelerated to a complete stop in the centrifuge; and
  f. collecting the particulates from the bottom chamber of the separation system.

[HH] The method of paragraph [FF] or [GG], wherein the device comprises an actuation device in operative connection with the device to move the valve allowing a volume from the chamber above the valve into the chamber below the valve.

[II] The method of paragraph [HH], wherein the actuation device operates with a piston.

[JJ] The method of paragraph [II], wherein the actuation device is actuated manually or automatically.

[KK] The method of paragraph [II], wherein the actuation device is actuated automatically during the deceleration in a centrifuge

[LL] The method of paragraph [II], wherein the actuation device is actuated manually after stopping of the centrifuge.

[MM] The method of paragraph [FF] or [GG], wherein the valve is moved manually after stopping of the centrifuge, without the aid of an actuation device in operative connection with the device.

[NN] The method of any of paragraphs [FF]-[MM], wherein the valve is a metered valve.

[OO] The method of any of paragraphs [FF]-[NN], wherein the top chamber contains a lysis buffer.

[PP] The method of paragraph [OO], wherein the lysis buffer lyses blood cells.

[QQ] The method of any of paragraphs [FF]-[PP], wherein the centrifugal force ranges from 100 G to 5000 G.

[RR] The method of any of paragraphs [FF]-[QQ], wherein the separation system is centrifuged for a time range of 30 seconds to 30 minutes.

[SS] The method of any of paragraphs [FF]-[RR], wherein the fluid sample is a blood sample.

[TT] A automated actuation device that arms during centrifugal acceleration and actuates during centrifugal acceleration comprises:
  a. a casing (209) housing
  b. a swing arm (201)
  c. a torsion spring (202)
  d. a non-movable shaft (203)

e. a retractable latch (204) on the swing arm (201), and
f. a movable actuator (206) mounted on the casing (209),
wherein the swing arm (201) rotationally attached to the torsion spring (202) and also rotationally attached to the non-movable shaft (203) mounted on the casing (209),
wherein the swing arm can swings pivotally from the shaft when experiencing variable centrifugal force during centrifugal acceleration and deceleration,
wherein the swing arm (201) rotational pivot off the shaft (203) compresses the torsion spring (202) during centrifugal acceleration,
wherein release of compressed energy from the torsion spring (202) during centrifugal deceleration rotates the swing arm (201),
wherein the latch (204) is retractable, is retracted during centrifugal acceleration and becomes extended during top centrifugation speed,
wherein the movable actuator (206) is juxtapose to the swing arm (201) and makes contact with the latch (204) of the swing arm during deceleration, the latch (204) being in the extended state after top centrifugation speed and during deceleration,
wherein the movable actuator (206) is moved by a recoil swing of the arm (201) through contact with the latch (204) during deceleration.

[UU] The automated actuation device of paragraph [TT], wherein the movable actuator is moved in a linear motion.

[VV] The automated actuation device of paragraph [TT], wherein the movable actuator is moved in a rotational motion.

[WW] The automated actuation device of paragraph [UU], wherein the linear motion is a pulling or a pushing motion.

[XX] The automated actuation device of paragraph [TT], wherein the movable actuator is a valve actuator.

[YY] The automated actuation device of paragraph [XX], wherein the valve actuator is a piston valve actuator.

[ZZ] The automated actuation devices of any of paragraphs [TT]-[YY], wherein the valve actuator comprises a compression spring or torsion spring.

[AAA] The automated actuation device of paragraph [TT], wherein the piston valve actuator comprising a head (205), a light compression spring (207) and a piston (208), wherein the head (205) is connected to the piston (208), wherein the light compression spring (207) encases a piston (208), wherein the head (205) juxtapose to the swing arm (201).

[BBB] The automated actuation device of any of paragraphs [TT]-[AAA] comprising a top swing arm (201), a bottom swing arm (212), a top valve actuator (206) and a bottom valve actuator (213), wherein each swing arms has a retractable latch (204), wherein one swing arm and latch contacts to one valve actuator, wherein the swing arms and corresponding valve actuators are arranged vertically, one on top of another.

[CCC] The automated actuation device of paragraph [BBB], further comprising a movable latch stop (211), wherein the latch stop (211) is in contact with the bottom valve actuator (213).

[DDD] The automated actuation device of paragraph [CCC], further comprising a latch stop release (210), wherein the latch stop release (210) is in contact with the top valve actuator (206) at one end and in contact with the latch stop (211) at the other end, and wherein the actuation of the top valve actuator (206) disengages the latch stop (211) away from the bottom valve actuator (213).

[EEE] A piston actuation device comprises:
a. a casing (209) housing
b. a swing arm (201)
c. a torsion spring (202)
d. a non-movable shaft (203)
e. a retractable latch (204) on the swing arm (201), and
f. a movable actuator (206) mounted on the casing (209), the actuator comprising a head (205), a compression spring (207) and a piston (208),
wherein the swing arm (201) rotationally attached to the torsion spring (202) and also rotationally attached to the non-movable shaft (203) mounted on the casing (209),
wherein the swing arm can swings pivotally from the shaft when experiencing variable centrifugal force during centrifugal acceleration and deceleration,
wherein the swing arm (201) rotational pivot off the shaft (203) compresses the torsion spring (202) during centrifugal acceleration,
wherein release of compressed energy from the torsion spring (202) during centrifugal deceleration rotates the swing arm (201),
wherein the latch (204) is retractable, the latch is retracted during centrifugal acceleration and becomes extended during top centrifugation speed,
wherein the head (205) is juxtapose to the swing arm (201) and makes contact with the latch (204) of the swing arm during deceleration, the latch (204) being in the extended state after top centrifugation speed and during deceleration,
wherein the light compression spring (207) encases the piston (208),
wherein the head (205) juxtapose to the swing arm (201), and
wherein the head (205) is moved by a recoil swing of the arm (201) through contact with the latch (204) during deceleration.

[FFF] The automated actuation device of paragraph [EEE] comprising a top swing arm (201), a bottom swing arm (212), a top valve actuator (206) and a bottom valve actuator (213), wherein each swing arms has a retractable latch (204), wherein one swing arm and latch contacts to one valve actuator, wherein the swing arms and corresponding valve actuators are arranged vertically, one on top of another.

[GGG] The automated actuation device of paragraph [FFF] further comprising a movable latch stop (211), wherein the latch stop (211) is in contact with the bottom valve actuator (213).

[HHH] The automated actuation device of paragraph [GGG], further comprising a latch stop release (210), wherein the latch stop release (10) is in contact with the top valve actuator head (205) at one end and in contact with the latch stop (211) at the other end, and wherein the actuation of the top valve actuator (206) disengages the latch stop (211) away from the bottom valve actuator (213).

In alternative embodiments, the present invention can be defined in any of the following numbered paragraphs:

1. A device for separation of particulates from a fluid sample by centrifugation, the device comprising:
a first chamber, the first chamber including an upper inlet for receiving a first fluid sample to be processed by device and a lower outlet for discharging material;

a second chamber, the second chamber having an upper inlet;

a first channel connecting the lower outlet of the first chamber to the upper inlet of the second chamber; and a first valve disposed along the first channel wherein the valve forms a seal preventing material in the first chamber from flowing in to the second chamber.

2. The device according to claim 1 wherein the first valve includes a first valve chamber and the first valve can be operated to move between a first position and second position, wherein, at the first position, the first valve chamber is open to the first chamber and can receive the material discharged from the lower outlet of the first chamber, and at the second position, the first valve chamber is open to the upper inlet of the second chamber and can deposit the material into the upper inlet of the second chamber.

3. The device according paragraph 1 wherein the first valve includes a third position wherein the lower outlet of the first chamber is closed and material, in response to centrifugal forces, accumulates in the lower outlet of the first chamber.

4. The device according to paragraph 1 wherein the first value is a metered valve.

5. The device according to paragraph 4 wherein the first value includes a metering groove.

6. A device according to paragraph 1, wherein the second chamber has a lower outlet for discharging material.

7. The device according to paragraph 6, further comprising:
a third chamber, the third chamber including an upper inlet for receiving a fluid sample to be processed by the device;
a second channel connecting the lower outlet of the second chamber to the upper inlet of the third chamber; and
a second valve disposed along the second channel wherein the second valve forms a seal preventing material in the second chamber from flowing in to the second chamber.

8. The device according to paragraph 1 or 7, wherein the second or third chamber is a collection well for collecting the material, where the collection well receives the fluid sample from the inlet of the second or third chamber.

9. The device according to paragraph 8, wherein the second or third chamber is a slide.

10. The device according to paragraph 9, wherein the slide is a microscope slide.

11. The device according to any of paragraphs 8, 9 or 10, wherein the second or third chamber comprising a collection well can be removed from the device for analysis of the sample in the second or third chamber.

12. The device according to paragraph 7, wherein the second valve includes a second valve chamber and the second valve can be operated to move between a first position and second position, wherein, at the first position of the second value, the second valve chamber is open to the second chamber and can receive the material discharged from the lower outlet of the second chamber, and at the second position of the second valve, the second valve chamber is open to the upper inlet of the third chamber and can deposit the material into the upper inlet of the third chamber.

13. The device according to paragraph 7, wherein the second valve includes a third position wherein the lower outlet of the second chamber is closed and material, in response to centrifugal forces, accumulates in the lower outlet of the second chamber.

14. The device according to paragraph 7, wherein the second value is a metered valve.

15. The device according to paragraph 14, wherein the second value includes a metering groove.

16. The device according to paragraph 1 wherein the first chamber has a volume in a range from 10 nanoliters to 1 liter.

17. A device according to paragraph 1 wherein the first chamber has a volume in a range from 100 microliters to 10 milliliters.

18. The device according to paragraph 1 further comprising an actuator sleeve coupled to the first valve, the sleeve actuator, configured to surround the first channel and the first valve, comprising a first cam being adapted to contact the first valve and move the first valve from said first position to said second position when the sleeve actuator is rotated.

19. A device according to paragraph 18, wherein the actuator sleeve further comprises at least one stop tab configured to prevent over-rotation of the actuation sleeve.

20. A device according to paragraph 18, wherein the actuator further comprises a first stop tab, the first stop tap located opposite to the first cam.

21. A device according to paragraph 18, wherein the actuator sleeve is rotated about an axis transverse to the axis of the first channel.

22. A device according to paragraph 7 further comprising an actuator sleeve coupled to the first valve and the second valve, the sleeve actuator configured to surround the first channel, the first valve, the second channel and the second valve, the sleeve actuator comprising a first cam and a second cam, the first cam being adapted to contact the first valve and move the first valve from said first position to said second position when the sleeve actuator is rotated along a first path, and the second cam being adapted to contact the second valve and move the second valve from said first position to said second position when the sleeve actuator is rotated along a second path.

23. A device according to paragraph 7 wherein the first cam and second cam are orientated in opposite directions, the first cam being adapted to contact the first valve and move the first valve from said first position to said second position when the sleeve actuator is rotated in one direction, and the second cam being adapted to contact the second valve and move the second valve from said first position to said second position when the sleeve actuator is rotated in the opposite direction.

24. The device according to paragraph 23, wherein the actuator further comprises at least one internal stop tab configured to prevent over-rotation of the actuation device.

25. The device according to paragraph 124, wherein the actuator further comprises a first internal stop tab, the first stop tap located internally opposite to the first cam.

26. A device according to paragraph 22, wherein the actuator sleeve is rotated about an axis transverse to the axis of the first channel and the second channel.

27. The device according to paragraph 1 further comprising an actuator coupled to the first valve, the actuator including a piston and an inertial arm movable about a shaft in response to centrifugal forces applied to the device; the arm being adapted to apply a force on said piston causing the piston to displace in an axial direction and move the first valve from said first position to said second position.

28. The device according to paragraph 27 further comprising a spring applying a force on said inertial arm to maintain it in a first position and wherein said centrifugal forces apply a force on said inertial arm to move the inertial arm to a second position such that when the centrifugal force is removed, the inertial arm moves back to the first position and applies a force on the piston causing the piston to displace in an axial direction, contact the first valve, and move the first valve from said first position to said second position.

29. A device according to paragraph 7 further comprising an actuator coupled to the first valve and second valve, the actuator including a first piston, a second piston, a first inertial arm movable about a shaft in response to centrifugal forces applied to the device and a second inertial arm movable about a shaft in response to centrifugal forces applied to the device; the first arm being adapted to apply a force on said first piston causing the first piston to displace in an axial direction and move the first valve from said first position to said second position and the second arm being adapted to apply a force on said second piston causing the second piston to displace in an axial direction, contact the second valve, and move the second valve from said first position to said second position.

30. A device according to paragraph 29 wherein the actuator further includes an interlock, the interlock preventing the second piston from moving in an axial direction until the first piston has moved in an axial direction.

31. The device of any of paragraphs 1 to 30, wherein the fluid sample is a biological sample.

32. The device of any of paragraphs 1 to 31, wherein the fluid sample is a blood sample.

33. The device of any of paragraphs 1 to 32, wherein the first chamber comprises a lysis buffer.

34. The device of any of paragraphs 1 to 33, wherein the lysis buffer lyses blood cells.

35. The device of any of paragraphs 1 to 34, wherein any of the second or third chambers comprise a second or third fluid sample.

36. The device of any of paragraphs 1 to 18, wherein the first valve is operated manually.

37. The device of any of paragraphs 7 to 18, wherein the second valve is operated manually.

38. The device of any of paragraphs 1 to 37, wherein the centrifugation is performed in a fixed-angle, a swing-bucket, or purpose-built centrifuge.

39. The device of paragraph 38, wherein the purpose built centrifuge comprises a mechanism with at least one external arm to contact and apply force the first valve to move the first valve from a first position to a second position.

40. The device of paragraph 39, wherein the purpose built centrifuge further comprises a first mechanism to move a first external arm to contact and apply force the first valve to move the first valve from a first position to a second position, and a second mechanism to move a second external arm to contact and apply force to the second valve to move the second valve from a first position to a second position.

41. The device of paragraph 39 or 40, wherein the mechanism is an air cylinder.

42. A device for separation of particulates from a fluid sample by centrifugation, the device comprising:
a first chamber, the first chamber including an upper inlet for receiving a first fluid sample to be processed by device and a lower outlet for discharging material;
a first channel connecting the lower outlet of the first chamber to the upper inlet of a collection chamber;
a first valve disposed along the first channel wherein the valve forms a seal preventing material in the first chamber from flowing in to the collection chamber.

43. The device of paragraph 42, wherein a collection chamber is positioned adjacent to the device to receive material from the outlet of the first chamber.

44. The device of paragraph 42, wherein the collection chamber is a collection well for collecting the material, wherein the collection well receives the fluid sample from the upper inlet of the collection chamber.

45. The device according to paragraph 42, wherein the collection chamber is a slide.

46. The device according to paragraph 45, wherein the slide is a microscope slide.

47. The device according to any of paragraphs 42, 43, 44, 45 or 46, wherein the collection chamber can be removed from the device for analysis of the sample in the collection well of the collection chamber.

48. A method of separating particulates from a fluid sample, the method comprising
inserting a fluid sample into a first chamber of a multi-chamber separating device;
centrifuging the fluid sample in the first chamber causing the particulates to separate from the fluid sample and accumulate in the first chamber;
operating a valve to allow at least a portion of the accumulated particulates in the first chamber to flow into a second chamber; and
centrifuging the accumulated particulates in the second chamber to cause the particulates to further separate from the fluid sample and accumulate in the second chamber.

49. A method of separating particulates from a fluid sample, the method comprising:
providing a device comprising a first chamber connected to a second chamber by a first channel, the first channel including a first valve that can prevent material from flowing between the first chamber and the second chamber;
introducing a fluid sample containing particulates into the first chamber;
centrifuging the device for a predefined time, causing the particulates to separate from the fluid sample and accumulate near an outlet of the first chamber;
operating a first valve to enable the movement of the separated particulates from the first chamber to the second chamber;
centrifuging the device for a predefined time, causing the particulates to further separate from the fluid sample and accumulate at or near the bottom of a second chamber.

50. The method of paragraph 49, wherein the second channel in the device comprises a lower outlet, and the device further comprises a third chamber connected to the outlet of the second chamber by a second channel, the second channel including a second valve that can prevent material from flowing between the second chamber and the third chamber; the method further comprising;
operating a second valve to enable the movement of the separated particulates from the second chamber to the third chamber;
centrifuging the device for a predefined time, causing the particulates to further separate from the fluid sample and accumulate at or near the bottom third chamber.

51. The method of any of paragraphs 48 to 51, wherein the fluid sample is a biological sample.

52. The method of any of paragraphs 48 to 51, wherein the fluid sample is a blood sample.

53. The method of any of paragraphs 48 to 52, wherein the first chamber comprises a lysis buffer.

54. The method of any of paragraphs 48 to 53, wherein the lysis buffer lyses blood cells.

55. The method of any of paragraphs 48 to 54, wherein any of the second or third chambers comprise a second or third fluid sample.

56. The method of any of paragraphs 48 to 55, wherein the first valve is operated manually.
57. The method of any of paragraphs 49 to 55, wherein the second valve is operated manually.
58. The method of any of paragraphs 49 to 57, wherein the centrifuging is performed in a fixed-angle, a swing-bucket, or purpose-built centrifuge.
59. The method of any of paragraphs 49 to 58, wherein, in operation, the valve moves from a first position to a second position.
60. The method of any of paragraphs 49 to 59, wherein the operation of valves to move from a first position to a second position comprises providing an actuation mechanism adapted to engage the valve and operate the valve.
61. A system of separation and concentration of particulates from a fluid sample by centrifugation comprising:
   (i) a device comprising
   a first chamber, the first chamber including an upper inlet for receiving a first fluid sample to be processed by device and a lower outlet for discharging material;
   a second chamber, the second chamber having an upper inlet;
   a first channel connecting the lower outlet of the first chamber to the upper inlet of the second chamber; and
   a first valve disposed along the first channel wherein the valve forms a seal preventing material in the first chamber from flowing in to the second chamber.
   (ii) a centrifuge.
62. The system of paragraph 61, wherein the second chamber comprises a lower outlet, and the device further comprises a third chamber, the third chamber including an upper inlet for receiving a fluid sample to be processed by the device and a lower outlet for discharging material;
   a second channel connecting the lower outlet of the second chamber to the upper inlet of the third chamber; and
   a second valve disposed along the second channel wherein the second valve forms a seal preventing material in the second chamber from flowing in to the third chamber.
63. The system of paragraph 61, wherein the centrifuge is a fixed-angle, a swing-bucket, or purpose-built centrifuge.
64. The system of paragraph 63, wherein the purpose-built centrifuge comprises a mechanism with at least one external arm to contact and apply force the first valve to move the first valve from a first position to a second position.
65. The system of paragraph 63, wherein the purpose built centrifuge further comprises a first mechanism to move a first external arm to contact and apply force the first valve to move the first valve from a first position to a second position, and a second mechanism to move a second external arm to contact and apply force to the second valve to move the second valve from a first position to a second position.
66. The system according to paragraph 61 or 62, wherein the second or third chamber is a collection well for collecting the material, where the collection well receives the fluid sample from the inlet of the second or third chamber.
67. The system according to paragraph 61 or 62, wherein the second or third chamber is a slide.
68. The system according to paragraph 67, wherein the slide is a microscope slide.
69. The system according to any of paragraphs 61 to 68, wherein the second or third chamber comprising a collection well can be removed from the device for analysis of the sample in the second or third chamber.

This invention is further illustrated by the following example which should not be construed as limiting. The contents of all references cited throughout this application, as well as the figures incorporated herein by reference.

EXAMPLE

Methods

Prototype Separator/Concentrator Device Design

Design work on a prototype was performed in Pro/Engineer Wildfire 3.0 modeling software and at Fraunhofer CMI. The primary design goal was the metered valve that transfers 5 µL when actuated. Two prototypes were designed and constructed. The first had two chambers and a single valve. This first prototype was primarily used to demonstrate the reproducibility of the metering valve. The second valve featured there chambers and allowed for the incorporation of a single wash step in the middle chamber. Major design goals for the final prototype were (1) the sectioning of the prototype into three machineable pieces, (2) alignment of valves and O-rings, and (3) weight reduction. The final design is shown in FIG. 13.

Valve Actuator Design Through Static Force Analysis

Figure 12B:
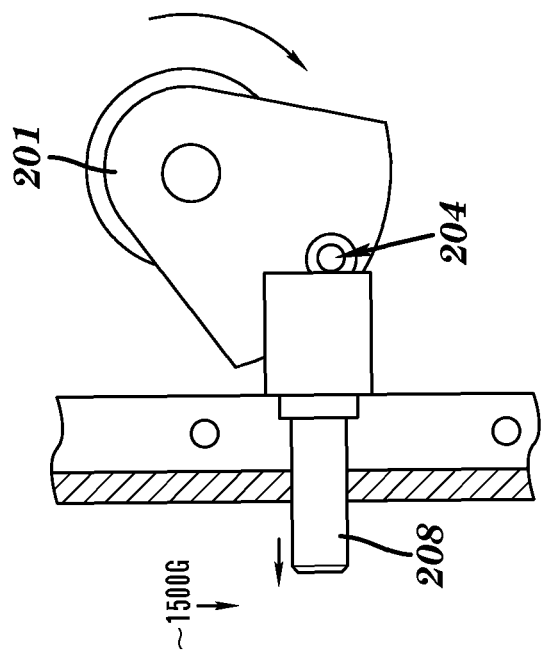
FIGS. 12A-12B are perspective views of one embodiment of an inertial actuator.
Figure 12A:
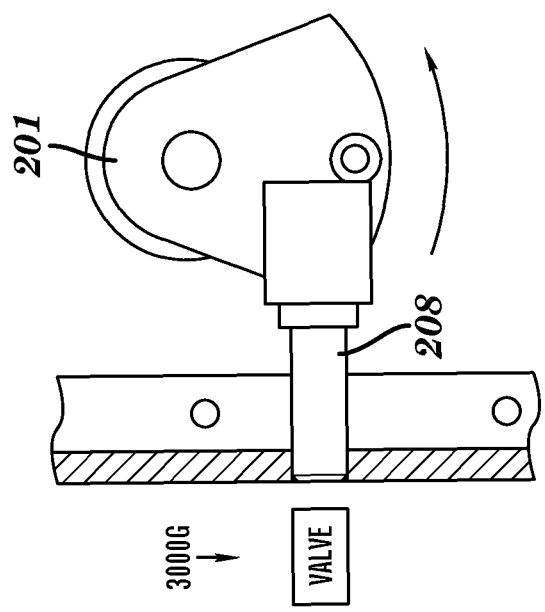

The first prototype and the stand alone second prototype (left half of FIG. 13) required manual actuation of the valves. In order to fully automate the sample preparation process, an actuation device was needed to actuate the valves. A valve actuator (right half of FIG. 13, FIG. 12) was designed to take advantage of the nature of centrifugation and used the changes in the applied gravitational force to drive the mechanism. The arm is in its top position (not shown) when there is no gravitational force applied. During the accelerating phase of centrifugation, the gravitation force increases and the arm descends downward with the ball bearing sliding to its "inside" position so that the arm can slide over the bolt without moving it. The arm slides to its lowest position (FIG. 12A) at the maximum applied gravitational force of 3,000 G. At this point the ball bearing (latch) slides to its "outside" position. As the centrifuge decelerates, the gravitational force decreases and allows the arm to lift up with the ball bearings supporting the bolt. As the result, the bolt is pushed forward into the prototype, moving the valve from one chamber to the next (FIG. 12B).

The linear equations for mechanical static force analysis of an actuator for a 5 µL valve are shown below. Considerations incorporated into the equations are appropriate torsion springs and device materials based on friction coefficients and spring constants. The optimum mass of the materials to be used for the bolt and the arm of the valve actuator were determined from the force equations. These equations modeled the mechanical system of the valve and, by determining the required valve force, determined the necessary torque that must be generated to actuate the valve.

Two critical cases of valve actuation were considered and the free body diagrams of each case are shown in FIG. 31A-31B and examined. The two critical cases are accelerating and deceleration motion (shown in FIGS. 31A and 31B respectively). Diagrams with corresponding static force analysis are also shown in FIGS. 31A and 31B. Increasing gravitation force slides the arm from its top, relaxed position to its low position. A spring-loaded bearing is designed to be compressed as the arm slides downwards but extends during the deceleration phase, pushing the valve forwards and thereby actuating the valve. The valve force was determined by screwing an eye hook into the valve and using a spring scale to measure the force required to move the valve. This force was approximately 5 lbs and was considered in the analysis.

The forces considered are gravitational force, weight, torsional spring force, and friction.

Prototype Testing

Single-Valve Prototype

Prototypes were designed and constructed for the purpose of testing the automation of the separation procedure. The original prototype, shown in FIG. 1, had only a single valve separating two chambers and was primarily used to test the valve design and assess the efficacy of bacteria transfer.

Reproducibility of Metered Valve Transfer Volume

The valve design, shown in FIG. 5, was initially designed to transfer 5 µL. In FIG. 5, the three wide grooves are occupied by O-rings and the thin groove is aligned with the output of the top chamber. A 10 mL sample is initially loaded in the top chamber. After centrifugation, actuation of the valve slides the thin groove until it is aligned with the inlet to the bottom chamber. A series of over 60 data points measuring the volume of liquid transferred by the valve was collected by comparing the weight of the collection cup before and after valve actuation. The bottom chamber was tared before the each trial so that the observed weight was due to the transferred volume. The change in weight was converted to volume assuming a density of 1.00 g/cm$^3$ for water.

Bacteria Recovery: General Procedure

After satisfactorily demonstrating the reproducibility of the valve, the single-valve prototype was utilized extensively to study bacteria recovery in the bottom chamber in a variety of experimental conditions. The first step in the general procedure was a thorough wash of the device, valve, and collection cup using 70% ethanol. For trials involving the use of whole blood, the prototype was also washed in 10% bleach. After thorough drying using Kimwipes and Q-tips to prevent scratching, three o-rings were installed on the valve. The valve was then inserted until the groove is visible through the outlet port of the top chamber. After being tared on an analytical balance, the bottom chamber was screwed into the bottom of the device. The main (top) chamber was then filled with 10 mL of the solution to be tested. The device was then centrifuged at 3000 rcf. The valve was then actuated by pushing the valve in until it was flush with the device surface. Valve actuation was followed by a second centrifugation step. The collected sample in the collection cup was then weighed to determine the volume transferred. Finally, the entire output was plated onto LB agar and incubated overnight at 37° C. and the number of colonies was counted the next day.

Each experimental condition was performed in duplicate or triplicate. The positive control for each experiment was the appropriate bacterial stock. In addition, a wash step with 10 mL of water was performed between each trial using bacteria to serve as a negative control. The percent recovery for each condition was calculated by comparing the actual recovery with the expected recovery, as indicated by the positive control.

Bacteria Recovery: Centrifugation Time

The first experiments sought to characterize the effect of varying centrifugation time on the bacteria recover. Ten mL of sterile water was spiked to a concentration of 1E3 cfu/mL with *E. coli* (1E4 total cfu in 10 mL) and was tested with 2 minute, 5 minute, and 10 minute centrifugation times for both centrifuge steps (before and after valve actuation).

Bacteria Recovery: 1E3 cfu/mL *E. coli* in Water, Serum, and Blood with Lysis Solution After determining that length of centrifugation has minimal impact on the percent recovery of bacteria, the recovery of bacteria from different solutions was studied. In this set of experiments, the solution spiked with *E. coli* was varied. The bacteria recovery experiment was performed using 10 mL of sterile water, 5 mL of sterile water with 5 mL of blood serum, and 5 mL of whole blood with 5 mL of the 0.8% Na$_2$CO$_3$/0.05% TRITON X-100 lysis solution. Centrifugation at 3,000 rcf for five minutes was selected for all trials.

The serum experiments were performed with the aim of reducing the loss of bacteria to the side walls. Moreover, serum mimics whole blood without requiring the use of the lysis solution to eliminate red blood cells.

Bacteria Recovery: Pluronic Treatment

Unsatisfactory recovery rates from the above experiments motivated the search for a method to prevent bacteria from clinging to the sidewalls and being lost during the centrifugation process. The solution found to address this problem was to pre-treat the prototype with 15 minutes of sonication in a 0.5 g/L solution of pluronic. Pluronic, a hydrophilic polymer of polyethylene oxide, has been reported to block the adhesion of bacteria to synthetic materials such as silicone rubber and other plastics. Pluronic is also commonly used in biological applications involving cell culturing media because it lowers the stress required to shear cells from sidewall attachments. It was expected that treatment of the prototype in pluronic will improve bacteria recovery.

The pluronic protocol incorporated 10 minutes of sonication followed by 5 minutes of soaking in a 0.5 g/L solution of pluronic between washing of the prototype and the loading of the bacteria sample. The above experiments of 1E3 cfu/mL of *E. coli* in water, water with blood serum, and blood with lysis solution were repeated using the pluronic treatment.

Based on much improved recovery results, particularly for the water and serum condition, a second series of experiments with blood and lysis solution was performed. The ratio of blood to lysis solution was varied with hopes of improving bacteria recover by reducing the shock introduced by a high concentration of lysis solution. The tested ratios of blood to lysis solution were 1:1, 2:1, 3:1, 4:1, 5:1, 9:1, and 10:1.

A centrifugation time of 5 minutes at 3,000 rcf was also used for all trials.

Bacteria Recovery: 1E2 cfu/mL *E. coli*

Improved bacteria recovery results for 1E3 cfu/mL of bacteria motivated the study of bacteria recovery when starting 1E2 cfu/mL of *E. coli*. These experiments attempted to establish that the prototype can effectively recover bacteria from even lower concentrations.

The experiments with water, water with serum, and blood with lysis solution (1:1) were repeated using a concentration of 1E2 cfu/mL (1E3 cfu total in 10 mL) of *E. coli*. As before, samples were centrifuged for 5 minutes at 3,000 rcf both before and after valve actuation.

Double-Valve Prototype Testing

Reproducibility of Output Volume

Following the design and manufacture of the new prototype, it was tested for output volume reproducibility in a manner similar to the single-valve prototype. The one additional feature of this prototype is the presence of a third chamber so that a wash step can be implemented into the procedure. The final design is shown in FIG. 12 for reference. A sample was loaded into the top chamber. Following five minutes of centrifugation at 3,000 rcf, the top valve was actuated and a small volume was transferred to the middle chamber during a second centrifugation cycle. The bottom valve was then actuated and a small volume was transferred to the bottom chamber with a third centrifugation cycle. The volume of sample collected in the bottom chamber was quantified by using a micropipetting to withdraw 5 µL at a time. This experiment was repeated over 10 trials in order to characterize the reproducibility of volume outputted by the device.

Bacteria Recovery from 1E2 cfu/mL E. coli

Similar to the bacteria recovery experiments for the original prototype, experiments were performed to assess the recovery of viable bacteria from the device. Based on experiments with the single-valve prototype that demonstrated reasonable recovery using 1E2 cfu/mL E. coli, the same concentration was chosen for experiments with the new prototype. The operation of the double-valve prototype was very similar to the single-valve prototype with a few minor changes. First, the middle chamber is initially filled with 0.5 mL of sterile water so that a wash step occurs when the bacteria is transferred through the middle chamber. Second, there is a second valve actuation step and a third centrifugation step so that the sample is transferred all the way to the bottom chamber. For each of these trials, the same pluronic treatment was applied to the prototype because the treatment was proven to improve bacteria recovery during the single-valve prototype testing.

Bacteria recovery from a water-blood serum mixture and from a 1:1 blood-lysis solution mixture was measured with at least three trials each. The water-blood serum mixture is 5 mL water with 5 mL blood serum and the blood-lysis solution mixture is 1 mL blood with 5 mL of the 0.8% $Na_2CO_3$/0.05% TRITON X-100 solution. Recovery was assessed by plating the entire output on LB and counting the number of bacteria colonies the next day after overnight incubation at 37° C.

Demonstration of Device Output Compatibility with SERS

A final proof-of-concept experiment was to verify that the bacteria output from the prototypes yields a meaningful spectrum when imaged using SERS. The bacteria tested were grown from a culture. On the day of the experiment, an overnight culture is used to start a six-hour culture. After six hours, 2 mL of bacteria is extracted and washed five times by centrifuging, decanting the supernatant, and resuspending in 2 mL of MILLIPORE™ water. After washing, the bacteria sample was divided into two 1 mL aliquots. One aliquot was used as a control to generate the reference spectrum. The other aliquot was mixed with 9 mL of water and processed in the pluronic-treated single-valve prototype. The collected output was resuspended in 1 mL of water and used to generate SERS spectra.

Results

Prototype Design

Figure 7B:
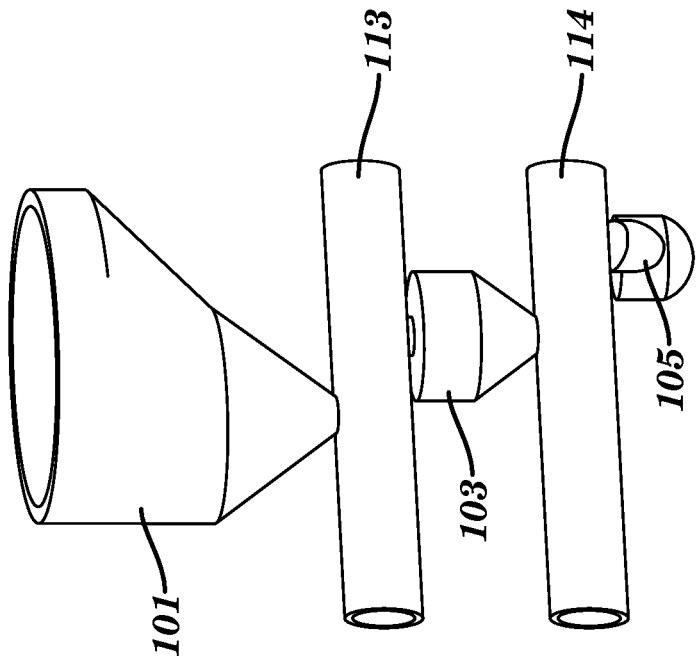
FIGS. 7A-7B show a design of one embodiment of a separator/concentrator device.
Figure 7A:
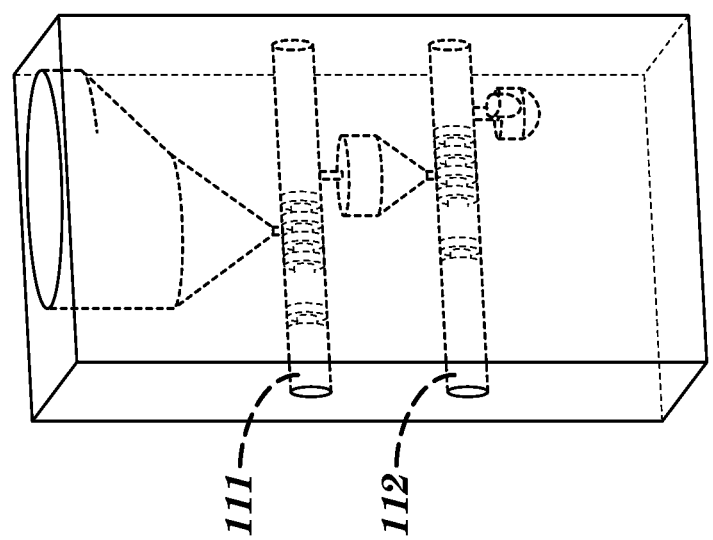

The general elements of the prototype design are shown in FIG. 7. The top chamber is designed to accept 11 mL of liquid, where 10 mL of blood will be mixed with 1 mL of lysis solution. Various ratios of blood and lysis solution can be used, such as 1:1 and 2:1 and 9:1, which were found to give the highest bacteria recovery and blood cell lysis. A volume (e.g. 1 mL) of lysis solution is placed in this chamber. Then blood is added into this chamber, mixed and centrifuged. The first valve, activated by a fixed valve actuator system discussed in a later section, passes a small volume of blood (approximately 15 µL) containing the bacterial pellet to the middle chamber where it is washed with MILLIPORE™ filtered water. The middle chamber is pre-loaded with a volume of water (e.g. 100 µL). This centrifugation process is repeated a second time until a final volume of 100 µL is obtained in the bottom chamber. The round protrusion from the side of the bottom chamber will house a membrane-covered opening through which the final product can be extracted for SERS.

Design Refinements

The initial design shown in FIG. 13 is exemplary and can be readily adapted to other configurations as needed depending on the fluid needing separation and the particulate matter to be isolated and concentrated. The embodiment in FIG. 13 was refined in two ways. First, the positioning of the chambers was adjusted so that the output axis of one chamber is exactly 0.400 inches from the input axis of the next chamber along the axis of the connecting valve (FIGS. 6 and 7, the valve connecting the top and middle chambers is shown). Accordingly, the valve (see FIGS. 5 and 6) was redesigned to accommodate the 0.400 inch distance between the chambers. The valve design shown holds 5 µL but the width of the valve (centered below the output of the top chamber in FIG. 7) is adjustable to accommodate up to 100 µL of fluid. Other sized volumes can readily be adjusted. A closer inspection of FIG. 7 reveals that the distance from the chamber output to the left face of the device is different for the two valves. To make both valves compatible with the same valve actuating device, a second copy of the valve was created with a longer arm so that it sits flush with the left face when it is aligned to receive the output of the middle chamber.

The second refinement is illustrated in FIG. 6A. The black dashed line indicates the original revolved surface with a sloped entrance into the chamber. Preliminary experiments with this design indicated a possibility of bacterial loss suggesting that the pellet fails to drop vertically into the chamber and instead clings to the sloped wall. Thus, both the middle and bottom chambers were redesigned to have a flat entrance so that a bacteria pellet will drop directly into the bottom of the chamber.

Sectioning Into a Machineable Three-Piece Prototype

Injection molding is one possible method of producing a one-piece disposable separation device. However manufacturing of such molds is expensive and inappropriate for prototype production. To avoid this problem, two cuts were created through the design to create three machineable pieces that will be fastened together with four long bolts at each corner. This allowed for in-house production of prototypes for testing. The cuts were chosen to be through the middle and bottom chambers so the chambers can be machined directly. The schematic diagram of the three pieces is shown below in FIG. 8. To assemble the three pieces together, four holes have been added to make room for fasteners. The bottom piece contains a counter-bored thru-hole, the middle piece is a thru-hole, and the top piece is threaded (FIG. 9).

The final design of the swinging bucket insert retained the major elements of the previous design: three chambers cut into three machineable pieces that are held together by four bolts. The major changes in the design were focused on weight reduction. The top section had a lot of volume cut away from each corner, concurrently reducing the weight of the device and allowing for the use of shorter bolts. In addition, a large horizontal hole was added to the design for further weight reduction. A final modification was the addition of a lid for the top chamber in order to prevent accidental spills. FIGS. 3 and 9 show the final assembled three-piece device.

Valve Actuator Design Through Static Force Analysis

The equations derived for the static force analysis of the valve actuator (see methods section) were plotted in Microsoft Excel to determine the range of values possible for the torsion spring constant. Material values for weight, coefficient of friction, and spring constants were inserted into the above equations. These were later varied to optimize the process of actuation as needed. The torsion spring constant was the critical factor in actuating the valve and the torsion spring constant versus angle was plotted below in FIG. 18. Design work in ProEngineer revealed that the arm must descend to an angle of at 6° or lower from the vertical axis in order for the ball bearing to clear the bolt and trigger actuation. The arm must then ascend to at least 60° and the torsion force must be at least equal to the valve force in order to trigger actuation.

Figure 18B:
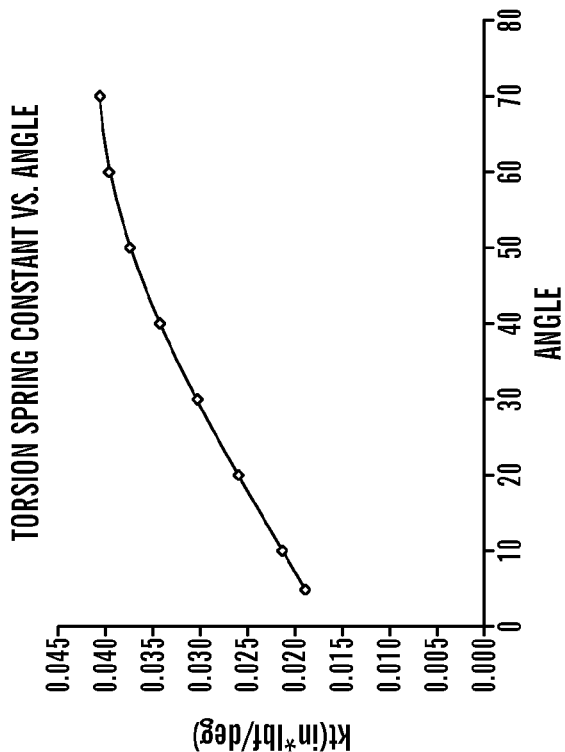
FIGS. 18A-18B show a graph of torsion spring constant as a function of angle during acceleration and deceleration.
Figure 18A:
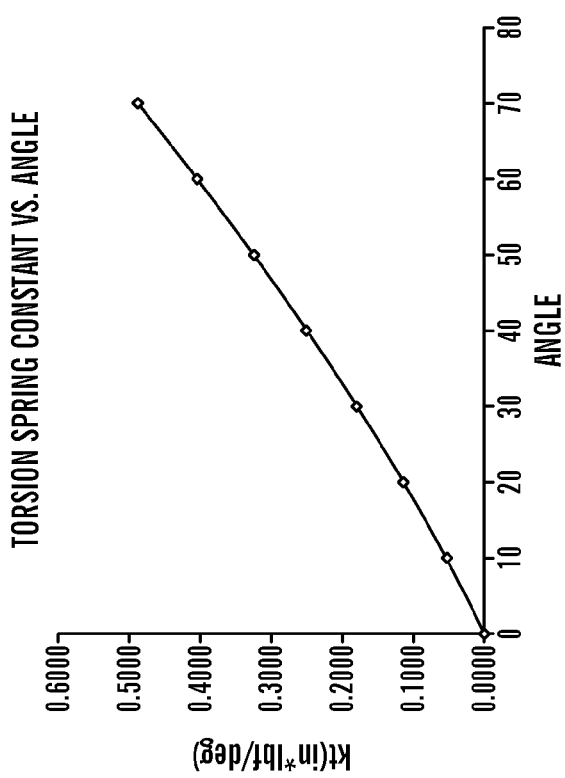

The minimum value of the torsion spring constant kt, 0.0318 in-lbf/deg was determined from the plot of the accelerating case shown above in FIG. 18A. This value of the torsion spring constant is necessary to provide the required torque of 4.89 in-lbf. The maximum kt, 0.0407 in-lbf/deg is determined from the plot of the decelerating case (FIG. 18B). This provides a torque of 3.97 in-lbf. A torsion spring was chosen with a spring constant in the range of 0.0318-0.0407 in-lbf/deg.

Reproducibility of Metered Valve Transfer Volume for a Single Valve Prototype

Figure 19:
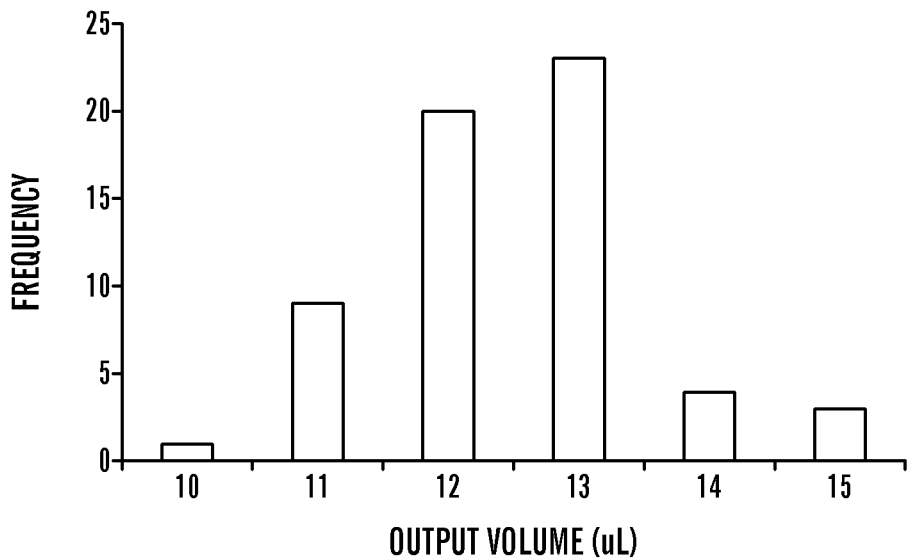
FIG. 19 is a histogram showing the reproducibility of the metered volume from a single valve prototype. The volume metered by the 5 µL valve from 60 trials presented in histogram form. The average final volume was 13.04 µL.

Over 60 trials are shown and the volume transferred is consistently around 13 µL (FIG. 19). This was unexpected as the groove on the valve was designed for only 5 µL. As it turns out, the additional space in the O-ring grooves contribute to the transferred volume and is responsible for the additional 8 µL (See FIG. 5). This lesson was applied to the design of valves for the double-valve prototype so that the valves were groove-less and relied on the O-ring transfer of fluid to achieve a 5 µL volume transfer.

Bacteria Recovery: Centrifugation Time

Figure 20:
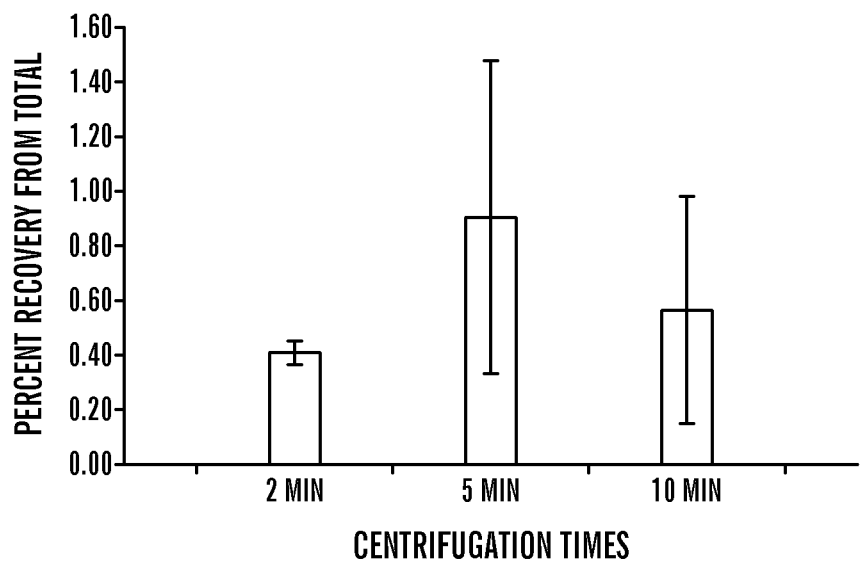
FIG. 20 is a histogram showing the bacteria colony count for 1E3 cfu/mL in water as a function of centrifugation time. The expected recovery is ~10,000 colonies, so overall recovery in this embodiment is below 1%, but can be optimized by one of ordinary skill in the art to much greater recoveries. Error bars of one standard deviation are shown.

The data shown in FIG. 20 demonstrates the effect of centrifugation time on bacteria recovery. Although the five minute condition showed the highest recovery of the three, overall recovery rates for bacteria in water was low (below 1%). This experiment indicated that centrifugation for five minutes is sufficient but there are other factors causing significant bacteria loss. To test whether bacteria was being lost to the side-walls of the prototype, subsequent experiments using the pluronic treatment was performed.

This result shows that centrifugation time is not a significant factor in the recovery of bacteria. Therefore, centrifugation time can be varied to accommodate other time constraints such as lysis time as the need arises. As a standard condition, however, centrifugation for five minutes was chosen for all subsequent experiments.

Figure 21:
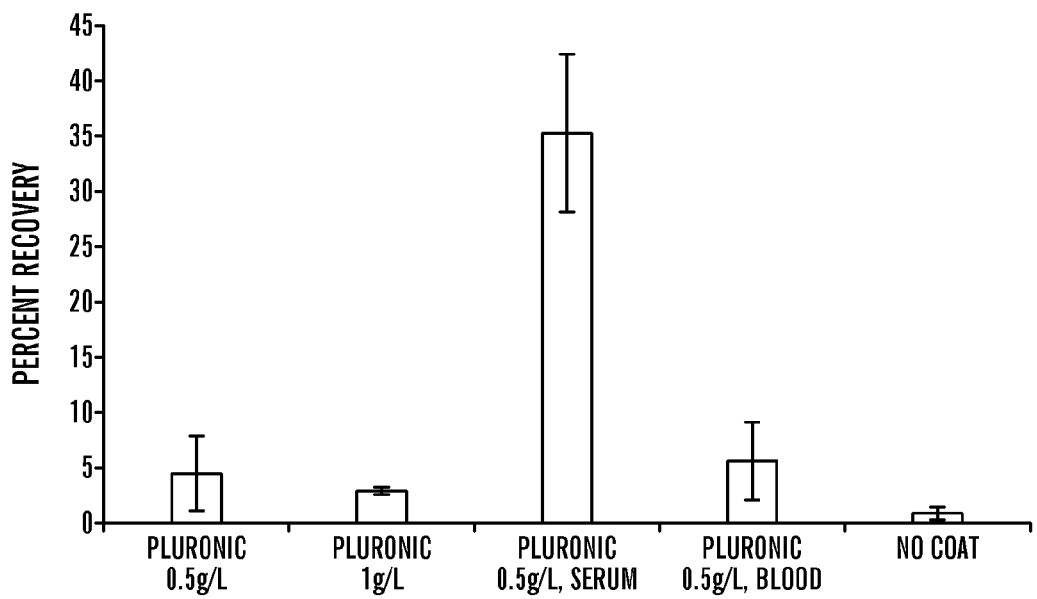
FIG. 21 is a histogram showing the percent of bacteria recover for the Pluronic coated and non coated device. Error bars of one standard deviation are shown.

Bacteria Recovery: Pluronic Treatment with Water, Water with Serum, and Blood with Lysis Solution FIG. 21 shows that sonication with both 0.5 g/L and 1 g/L of pluronic solution yielded very similar results. Recovery from water with the pluronic treatment was approximately tenfold higher than recovery from water without pluronic. The significant improvement in recovery was observed when the pluronic treatment is coupled with the serum condition. Ten to twenty-fold improvements in recovery was observed for both the water with serum and blood with lysis solution conditions compared to similar experiments without the pluronic treatment.

Based on these results, treatment with 0.5 g/L of pluronic was chosen for the following experiments.

Bacteria Recovery: 1E2 cfu/mL *E. coli*

Figure 22:
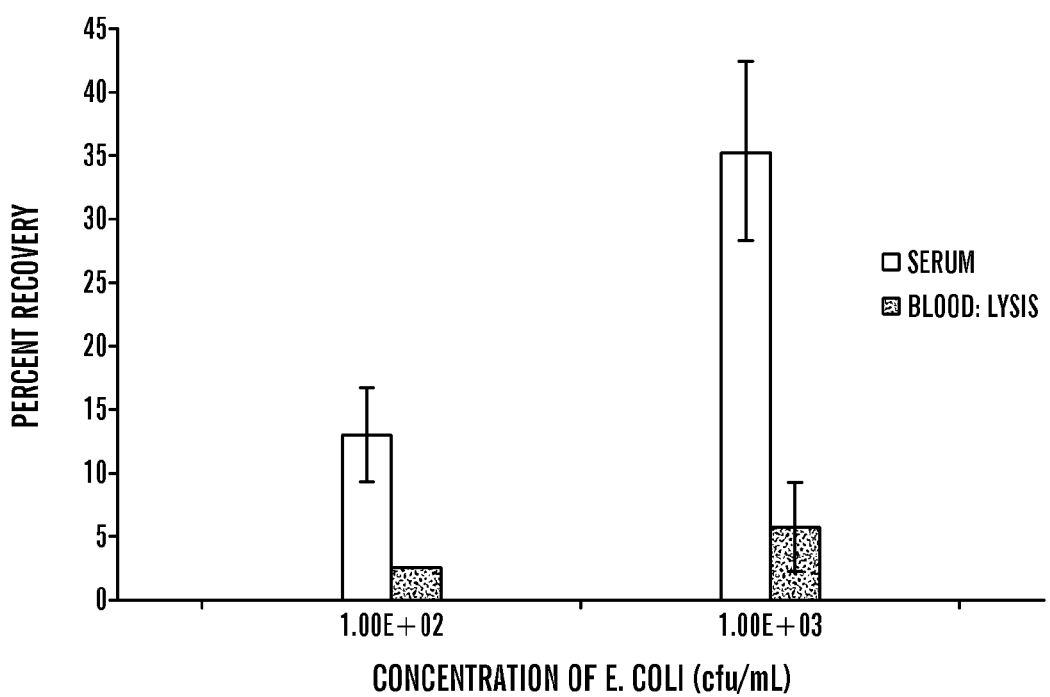
FIG. 22 is a histogram showing the bacteria yield from a concentration of 1E2 cfu/mL and 1E3 cfu/mL E. coli from samples of serum and samples of blood and lysis solution in a 1:1 ratio. Error bars of one standard deviation are shown.

FIG. 22 shows the result of reducing *E. coli* concentration from 1E3 cfu/mL to 1E2 cfu/mL using the single-valve prototype. Percent recovery for both the serum and blood with lysis conditions showed an approximate twofold decrease. This result was surprising as similar results for percent recovery were expected from both conditions. Nevertheless, reasonable total bacteria recovery was obtained using 1E2 cfu/mL and this experiment demonstrated the capacity of the single-valve prototype to transfer a small number of bacteria.

Reproducibility of Metered Valve Transfer Volume for a Double-Valve Prototype

Figure 23:
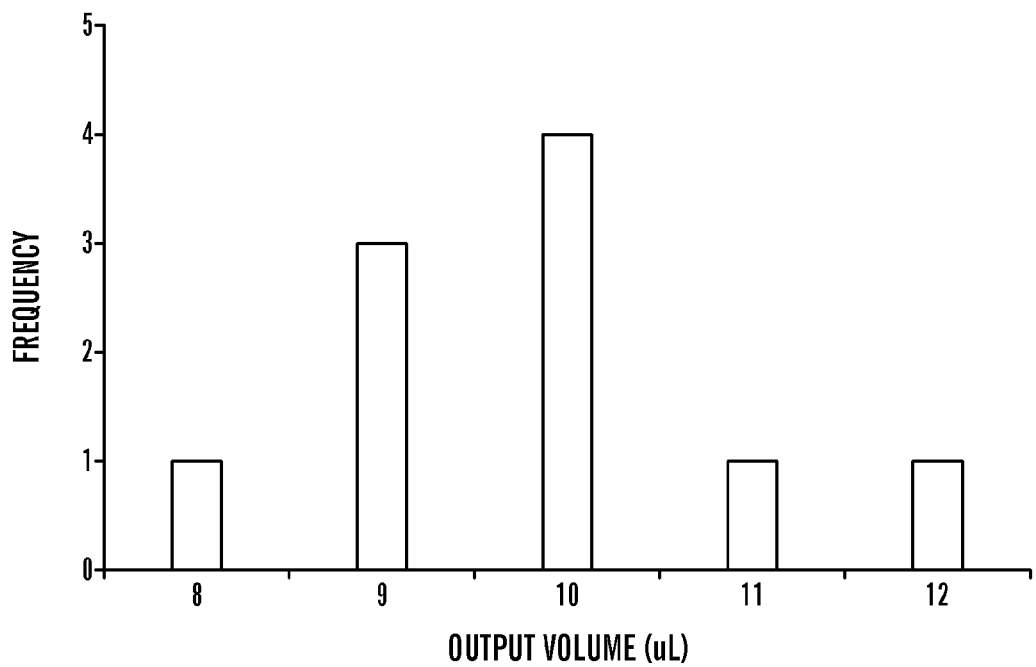
FIG. 23 is a histogram of metered volume reproducibility. The volume metered by the double valve prototype from 10 trials is presented in histogram form. The average output volume is 9.8 µL demonstrating that the volume of material transferred from one chamber to another when the valve is operated from position 1 to position 2 is has a reliable consistent volume.

FIG. 23 shows the histogram of the distribution of output volumes for the double valve prototype. Similar to the reproducibility experiment for the single-valve prototype, the output volume was found to consistently fall within a narrow range. However, once again, the obtained volume was greater than expected. The groove-less valves transferred an average 10 µL. This result indicated that further refinement with the O-ring grooves must be made to be able to more precisely control the volume transferred by the valve.

Bacteria Recovery from 1E2 cfu/mL *E. coli*

Figure 24:
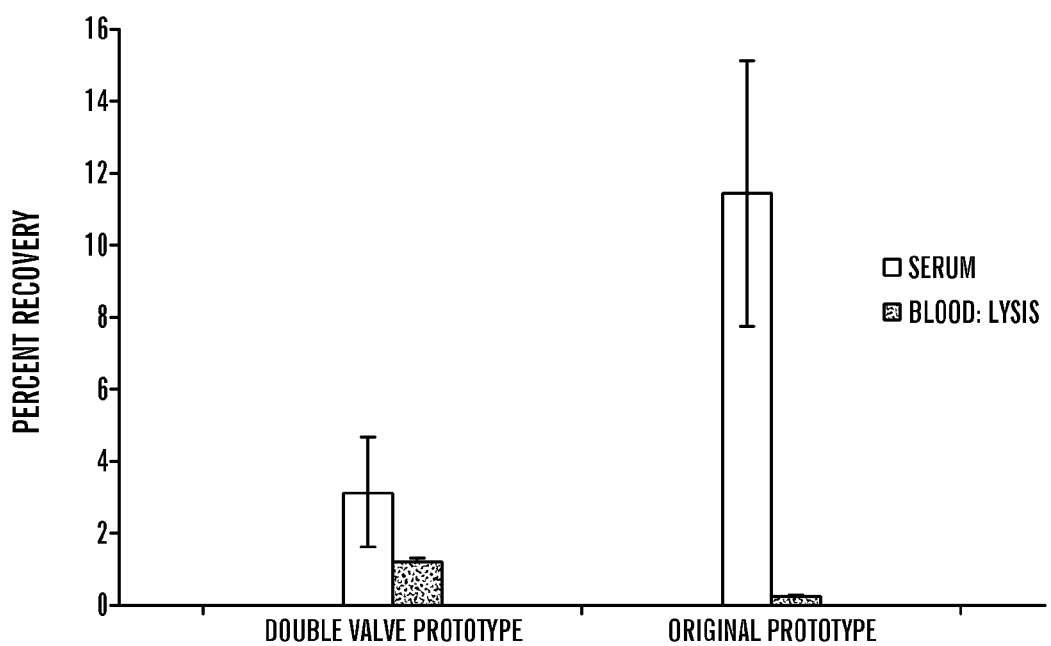
FIG. 24 is a histogram showing the reproducibility of the metered volume from a double valve prototype and from the 5 µl, valve prototype from samples of 1E2 cfu/mL infected serum and equal parts blood and lysis solutions. Error bars of one standard deviation are shown

The percent recovery of 1E2 cfu/mL *E. coli* using the double-valve prototype compared to the same experiments performed using the single-valve (original) prototype is shown in FIG. 24. The data shown is the recovery from the prototypes with the pluronic treatment. Compared to the bacteria recovery from the original prototype, the percent recoveries obtained from the double-valve prototype were approximately fourfold lower for the serum condition but slightly increased for the blood with lysis condition. This improved recovery may be attributed to the wash step added in the double-valve prototype.

Demonstration of Device Output Compatibility with SERS

Figure 25:
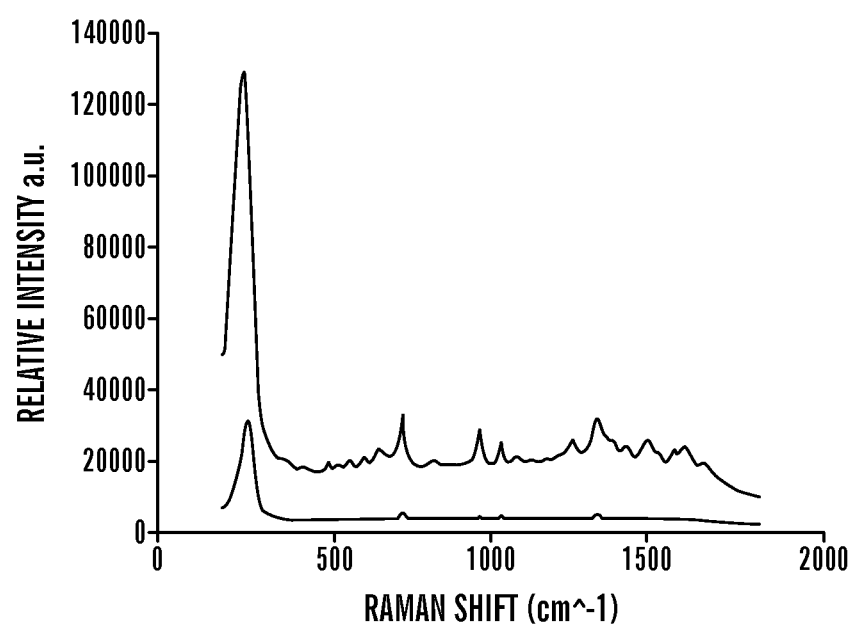

FIG. 25 shows the SERS spectrum of bacteria processed using the single-valve prototype (bottom trace) compared to a control spectrum (upper trace) of the same bacteria. The key identifying peaks for *E. coli* are visible at approximately 300 $cm^{-1}$ and 725 $cm^{-1}$ but at a much lower amplitude. This result indicates that the processed bacteria are capable of yielding a viable signal.

What is claimed:

1. A device for separation of particulates from a fluid sample by centrifugation, the device comprising:
    a first chamber, the first chamber having an upper inlet for receiving the fluid sample to be processed by the device and a lower outlet for discharging material;
    a second chamber, the second chamber having an upper inlet for receiving a sample material from a first collection reservoir in a first valve, and a lower outlet for discharging material;
    a first channel connecting the lower outlet of the first chamber to the upper inlet of the second chamber;
    the first valve disposed along the first channel, wherein the first valve forms a seal preventing material in the first chamber from flowing in to the second chamber and wherein the first valve comprises the first collection reservoir for collecting particulates from the first chamber;
    a third chamber, the third chamber having an upper inlet for receiving a sample material from a second collection reservoir in a second valve;
    a second channel connecting the lower outlet of the second chamber to the upper inlet of the third chamber; and
    the second valve disposed along the second channel wherein the second valve forms a seal preventing material in the second chamber from flowing into the third chamber and wherein the second valve comprises the second collection reservoir for collecting particulates from the second chamber.

2. The device according to claim 1, wherein the third chamber is a collection well for collecting the sample material from the second collection reservoir.

3. The device according to claim 1, wherein the third chamber is an indentation located in the surface of a slide or a microscope slide.

4. The device according to claim 1, wherein the third chamber can be removed from the device for analysis of the sample material in the third chamber.

5. The device according to claim 1, wherein the first valve can be operated to move between a first position and a second position in the first channel, and the second valve can be operated to move between a first position and a second position in the second channel, wherein when the first valve is at the first position, the first collection reservoir is open to the first chamber and can receive the material discharged from the lower outlet of the first chamber, and when the first valve is at the second position, the first collection reservoir is open to the upper inlet of the second chamber and can deposit the material into the upper inlet of the second chamber; and wherein when the second valve is at the first position, the second collection reservoir is open to the second chamber and can receive the material discharged from the lower outlet of the second chamber, and when the second valve is at the second position, the second collection reservoir is open to the upper inlet of the third chamber and can deposit the material into the upper inlet of the third chamber.

6. The device according to claim 1, wherein at least the first valve can be operated to move to a third position in the first channel or the second valve can be operated to move to a third position in the second channel, wherein when the first valve is in the third position in the first channel, the first valve collection reservoir is not open to the outlet of the first chamber and the lower outlet of the first chamber is closed, and in response to centrifugal forces, material accumulates in the lower outlet of the first chamber, and wherein when the second valve is in the third position in the second channel, the second valve collection reservoir is not open to the outlet of the second chamber and the lower outlet of the second chamber is closed, and in response to centrifugal forces, material accumulates in the lower outlet of the second chamber.

7. The device according to claim 1, wherein at least one of the first valve or the second valve is a metered valve.

8. The device according to claim 1, further comprising an actuator sleeve coupled to the first valve, the sleeve actuator, configured to surround the first channel and the first valve, comprising a first cam being adapted to contact the first valve and move the first valve from said first position to said second position when the sleeve actuator is rotated.

9. The device according to claim 5, further comprising an actuator sleeve coupled to the first valve and the second valve, the sleeve actuator configured to surround the first channel, the first valve, the second channel and the second valve, the sleeve actuator comprising a first cam and a second cam, the first cam being adapted to contact the first valve and move the first valve from said first position to said second position when the sleeve actuator is rotated along a first path, and the second cam being adapted to contact the second valve and move the second valve from said first position to said second position when the sleeve actuator is rotated along a second path.

10. A device according to claim 9 wherein the first cam and second cam are orientated in opposite directions, the first cam being adapted to contact the first valve and move the first valve from said first position to said second position when the sleeve actuator is rotated in one direction, and the second cam being adapted to contact the second valve and move the second valve from said first position to said second position when the sleeve actuator is rotated in the opposite direction.

11. The device according to claim 10, wherein the actuator further comprises at least one internal stop tab configured to prevent over-rotation of the actuation device.

12. The device according to claim 5, further comprising an actuator coupled to the first valve, the actuator including a piston and an inertial arm movable about a shaft in response to centrifugal forces applied to the device; the arm being adapted to apply a force on said piston causing the piston to displace in an axial direction and move the first valve from said first position to said second position in the first channel.

13. The device according to claim 12 further comprising a spring applying a force on said inertial arm to maintain it in a first position and wherein said centrifugal forces apply a force on said inertial arm to move the inertial arm to a second position such that when the centrifugal force is removed, the inertial arm moves back to the first position and applies a force on the piston causing the piston to displace in an axial direction, contact the first valve, and move the first valve from said first position to said second position.

14. A device according to claim 5 further comprising an actuator coupled to the first valve and second valve, the actuator including a first piston, a second piston, a first inertial arm movable about a shaft in response to centrifugal forces applied to the device and a second inertial arm movable about a shaft in response to centrifugal forces applied to the device; the first arm being adapted to apply a force on said first piston causing the first piston to displace in an axial direction and move the first valve from said first position to said second position and the second arm being adapted to apply a force on said second piston causing the second piston to displace in an axial direction, contact the second valve and move the second valve from said first position to said second position.

15. A device according to claim 14 wherein the actuator further includes an interlock, the interlock preventing the second piston from moving in an axial direction until the first piston has moved in an axial direction.

16. The device of claim 1, wherein the first valve or second valve is operated manually.

17. The device of claim 5, wherein the centrifugation is performed in a fixed-angle, a swing-bucket, or purpose-built centrifuge.

18. The device of claim 17, wherein the purpose built centrifuge comprises a mechanism with at least one external arm to contact and apply force to the first valve to move the first valve from the first position to the second position in the first channel.

19. The device of claim 17, wherein the purpose built centrifuge further comprises a first mechanism connected to and controls a first external arm and a second mechanism connected to and controls a second external arm, wherein the first mechanism can move the first external arm to contact and apply force to the first valve to move the first valve from the first position to the second position in the first channel, and the second mechanism can move the second external arm to contact and apply force to the second valve to move the second valve from the first position to the second position in the second channel.

20. The device of claim 18, wherein the mechanism is an air cylinder.

* * * * *